US010370664B2

(12) United States Patent
Feng et al.

(10) Patent No.: US 10,370,664 B2
(45) Date of Patent: Aug. 6, 2019

(54) USE OF IKK EPSILON INHIBITORS TO ACTIVATE NFAT AND T CELL RESPONSE

(71) Applicant: University of Southern California, Los Angeles, CA (US)

(72) Inventors: Pinghui Feng, La Canada, CA (US); Junjie Zhang, Monterey Park, CA (US); Hao Feng, Changsha (CN)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 15/034,529

(22) PCT Filed: Nov. 7, 2014

(86) PCT No.: PCT/US2014/064566
§ 371 (c)(1),
(2) Date: May 4, 2016

(87) PCT Pub. No.: WO2015/070027
PCT Pub. Date: May 14, 2015

(65) Prior Publication Data

US 2016/0289684 A1 Oct. 6, 2016

Related U.S. Application Data

(60) Provisional application No. 61/901,339, filed on Nov. 7, 2013.

(51) Int. Cl.

| | |
|---|---|
| ***C12N 15/113*** | (2010.01) |
| ***A61K 48/00*** | (2006.01) |
| ***A61K 31/436*** | (2006.01) |
| ***A61K 31/7105*** | (2006.01) |
| ***C07K 16/40*** | (2006.01) |

(52) U.S. Cl.
CPC ........ *C12N 15/1137* (2013.01); *A61K 31/436* (2013.01); *A61K 31/7105* (2013.01); *C07K 16/40* (2013.01); *C12N 15/113* (2013.01); *C12N 2310/14* (2013.01); *C12N 2310/531* (2013.01)

(58) Field of Classification Search
CPC .............. A01K 2207/05; C12N 15/113; C12N 15/1137; C07K 16/40
See application file for complete search history.

(56) References Cited

U.S. PATENT DOCUMENTS

| | | | |
|---|---|---|---|
| 5,580,859 | A | 12/1996 | Felgner et al. |
| 5,676,646 | A | 10/1997 | Hofmann et al. |
| 5,679,647 | A | 10/1997 | Carson et al. |
| 5,702,359 | A | 12/1997 | Hofmann et al. |
| 5,703,055 | A | 12/1997 | Feigner et al. |
| 6,068,650 | A | 5/2000 | Hofmann et al. |
| 6,096,020 | A | 8/2000 | Hofmann |
| 6,120,493 | A | 9/2000 | Hofmann |
| 6,150,148 | A | 11/2000 | Nanda et al. |
| 6,181,964 | B1 | 1/2001 | Hofmann et al. |
| 6,192,270 | B1 | 2/2001 | Hofmann et al. |
| 6,208,893 | B1 | 3/2001 | Hofmann |
| 6,216,034 | B1 | 4/2001 | Hofmann et al. |
| 6,233,482 | B1 | 5/2001 | Hofmann et al. |
| 6,241,701 | B1 | 6/2001 | Hofmann |
| 6,302,874 | B1 | 10/2001 | Zhang et al. |
| 7,664,545 | B2 | 2/2010 | Westersten et al. |

FOREIGN PATENT DOCUMENTS

| | | | |
|---|---|---|---|
| WO | 2004097009 | 11/2004 | |
| WO | WO-2005034978 A2 * | 4/2005 | ........... C12N 9/1205 |
| WO | 2009120801 | 10/2009 | |

OTHER PUBLICATIONS

Amini-Bavil-Olyaee et al., "The Antiviral Effector IFITM3 Disrupts Intracellular Cholesterol Homeostasis to Block Viral Entry", Cell Host Microbe, 2013, 13:4, pp. 452-464.
Bulek et al., "The inducible kinase IKKi is required for IL-17-dependent signaling associated with neutrophilia and pulmonary inflammation", Nat. Immunol., 2011, 12, pp. 844-852.
Chow et al., "c-Jun NH2-Terminal Kinase Inhibits Targeting of the Protein Phosphatase Calcineurin to NFATc1", Mol. Cell. Biol., 2000, 20:14, pp. 5227-5234.
Dong et al., "Murine Gamma-Herpesvirus 68 Hijacks MAVS and IKKβ to Initiate Lytic Replication", PLoS Pathog., 2010, 6, e1001001.
Donnelly et al.; "DNA vaccines" Ann. Rev. Immunol. 1997, 15, pp. 617-648.
Feng et al., "Kaposi's Sarcoma-Associated Herpesvirus K7 Induces Viral G Protein-Coupled Receptor Degradation and Reduces Its Tumorigenicity" PLoS Pathog., 2008, 4:9, e1000157.
Gerondakis et al. "Roles of the NF-KB pathway in lymphocyte development and function." Cold Spring Harbor perspectives in biology, 2010, 2, pp. 1-29.
Gregoriadis,"Liposome Technology,vols. I to III" (2nd ed.) CRC Press, 1993.
Hughes et al., "Pathogenesis of a Model Gammaherpesvirus in a Natural Host", 2010 J. Virol., 84:8, pp. 3949-3691.
Joliot et al., "Antennapedia homeobox peptide regulates neural morphogenesis", Proc. Natl. Acad. Sci. USA, 1991, 88, pp. 1864-1868.
Kyte et al., "A simple method for displaying the hydropathic character of a protein", J. Mol. Biol. 1982, 157, pp. 105-132.
Liu et al., "IKK Biology", Immunol. Rev., 2012, 246:1, pp. 239-253.
Molloy et al., "Suppressive CD8+ T Cells Arise in the Absence of CD4 Help and Compromise Control of Persistent Virus", J. Immunol., 2011, 186, pp. 6218-6226.
Moore et al. "Short hairpin RNA (shRNA: design, delivery, and assessment of gene knockdown." Methods Mol. Biol., 2010, 629, pp. 141-158.

(Continued)

*Primary Examiner* — Brian Whiteman
(74) *Attorney, Agent, or Firm* — Michael Best & Friedrich LLP

(57) ABSTRACT

Disclosed herein are compositions and methods of activating nuclear factor of activated T cells (NFAT) and T cell response by inhibiting IKKε.

14 Claims, 27 Drawing Sheets

Specification includes a Sequence Listing.

(56) References Cited

OTHER PUBLICATIONS

Tenoever et al., "Multiple functions of the IKK-related kinase IKKepsilon in interferon-mediated antiviral immunity", Science, 2007, 315:5816, pp. 1274-1278.
Wu et al., "Receptor-mediated in vitro gene transformation by a soluble DNA carrier system" J. Biol. Chem., 1987, 262, pp. 4429-4432.
International Search Report and Written Opinion for Application No. PCT/US2014/064566 dated Jan. 29, 2015 (11 pages).
International Preliminary Report on Patentability for Application No. PCT/US2014/064566 dated May 10, 2016 (7 pages).

* cited by examiner c

| Sequence | Ratio w/o IKKε | Ratio w IKKε | Function | Phospho-rylation |
|---|---|---|---|---|
| SPRIEIT (SEQ ID NO: 20) | 11/42 | 25/47 | Calcineurin docking | Indirect |
| SVTDDSWLG (SEQ ID NO: 19) | 7/35 | 11/26 | SP3 | Direct |
| SVTDDSWLG (SEQ ID NO: 19) | 2/35 | 6/26 | SP3 | Direct |
| KRSPSTATLSL (SEQ ID NO: 30) | 6/26 | 24/57 | Unknown | Direct* |
| TATLSLPSLEA (SEQ ID NO: 31) | 4/30 | 41/54 | Unknown | Direct* |
| DSSLDLGDG (SEQ ID NO: 32) | 25/90 | 40/70 | Unknown | Weak |

d e c d

USE OF IKK EPSILON INHIBITORS TO ACTIVATE NFAT AND T CELL RESPONSE

CROSS-REFERENCE TO RELATED APPLICATIONS

This is a U.S. national stage entry of International Patent Application No. PCT/US2014/064566, filed on Nov. 7, 2014, which claims priority to U.S. Provisional Patent Application No. 61/901,339, filed on Nov. 7, 2013, the entire contents of all of which are fully incorporated herein by reference.

STATEMENT OF GOVERNMENT INTEREST

This invention was made with government support under grant numbers CA134241, DE021445, and CA180779 awarded by the National Institutes of Health. The government has certain rights in the invention.

BRIEF DESCRIPTION OF SEQUENCE LISTING

The instant application contains a Sequence Listing which has been submitted in ASCII format via EFS-Web and is hereby incorporated by reference in its entirety. Said ASCII copy, created on Nov. 7, 2014, is named 2014-099-03-029680-9017-US01-SEQ-LIST-05-04-16.txt, and is 31,974 bytes in size.

TECHNICAL FIELD

The present invention relates to compositions and methods of activating nuclear factor of activated T cells (NFAT) and T cell response by inhibiting IKKε.

BACKGROUND

T cells constitute an important part of the adaptive immune system. Strategies to increase anti-tumor cytotoxic T-cell (CTL) responses include administration of YERVOY® (Ipilimumab), which is marketed to treat patients with late-stage melanoma. Ipilimumab is an antibody-based therapy that blocks CTLA-4 to activate CTLs and allow the CTLs to kill the tumor cells. Another example is Lambrolizumab, which is a monoclonal antibody that targets the Programmed cell death 1 (PD-1) receptor and is used to treat metastatic melanoma. The activation of T cells is primarily enabled by the dephosphorylation of nuclear factor of activated T cells (NFAT). Various kinases can phosphorylate NFAT and down-regulate T cell response, however their in vivo roles in T cell response are not known. It would be beneficial to have other means of increasing T cell response and anti-tumor activity.

SUMMARY

The present disclosure is directed to a method for treating a subject suffering from or at risk of developing a disease. The method may comprise administering to the subject an IKKε inhibitor. The disease may comprise an infectious disease or cancer. The disease may comprise a viral infection. The IKKε inhibitor may comprise amlexanox, an inhibitory RNA, an antibody, or a combination thereof. The inhibitory RNA may target IKKε. The inhibitory RNA may comprise a shRNA. The shRNA may comprise a polynucleotide sequence selected from the group consisting of SEQ ID NO: 1 or SEQ ID NO: 2. The IKKε inhibitor may increase NFAT activation relative to a control. The IKKε inhibitor may increase T cell response relative to a control. CD8 T cell response may be increased relative to a control. The infectious disease may comprise a viral infection and the IKKε inhibitor may increase anti-viral T-cell mediated immunity. The infectious disease may comprise a microbial infection and the IKKε inhibitor may increase anti-microbial T-cell mediated immunity. The disease may comprise cancer and the IKKε inhibitor may increase anti-cancer T-cell mediated immunity. The T cell response may be increased by at least about 2-fold to at least about 10-fold.

In another aspect, provided is a method of increasing NFAT activation in a subject. The method may comprise administering to the subject an IKKε inhibitor. The IKKε inhibitor may comprise amlexanox, an inhibitory RNA, an antibody, or a combination thereof. The inhibitory RNA may target IKKε. The inhibitory RNA may comprise a shRNA. The shRNA may comprise a polynucleotide sequence selected from the group consisting of f SEQ ID NO: 1 or SEQ ID NO: 2. CD8 T cell response may be increased relative to a control. A therapeutically effective amount of the IKKε inhibitor may be administered.

In another aspect, provided is a method of increasing T cell response in a subject. The method may comprise administering to the subject an IKKε inhibitor. The IKKε inhibitor may comprise amlexanox, an inhibitory RNA, an antibody, or a combination thereof. The inhibitory RNA may target IKKε. The inhibitory RNA may comprise a shRNA. The shRNA may comprise a polynucleotide sequence selected from the group consisting of f SEQ ID NO: 1 or SEQ ID NO: 2. CD8 T cell response may be increased relative to a control. A therapeutically effective amount of the IKKε inhibitor may be administered.

In another aspect, provided is a method of increasing NFAT activation and T cell response in a subject. The method may comprise administering to the subject an IKKε inhibitor. The IKKε inhibitor may comprise amlexanox, an inhibitory RNA, an antibody, or a combination thereof. The inhibitory RNA may target IKKε. The inhibitory RNA may comprise a shRNA. The shRNA may comprise a polynucleotide sequence selected from the group consisting of SEQ ID NO:1 or SEQ ID NO: 2. CD8 T cell response may be increased relative to a control. A therapeutically effective amount of the IKKε inhibitor may be administered.

In another aspect, provided is a pharmaceutical composition that comprises one or more of amlexanox, an inhibitory RNA, and/or an antibody. The inhibitory RNA may be a shRNA. The shRNA may be SEQ ID NO:1 and/or SEQ ID NO:2 or a variant of SEQ ID NO:1 and/or SEQ ID NO:2, for example.

DETAILED DESCRIPTION

Figure 1:
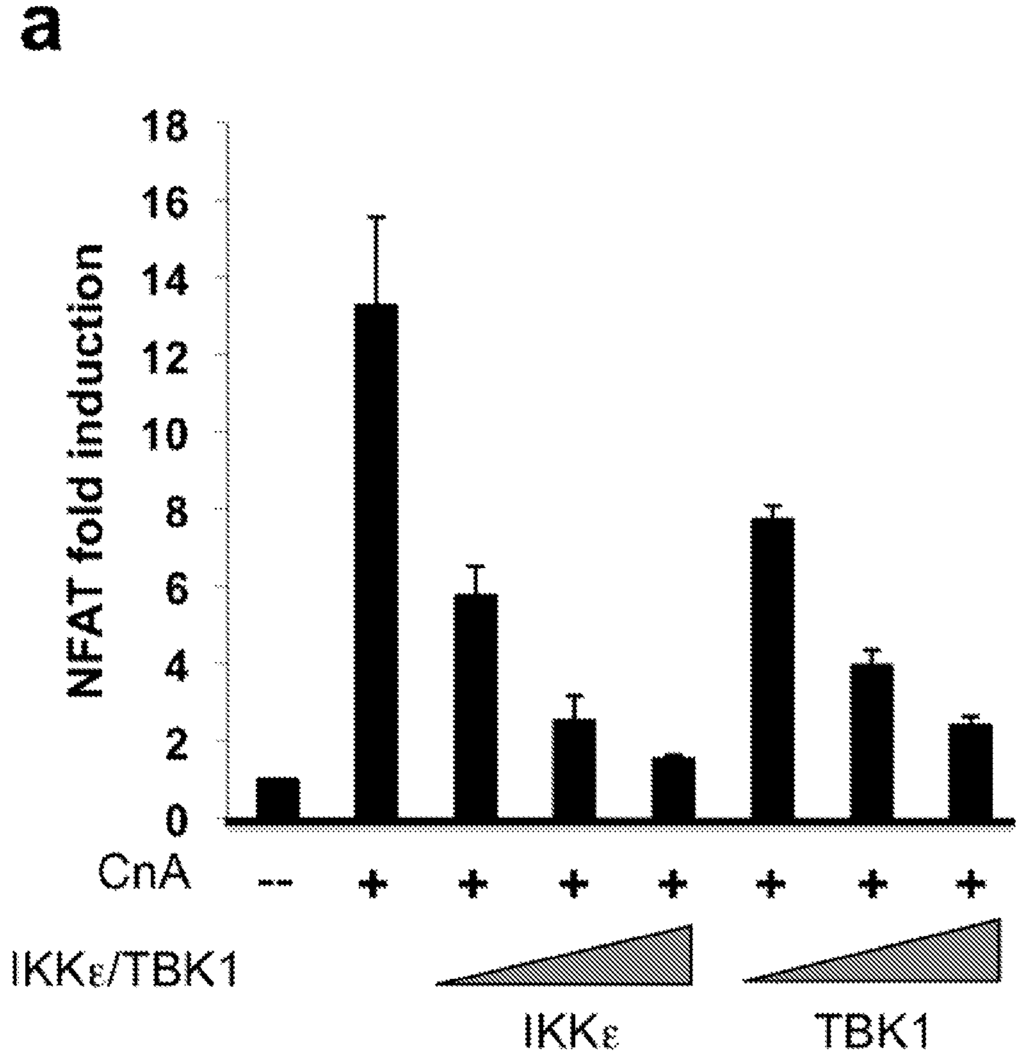
FIG. 1 shows that IKKε inhibits NFAT activation in a kinase-dependent manner. (A-D) 293T cells were transfected with a reporter plasmid cocktail and plasmids containing indicated genes. NFAT activation was determined by luciferase assay. IKKε and TBK1 inhibit NFAT activation induced by calcineurin (CnA) (A) and NFAT2 (B) in a dose-dependent manner. (C) IKKε and DYRK inhibit NFAT activation induced by NFAT2 expression. (D) IKKε, but not the kinase-dead IKKεK38A, inhibited NFAT activation induced by calcineurin. (E and F) 293T cells were transfected with a plasmid containing EGFP-NFAT2 alone, or with plasmids containing wild-type IKKε and IKKεK38A. Cells were treated with ionomycin (1 μM) for 1 h. NFAT activation was analyzed by fluorescence microscopy. Representative images were shown (E). A total of ~300 cells were counted for nuclear NFAT2 localization and percentage was calculated (F).
Figure 1:
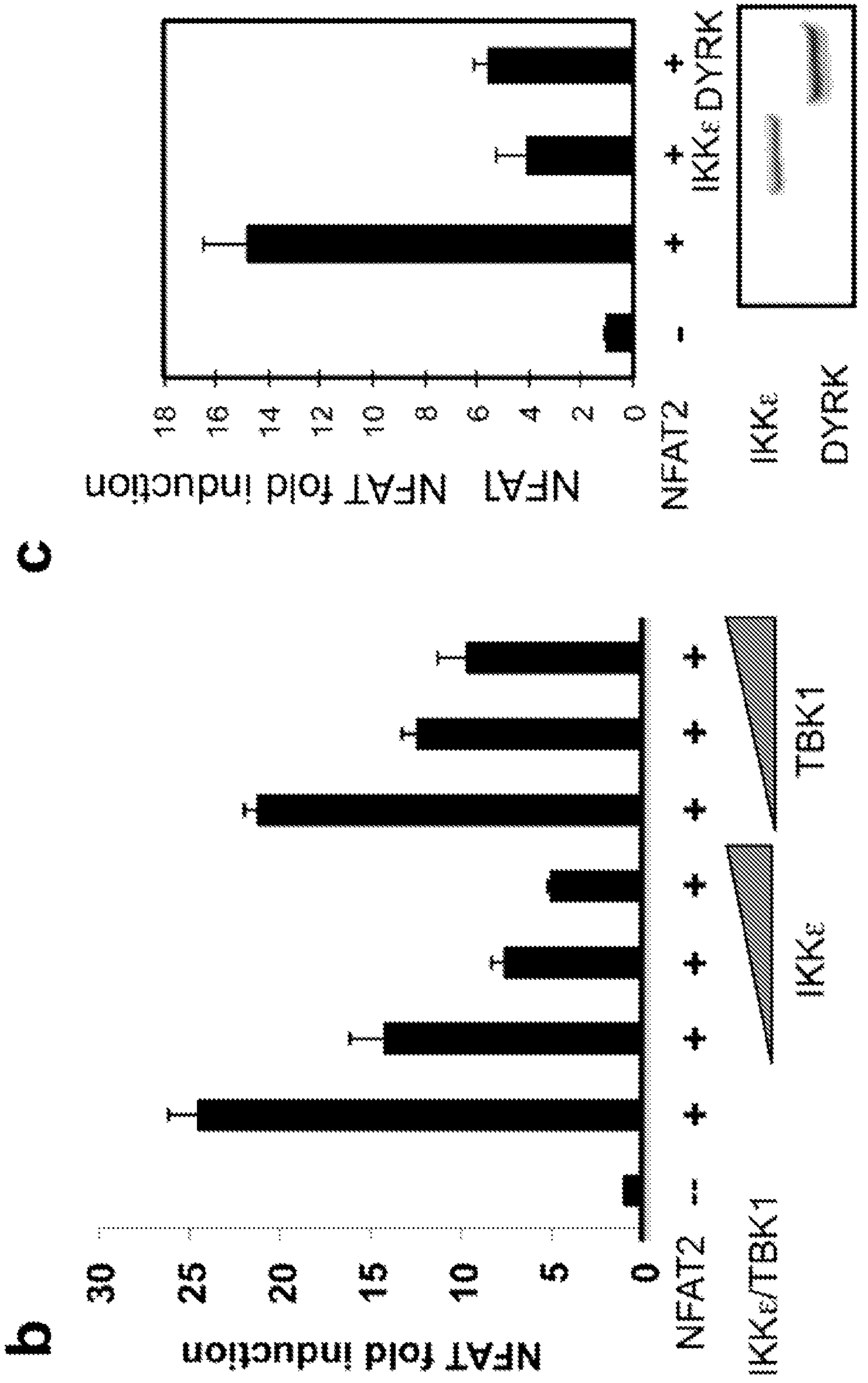
Figure 1:
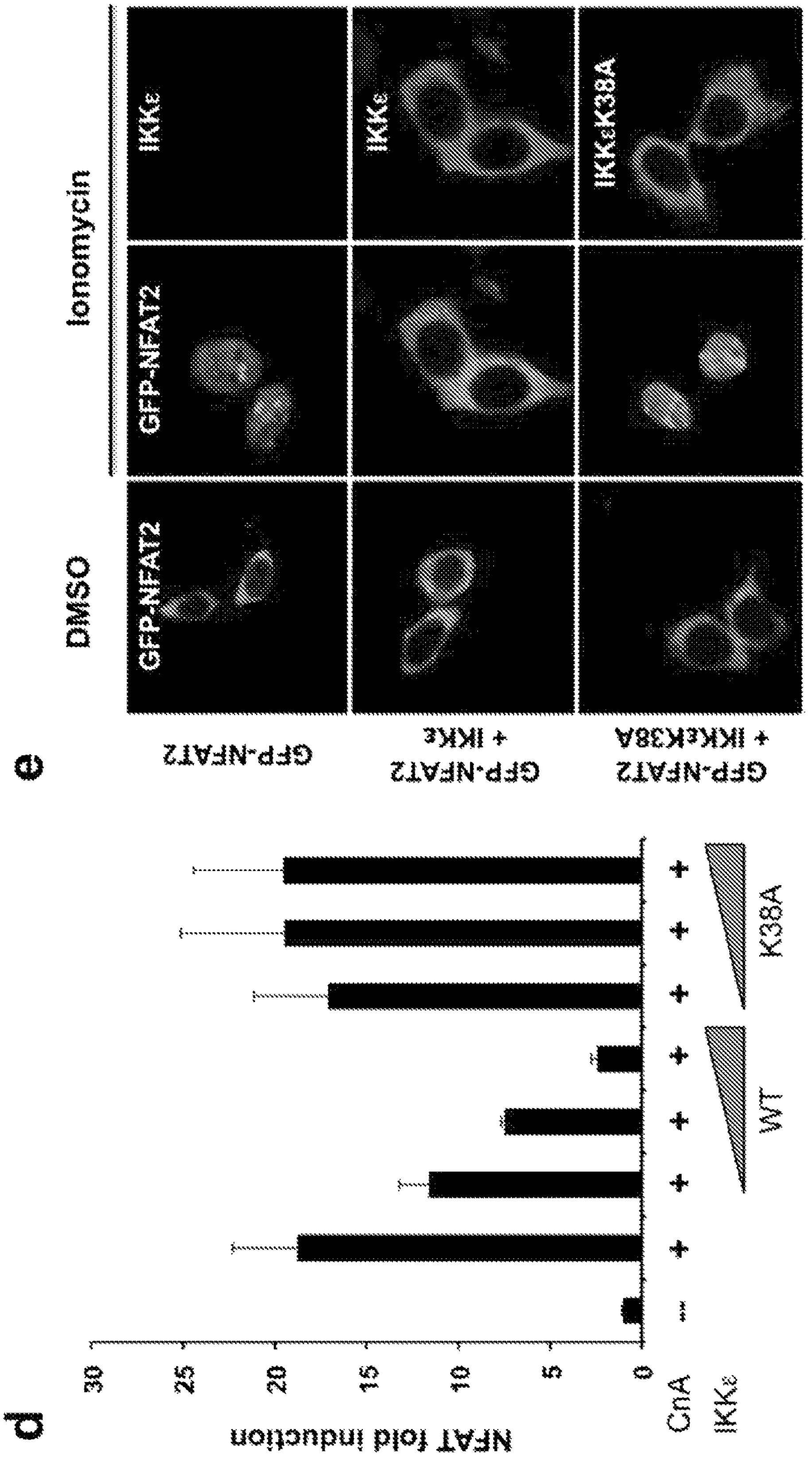
Figure 1:
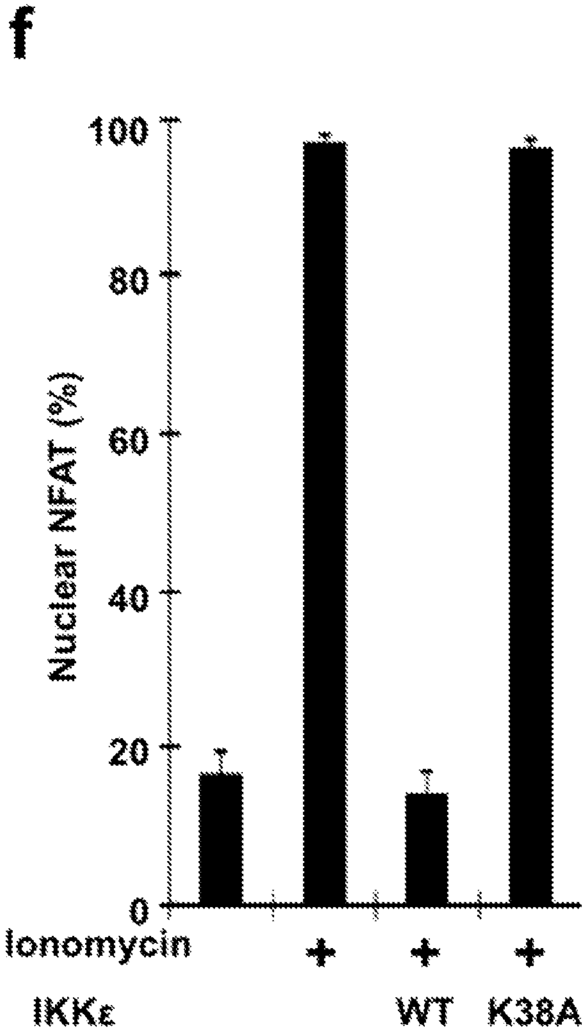

The present disclosure provides compositions and methods of preventing or treating a subject suffering from or at risk of suffering from a disease or condition, such as an infectious disease or cancer, by increasing NFAT activation and T cell response through the inhibition of κB kinase (IKK) epsilon (IKKε). The compositions and methods center on a previously unidentified role of IKKε in T cells. IKKε is a non-canonical IKK-related kinase that regulates interferon signal transduction of the innate immune defense and is expressed abundantly in T cells.

As shown herein, IKKε plays a regulatory function of the innate immune signaling pathways that combat against pathogen infection and tumor development by inhibiting NFAT activation and T cell response by phosphorylating NFAT. Conversely, it was discovered that loss of IKKε results in an elevated T cell response in mice infected with two representative viral pathogens. Mass spectrometry analysis identified multiple phosphorylation sites within the regulatory domain of NFA, mutations of which render NFAT resistant to IKKε-mediated inhibition. Knockdown or pharmacological inhibition of IKKε elevates NFAT-dependent gene expression and T cell activation. Accordingly, loss of IKKε increases virus-specific CD8 T cell response that contributes to an overall antiviral immunity. Provided herein are compositions and methods of increasing NFAT activation and T cell response by inhibiting IKKε. IKKε inhibition may be used to mitigate diseases caused by infectious agents or various cancers and/or applied to various endeavors including immunotherapy, wherein host T cells are isolated and expanded to combat diseases. Diseases caused by infectious agents or various cancers may be mitigated by targeting therapies to IKKε and enhancing NFAT signaling and subsequent T cell response.

1. DEFINITIONS

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and," and "the" include plural references unless the context clearly dictates otherwise. The present disclosure also contemplates other embodiments "comprising," "consisting of," and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The term "about" as used herein as applied to one or more values of interest, refers to a value that is similar to a stated reference value. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Biological sample" or "sample" may be any sample or isolate taken or derived from a subject. Any cell type, tissue, or bodily fluid may be utilized to obtain a sample. Such cell types, tissues, and fluids may include sections of tissues such as biopsy and autopsy samples, frozen sections taken for histological purposes, blood (such as whole blood), plasma, serum, sputum, stool, urine, tears, mucus, saliva, sweat, hair, skin, red blood cells, white blood cells, platelets, interstitial fluid, ocular lens fluid, nasal fluid, synovial fluid, menses, amniotic fluid, semen, lymph fluid, ascetic fluid, gynecological fluid, peritoneal fluid, cerebrospinal fluid, a fluid collected by vaginal rinsing, or a fluid collected by vaginal flushing, placental cells or tissue, endothelial cells, leukocytes, or monocytes. A tissue or cell type may be provided by removing a sample of cells from an animal, but can also be accomplished by using previously isolated cells (e.g., isolated by another person, at another time, and/or for another purpose). Archival tissues, such as those having treatment or outcome history, may also be used. Protein or nucleotide isolation and/or purification may or may not be necessary. Samples can be used directly as obtained from a subject or can be pre-treated, such as by filtration, distillation, extraction, concentration, centrifugation, precipitation, inactivation of interfering components, addition of reagents, and the like, to modify the character of the sample in some manner as discussed herein or otherwise as is known in the art.

"Cancer" as used herein refers to the uncontrolled and unregulated growth of abnormal cells in the body. Cancerous cells are also called malignant cells. Cancer may comprise a tumor. A tumor may be malignant or benign. Cancer may invade nearby parts of the body and may also spread to more distant parts of the body through the lymphatic system or bloodstream. Cancers include Adrenocortical Carcinoma, Anal Cancer, Bladder Cancer, Brain Tumor, Breast Cancer, Carcinoid Tumor, Gastrointestinal, Carcinoma of Unknown Primary, Cervical Cancer, Colon Cancer, Endometrial Cancer, Esophageal Cancer, Extrahepatic Bile Duct Cancer, Ewings Family of Tumors (PNET), Extracranial Germ Cell Tumor, Intraocular Melanoma Eye Cancer, Gallbladder Cancer, Gastric Cancer (Stomach), Extragonadal Germ Cell Tumor, Gestational Trophoblastic Tumor, Head and Neck Cancer, Hypopharyngeal Cancer, Islet Cell Carcinoma, Kidney Cancer (renal cell cancer), Laryngeal Cancer, Acute Lymphoblastic Leukemia, Leukemia, Acute Myeloid, Chronic Lymphocytic Leukemia, Chronic Myelogenous Leukemia, Hairy Cell Leukemia, Lip and Oral Cavity Cancer, Liver Cancer, Non-Small Cell Lung Cancer, Small Cell Lung Cancer, AIDS-Related Lymphoma, Central Nervous System (Primary) Lymphoma, Cutaneous T-Cell Lymphoma, Hodgkin's Disease Lymphoma, Non-Hodgkin's Disease Lymphoma, Malignant Mesothelioma, Melanoma, Merkel Cell Carcinoma, Metasatic Squamous Neck Cancer with Occult Primary, Multiple Myeloma and Other Plasma Cell Neoplasms, Mycosis Fungoides, Myelodysplastic Syndrome, Myeloproliferative Disorders, Nasopharyngeal Cancer, euroblastoma, Oral Cancer, Oropharyngeal Cancer, Osteosarcoma, Ovarian Epithelial Cancer, Ovarian Germ Cell Tumor, Pancreatic Cancer, Exocrine, Pancreatic Cancer, Islet Cell Carcinoma, Paranasal Sinus and Nasal Cavity Cancer, Parathyroid Cancer, Penile Cancer, Pituitary Cancer, Plasma Cell Neoplasm, Prostate Cancer, Rhabdomyosarcoma, Rectal Cancer, Renal Cell Cancer (cancer of the kidney), Transitional Cell Renal Pelvis and Ureter, Salivary Gland Cancer, Sezary Syndrome, Skin Cancer, Small Intestine Cancer, Soft Tissue Sarcoma, Testicular Cancer, Malignant Thymoma, Thyroid Cancer, Urethral Cancer, Uterine Cancer, Unusual Cancer of Childhood, Vaginal Cancer, Vulvar Cancer, and Wilms' Tumor.

"Control" or "control subject" as used herein refers to a subject who has not been administered the disclosed IKKε inhibitor. The control subject can be a healthy subject, i.e., a subject having no clinical signs or symptoms of disease, or a subject who has been diagnosed with a disease but has not been administered the disclosed IKKε inhibitor. A control may be a biological sample from a control subject. A control may include an average or average range of parameters or levels from a population of control subjects. A control may be a standard value developed by analyzing the results of a population of control subjects. Those skilled in the art will appreciate that a variety of controls may be used.

"Immune response" as used herein means the activation of a host's immune system, e.g., that of a mammal, in response to the introduction of antigen. The immune response can be in the form of a cellular or humoral response, or both.

"Infectious diseases" as used herein refers to diseases caused by pathogenic microorganisms, such as bacteria, viruses, parasites, or fungi. The infectious disease may be a bacterial, viral, parasitic, or fungal infection. Infectious diseases may include, but are not limited to, herpes simplex virus 1 (HSV 1), herpes virus 2 (HSV 2), human immunodeficiency virus infection (HIV), Epstein barr, papilloma virus, cellulitis, mycobacteria, influenza, parainfluenza, adenoviruses, encephalitis, meningitis, arbovirus, arenavirus, anaerobic bacilli, picornavirus, coronavirus and synsytialvirus, varicella zoster virus, cytomegalovirus, cellulitis, staphylococci, such as *Staphylococcus aureus*, streptococci, mycobacteria, bacterial encephalitis, anaerobic bacilli, such as *Bacillus cereus, Vibrio parahaemolyticus*, Enterohemorrhagic *Escherichia coli*, MRSA, *Salmonella*, Botulinus, *Candida*, tuberculosis, measles, mumps, rubella, diphtheria, pertussis, Hemophilus influenza, tetanus, hepatitis B, polio, anthrax, plague, meningococcal, meningitis, pneumococcus, typhus, typhoid fever, *Neisseria*, Lyme, cytomegalovirus (CMV), respiratory syncytial virus, E rotavirus, hepatitis A, hepatitis B, hepatitis C, rabies, yellow fever, Japanese encephalitis, flavivirus, dengue, toxoplasmosis, cocidiomycosis, schistosomiasis, malaria, herpetic keratitis, conjunctivitis, roseola infantum, mononucleosis, uveitis, retinitis, human cervical carcinoma, vaginal carcinoma, vulvovaginitis, human herpes IV, Kaposi's sarcoma, and common colds.

"Polynucleotide" as used herein can be single stranded or double stranded, or can contain portions of both double stranded and single stranded sequence. The polynucleotide can be nucleic acid, natural or synthetic, DNA, genomic DNA, cDNA, RNA, or a hybrid, where the polynucleotide can contain combinations of deoxyribo- and ribo-nucleotides, and combinations of bases including uracil, adenine, thymine, cytosine, guanine, inosine, xanthine hypoxanthine, isocytosine, and isoguanine. Polynucleotides can be obtained by chemical synthesis methods or by recombinant methods.

A "peptide" or "polypeptide" is a linked sequence of amino acids and can be natural, synthetic, or a modification or combination of natural and synthetic. Peptides and polypeptides include proteins such as antibodies.

"Subject" as used herein can mean a mammal that wants to or is in need of being treated with the herein described agent-polypeptide construct. The mammal can be a human, dog, cat, horse, cow, pig, mouse, rat, or non-human primate such as, for example, chimpanzee, gorilla, orangutan, and gibbon.

"Substantially identical" can mean that a first and second amino acid sequence are at least 60%, 65%, 70%, 75%, 80%, 85%, 90%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 amino acids.

"Treatment" or "treating," when referring to protection of an animal from a disease, means preventing, suppressing, repressing, ameliorating, or completely eliminating the disease. Preventing the disease involves administering a composition of the present invention to an animal prior to onset of the disease. Suppressing the disease involves administering a composition of the present invention to an animal after induction of the disease but before its clinical appearance. Repressing or ameliorating the disease involves administering a composition of the present invention to an animal after clinical appearance of the disease.

"T cell activation" or "T cell response" as used interchangeably herein refers to the activation of cytotoxic T cells. T cell activation may be identified by measuring changes in IL-2 mRNA levels. For example, an increase of IL-2 mRNA levels in cells, such as in a Jurkat cell, may indicate T cell activation. T cell activation may be identified by an increase in T cell count. T cell count may include CD8 T cells. T cell count may include CD4 T cells. T cell count may be total T cell count, which includes CD8 and CD4 T cells.

"Variant" used herein with respect to a polynucleotide means (i) a portion or fragment of a referenced nucleotide sequence; (ii) the complement of a referenced nucleotide sequence or portion thereof; (iii) a polynucleotide that is substantially identical to a referenced polynucleotide or the complement thereof; or (iv) a polynucleotide that hybridizes under stringent conditions to the referenced polynucleotide, complement thereof, or a sequences substantially identical thereto.

A "variant" can further be defined as a peptide or polypeptide that differs in amino acid sequence by the insertion, deletion, or conservative substitution of amino acids, but retain at least one biological activity. Representative examples of "biological activity" include the ability to be bound by a specific antibody or to promote an immune response. Variant can mean a substantially identical sequence. Variant can mean a functional fragment thereof. Variant can also mean multiple copies of a polypeptide. The multiple copies can be in tandem or separated by a linker. Variant can also mean a polypeptide with an amino acid sequence that is substantially identical to a referenced polypeptide with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids. See Kyte et al., *J. Mol. Biol.* 1982, 157, 105-132. The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophibicity of amino acids can also be used to reveal substitutions that would result in polypeptides retaining biological function. A consideration of the hydrophilicity of amino acids in the context of a polypeptide permits calculation of the greatest local average hydrophilicity of that polypeptide, a useful measure that has been reported to correlate well with antigenicity and immunogenicity, as discussed in U.S. Pat. No. 4,554,101, which is fully incorporated herein by reference. Substitution of amino acids having similar hydrophilicity values can result in polypeptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant can be a polynucleotide sequence that is substantially identical over the full length of the full gene sequence or a fragment thereof. The polynucleotide sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant can be an amino acid sequence that is substantially identical over the full length of the amino acid sequence or fragment thereof. The amino acid sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

2. NFAT

According to the compositions and methods detailed herein, "nuclear factor of activated T-cells" or "NFAT" is used interchangeably herein and refers to a family of transcription factors involved in immune response and expressed in most cells of the immune system. The NFAT transcription factor family includes five members: NFATc1, NFATc2 (also referred to as "NFAT2"), NFATc3, NFATc4, and NFAT5. "NFAT" may refer to the family of proteins or at least one protein in the NFAT family. NFAT is also involved in the development of cardiac, skeletal muscle, and nervous systems. NFAT has a role in T cell activation, as well as roles in other immune and non-immune cells and biological processes such as development and stem cell maintenance.

NFAT contains an amino terminal transactivation domain, a regulatory domain, a DNA binding domain, and a carboxy terminal domain. Kinases regulate the nuclear import of NFAT proteins. The internal regulatory domain contains multiple serine/threonine-rich motifs that are phosphorylated by various kinases in resting cells, such as, for example, casein kinase 1 (CK1), glycogen synthase kinase 3β (GSK3β), and the dual-specificity tyrosine-phosphorylation-regulated kinase (DYRK). Coordinated phosphorylation of NFAT by these kinases inactivates and excludes NFAT from the nucleus. NFATc1 through NFATc4 are regulated by calcium signaling. Calcium signaling is involved in NFAT activation because calmodulin, which is a calcium-dependent enzyme, activates the serine/threonine phosphatase calcineurin (CN). Activated CN rapidly dephosphorylates the serine-rich region (SRR) and SP-repeats in the amino terminal domain of a NFAT protein. Dephosphorylation causes a conformational change of the NFAT protein and enables NFAT nuclear translocation.

Various serine residues of NFAT may be dephosphorylated to enable NFAT nuclear translocation. Conversely, various serine residue of NFAT may serve as phosphoracceptors and be phosphorylated to prevent NFAT nuclear translocation. The serine residues may be present in serine-rich motifs of NFAT such as SRR1, SRR2, SP1, SP2 (SPQHSPSTSPRASVTEESWLG, SEQ ID NO: 27), and SP3 (SPHHSPTPSPHGSPRVSVTDDSWLG, SEQ ID NO. 28). The serine residues may be present in the SP2 sequence of NFAT. The serine residues may be present in the SP3 sequence NFAT. The serine residues may be present in a sequence motif comprising SVTDDSWLG (SEQ ID NO:19) of NFAT. The serine residues may be present in a sequence motif comprising SVTEESWLG (SEQ ID NO:29) of NFAT. For example, the serine residues may include at least one of $S^{117}$, $S^{151}$, $S^{161}$, $S^{294}$, $S^{299}$, and $S^{324}$ of NFAT.

3. IKKε

"Inhibitor of nuclear factor kappa-B kinase subunit epsilon", "IKKepsilon", or "IKKε" as used interchangeably herein refers to a kinase that is encoded by the IKBKE gene in humans. IKKε is also known as I-kappa-B kinase epsilon or IKK-epsilon. IKKε is an IKK-related kinase that is inducible by inflammatory stimuli.

IKKε may comprise an amino acid sequence consisting of SEQ ID NOs: 21, 23, or 25, which is encoded by a polynucleotide sequence of SEQ ID NOs: 22, 24, or 26, respectively. SEQ ID NOs: 21, 23, and 25 refer to isoforms 1, 2, and 3, respectively, of the full-length wild-type human polypeptide sequence. IKKε can comprise a polypeptide having an amino acid sequence that is 80%, 81%, 82%, 83%, 84%, 85%, 86%, 87%, 88%, 89%, 90%, 91%, 92%, 93%, 94%, 95%, 96%, 97%, 98%, or 99% identical over the entire length of the amino acid sequence of SEQ ID NOs: 21, 23, or 25. IKKε can comprise a polypeptide having an amino acid sequence that is 80%-99%, 85%-99%, or 90-99% identical over the entire length of the amino acid sequence of SEQ ID NOs: 21, 23, or 25.

As detailed in the Examples, IKKε was found to promote NFAT phosphorylation. IKKε may phosphorylate NFAT at one or more serine residues. The serine residues may be present in the SP2 sequence of NFAT. The serine residues may be present in the SP3 sequence NFAT. IKKε may phosphorylate NFAT at one or more of $S^{117}$, $S^{151}$, $S^{161}$, $S^{294}$, $S^{299}$, and $S^{324}$.

a. IKKε Inhibitors

"IKKε inhibitor" as used interchangeably herein refers to a drug or compound which interacts with IKKε enzyme and decreases IKKε enzyme activity, either indirectly or directly or a combination thereof. The IKKε inhibitor may be used to treat a subject having an infectious disease or cancer. The CYP27A1 inhibitor may be a small molecule, such as amlexanox (2-amino-7-isopropyl-5-oxo-5H-chromeno[2,3-b]pyridine-3-carboxylic acid). The IKKε inhibitor may be a benzimidazole analog such as 5-(5,6-dimethoxy-1H-benzimidazol-1-yl)-3-[[2-(methylsulfonyl)phenyl]methoxy]-2-thiophenecarbonitrile (IKK-s Kinase Inhibitor II, CAS No. 862812-98-4). The IKKε inhibitor may be an inhibitory RNA targeting IKKε. The IKKε inhibitor may be an inhibitory RNA, such as a dsRNA, a siRNA, a piRNA, an antisense RNA, a RNAse external guide sequence, a miRNA, a ribozyme, or a short hairpin RNA (shRNA) comprising a sequence complementary to a portion of an RNA sequence encoding IKKε, human IKBKE. For example, the IKKε inhibitor may be shRNA specific for IKKε such as shRNA 77 (CCGGCTGGACGATGATGAGAAGTTTCTCGAGAAACTTCTCATCATCGTCCAGTTT TT, SEQ ID NO: 1) or shRNA 78 (CCGGAGAAGTTCGTCTCGGTCTATGCTCGAGCATAGACCGAGACGAACTTCTTTT TTG, SEQ ID NO:2). The IKKε inhibitor may be a polypeptide. The IKKε inhibitor may be an antibody that binds IKKε.

The IKKε inhibitor may cause a decrease in the phosphorylation of an NFAT protein. The IKKε inhibitor may cause a decrease in the phosphorylation of an NFAT protein by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% compared to a control subject. The IKKε inhibitor may cause a decrease in the phosphorylation of an NFAT protein by about 5% to about 99%, about 10% to about 98%, about 15% to about 97%, about 20% to about 96%, or about 25% to about 95% compared to a control subject. The IKKε inhibitor may cause a decrease in the phosphorylation of an NFAT protein by at least about 1-fold, at least about 2-fold, at least about 3-fold, at least about 4-fold, at least about 5-fold, at least about 6-fold, at least about 7-fold, at least about 8-fold, at least about 9-fold, or at least about 10-fold compared to a control subject. The IKKε inhibitor may cause a decrease in the phosphorylation of an NFAT protein by about 1-fold to about 100-fold, about 2-fold to about 75-fold, about 3-fold to about 50-fold, about 4-fold to about 25 fold, or about 5-fold to about 20-fold compared to a control subject. The decrease in phosphorylation of an NFAT protein may be relative to one or more phosphorylated serine residues and compared to a control subject.

The IKKε inhibitor may cause an increase in NFAT activation. The IKKε inhibitor may cause an increase in NFAT activation by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% compared to a control subject. The IKKε inhibitor may cause an increase in NFAT activation by about 5% to about 99%, about 10% to about 98%, about 15% to about 97%, about 20% to about 96%, or about 25% to about 95% compared to a control subject. The IKKε inhibitor may cause an increase in NFAT activation by at least about 1-fold, at least about 2-fold, at least about 3-fold, at least about 4-fold, at least about 5-fold, at least about 6-fold, at least about 7-fold, at least about 8-fold, at least about 9-fold, or at least about 10-fold compared to a control subject. The IKKε inhibitor may cause an increase in NFAT activation by at least about 1-fold to about 100-fold, about 2-fold to about 75-fold, about 3-fold to about 50-fold, about 4-fold to about 25 fold, or about 5-fold to about 20-fold compared to a control subject. The increase in NFAT activation may be relative to a control subject.

The IKKε inhibitor may cause an increase in a virus-specific T cell response in a subject. An increase in a virus-specific T cell response may include or result in an increase in anti-viral T-cell mediated immunity. The IKKε inhibitor may cause an increase in a virus-specific T cell response in a subject by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% compared to a control subject. The IKKε inhibitor may cause an increase in a virus-specific T cell response in a subject by about 5% to about 99%, about 10% to about 98%, about 15% to about 97%, about 20% to about 96%, or about 25% to about 95% compared to a control subject. The IKKε inhibitor may cause an increase in a virus-specific T cell response in a subject by at least about 1-fold, at least about 2-fold, at least about 3-fold, at least about 4-fold, at least about 5-fold, at least about 6-fold, at least about 7-fold, at least about 8-fold, at least about 9-fold, or at least about 10-fold compared to a control subject. The IKKε inhibitor may cause an increase in a virus-specific T cell response in a subject by at least about 1-fold to about 100-fold, about 2-fold to about 75-fold, about 3-fold to about 50-fold, about 4-fold to about 25 fold, or about 5-fold to about 20-fold compared to a control subject. An increase in anti-viral T-cell mediated immunity may correlate with an increase in T-cell activation.

The IKKε inhibitor may cause an increase in a microbial-specific T cell response. An increase in a microbial-specific T cell response may include or result in an increase in anti-microbial T-cell mediated immunity. The IKKε inhibitor may cause an increase in anti-microbial T-cell mediated immunity in a subject by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% compared to a control subject. The IKKε inhibitor may cause an increase in anti-microbial T-cell mediated immunity in a subject by about 5% to about 99%, about 10% to about 98%, about 15% to about 97%, about 20% to about 96%, or about 25% to about 95% compared to a control subject. The IKKε inhibitor may cause an increase in anti-microbial T-cell mediated immunity in a subject by at least about 1-fold, at least about 2-fold, at least about 3-fold, at least about 4-fold, at least about 5-fold, at least about 6-fold, at least about 7-fold, at least about 8-fold, at least about 9-fold, or at least about 10-fold compared to a control subject. The IKKε inhibitor may cause an increase in anti-microbial T-cell mediated immunity in a subject by at least about 1-fold to about 100-fold, about 2-fold to about 75-fold, about 3-fold to about 50-fold, about 4-fold to about 25 fold, or about 5-fold to about 20-fold compared to a control subject. The increase in anti-microbial T-cell mediated immunity may correlate with an increase in T-cell activation.

The IKKε inhibitor may cause an increase in a cancer-specific T cell response. An increase in a cancer-specific T cell response may include or result in an increase in anti-cancer T-cell mediated immunity. The IKKε inhibitor may cause an increase in anti-cancer T-cell mediated immunity in a subject by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% compared to a control subject. The IKKε inhibitor may cause an increase in anti-cancer T-cell mediated immunity in a subject by about 5% to about 99%, about 10% to about 98%, about 15% to about 97%, about 20% to about 96%, or about 25% to about 95% compared to a control subject. The IKKε inhibitor may cause an increase in anti-cancer T-cell mediated immunity in a subject by at least about 1-fold, at least about 2-fold, at least about 3-fold, at least about 4-fold, at least about 5-fold, at least about 6-fold, at least about 7-fold, at least about 8-fold, at least about 9-fold, or at least about 10-fold compared to a control subject. The IKKε inhibitor may cause an increase in anti-cancer T-cell mediated immunity in a subject by at least about 1-fold to about 100-fold, about 2-fold to about 75-fold, about 3-fold to about 50-fold, about 4-fold to about 25 fold, or about 5-fold to about 20-fold compared to a control subject. The increase in anti-cancer T-cell mediated immunity may correlate with an increase in T-cell activation.

4. METHODS a. Methods of Preventing or Treating a Subject Suffering from or at Risk of Developing a Disease The present invention is directed to methods of preventing or treating a subject suffering from or at risk of developing a disease. The method may comprise administering to the subject an IKKε inhibitor. The disease may comprise a T cell responsive disease. The disease may be a T cell responsive disease. T cell responsive diseases may include infectious diseases and cancer. The disease may comprise cancer. The disease may comprise an infectious disease.

b. Methods of Increasing NFAT Activation in a Subject

Further provided are methods of increasing NFAT activation in a subject. The method may comprise administering to the subject an IKKε inhibitor. For example, increasing NFAT activation may provide a beneficial result other than, or in addition to, preventing or treating a T cell responsive disease. Increasing NFAT activation may prevent or treat a condition other than a T cell responsive disease.

c. Methods of Increasing T Cell Response in a Subject

Further provided are methods of increasing a T cell response in a subject. The method may comprise administering to the subject an IKKε inhibitor. For example, increasing a T cell response may provide a beneficial result other than, or in addition to, preventing or treating a T cell responsive disease. Increasing a T cell response may prevent or treat a condition other than a T cell responsive disease.

5. PHARMACEUTICAL COMPOSITIONS

The IKKε inhibitor may be typically administered as part of a pharmaceutical composition, which may further comprise, for example, lyoprotectants, surfactants, bulking agents, tonicity adjusting agents, stabilizers, preservatives and/or buffers. The pharmaceutical composition may also contain a pharmaceutically acceptable carrier. The pharmaceutical compositions comprising the IKKε inhibitor may be for use in, but not limited to, monitoring a disorder or injury, in preventing, treating, managing, or ameliorating of a disorder or injury or one or more symptoms thereof, and/or in research. In one embodiment, a composition comprises one or more IKKε inhibitors. In another embodiment, the pharmaceutical composition may further comprise a carrier, diluent, or excipient.

As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In some embodiments, isotonic agents, for example, sugars, polyalcohols such as mannitol, sorbitol, or sodium chloride, may be included in the composition. Pharmaceutically acceptable carriers may further comprise minor amounts of auxiliary substances such as wetting or emulsifying agents, preservatives, or buffers, which enhance the shelf life or effectiveness of the IKKε inhibitor.

Various delivery systems are known and can be used to administer one or more IKKε inhibitors for preventing, managing, treating, or ameliorating a disorder or injury or one or more symptoms thereof. The pharmaceutical composition comprising IKKε inhibitor can be a liquid preparation such as a suspension, syrup, or elixir. The IKKε inhibitor can be incorporated into liposomes, microspheres, or other polymer matrices (such as by a method described in Felgner et al., U.S. Pat. No. 5,703,055; Gregoriadis, Liposome Technology, Vols. I to III (2nd ed. 1993), the contents of which are incorporated herein by reference in their entirety), microparticles, microcapsules, recombinant cells, receptor-mediated endocytosis (see, e.g., Wu and Wu, J. Biol. Chem. 262:4429-4432 (1987)), construction of a nucleic acid as part of a retroviral or other vector, etc. Liposomes can consist of phospholipids or other lipids, and can be nontoxic, physiologically acceptable and metabolizable carriers that are relatively simple to make and administer.

Generally, the ingredients of the compositions may be supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the invention also provides that one or more of the pharmaceutical compositions is packaged in a hermetically sealed container such as an ampoule or sachette indicating the quantity of the IKKε inhibitor. In one embodiment, one or more of the IKKε inhibitor and/or pharmaceutical compositions is supplied as a dry sterilized lyophilized powder or water free concentrate in a hermetically sealed container and can be reconstituted (e.g., with water or saline) to the appropriate concentration for administration to a subject. In one embodiment, one or more of the IKKε inhibitor or pharmaceutical compositions is supplied as a dry sterile lyophilized powder in a hermetically sealed container at a unit dosage of at least 5 mg, for example at least 10 mg, at least 15 mg, at least 25 mg, at least 35 mg, at least 45 mg, at least 50 mg, at least 75 mg, or at least 100 mg. The IKKε inhibitor or pharmaceutical compositions may be stored at between 2° C. and 8° C. in its original container. The IKKε inhibitor or pharmaceutical compositions may be administered within 1 week, for example within 5 days, within 72 hours, within 48 hours, within 24 hours, within 12 hours, within 6 hours, within 5 hours, within 3 hours, or within 1 hour after being reconstituted. In an alternative embodiment, one or more of the IKKε inhibitor or pharmaceutical compositions is supplied in liquid form in a hermetically sealed container indicating the quantity and concentration of IKKε inhibitor. In a further embodiment, the liquid form of the administered composition is supplied in a hermetically sealed container at least 0.25 mg/mL, for example at least 0.5 mg/mL, at least 1 mg/mL, at least 2.5 mg/mL, at least 5 mg/mL, at least 8 mg/mL, at least 10 mg/mL, at least 15 mg/mL, at least 25 mg/mL, at least 50 mg/mL, at least 75 mg/mL or at least 100 mg/mL. The liquid form may be stored at between 2° C. and 8° C. in its original container.

The pharmaceutical compositions may include a "therapeutically effective amount" or a "prophylactically effective amount" of an IKKε inhibitor. A "therapeutically effective amount" refers to an amount effective, at dosages and for periods of time necessary, to achieve the desired therapeutic result. Amounts effective for this use will depend on, e.g., the particular composition of the IKKε inhibitor regimen administered, the manner of administration, the stage and severity of the disease, the general state of health of the patient, and the judgment of the prescribing physician. A therapeutically effective amount of the IKKε inhibitor may be determined by a person skilled in the art and may vary according to factors such as the disease state, age, sex, and weight of the individual, and the ability of the IKKε inhibitor to elicit a desired response in the individual. A therapeutically effective amount is also one in which toxic or detrimental effects, if any, of the IKKε inhibitor are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated, each unit containing a predetermined quantity of active compound calculated to produce the desired therapeutic effect in association with the required pharmaceutical carrier. The specification for the dosage unit forms are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an IKKε inhibitor may be a dose of between 0.1 and 200 mg/kg, for example between 0.1 and 10 mg/kg. The therapeutically or prophylactically effective amount of the IKKε inhibitor may be between 1 and 200 mg/kg, 10 and 200 mg/kg, 20 and 200 mg/kg, 50 and 200 mg/kg, 75 and 200 mg/kg, 100 and 200 mg/kg, 150 and 200 mg/kg, 50 and 100 mg/kg, 5 and 10 mg/kg, or 1 and 10 mg/kg. It is to be noted that dosage values may vary with the type and severity of the condition to be alleviated. Further, the IKKε inhibitor dose may be determined by a person skilled in the art and may vary according to factors such as the disease state, age, sex, and weight of the individual, and the ability of the IKKε inhibitor to elicit a desired response in the individual. The dose is also one in which toxic or detrimental effects, if any, of the IKKε inhibitor are outweighed by the therapeutically beneficial effects. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

6. ADMINISTRATION

The IKKε inhibitor as detailed above can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular subject, and the route of administration.

The IKKε inhibitor can be administered by methods well known in the art as described in Donnelly et al. (*Ann. Rev. Immunol.* 1997, 15, 617-648); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The IKKε inhibitor can be complexed to particles or beads that can be administered to an individual, for example, using a vaccine gun. One skilled in the art would know that the choice of a pharmaceutically acceptable carrier, including a physiologically acceptable compound, depends, for example, on the route of administration.

The IKKε inhibitor can be delivered via a variety of routes. Typical delivery routes include parenteral administration, e.g., intradermal, intramuscular or subcutaneous delivery. Other routes include oral administration, intranasal, intravaginal, transdermal, intravenous, and epidermal routes.

The IKKε inhibitor can be administered via electroporation, such as by a method described in U.S. Pat. No. 7,664,545, the contents of which are incorporated herein by reference. The electroporation can be by a method and/or apparatus described in U.S. Pat. Nos. 6,302,874; 5,676,646; 6,241,701; 6,233,482; 6,216,034; 6,208,893; 6,192,270; 6,181,964; 6,150,148; 6,120,493; 6,096,020; 6,068,650; and 5,702,359, the contents of which are incorporated herein by reference in their entirety. The electroporation can be carried out via a minimally invasive device.

In a specific embodiment, where the composition is a nucleic acid encoding a shRNA, for example, the nucleic acid can be administered in vivo by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, Proc. Natl. Acad. Sci. USA 88:1864-1868). Alternatively, a nucleic acid can be introduced intracellularly and incorporated within host cell DNA for expression by homologous recombination.

7. EXAMPLES

The foregoing may be better understood by reference to the following examples, which are presented for purposes of illustration and are not intended to limit the scope of the invention.

Example 1

Methods and Materials

Antibodies and Reagents.

Commercially available antibodies used for this study include rabbit polyclonal GFP antibody (sc-8334) and GST antibody (sc-459) (Santa Cruz Biotechnology, Inc., Dallas, Tex.), rabbit polyclonal IKKε antibody (14907) and FLAG M2 monoclonal antibody (Sigma-Aldrich, St. Louis, Mo.), Mouse monoclonal β-actin antibody (Abcam, Cambridge, England), PE rat anti-human IL-2, PE rat anti-mouse IFN-γ, APC Rat anti-mouse CD8α, PE hamster anti-mouse CD3ε and FITC rat anti-mouse CD4 (BD Pharmingen, San Diego, Calif.), rabbit polyclonal Iba1 antibody (PA5-27436) (Thermo Fisher Scientific, Waltham, Mass.), and rabbit monoclonal CD3 antibody (ab16669) (Abcam, Cambridge, England). Rabbit p-NFAT2 antibody was kindly provided by Dr. Chi-Wing Chow (Albert Einstein College of Medicine) and Dr. Roger Davis (University of Massachusetts Medical School) (Chow et al. *Mol. Cell Biol.* 2000, 20, 5227). Major histocompatibility complex (MHC)/peptide tetramers for γHV68 ORF61 524-531/Kb (TSINFVKI, SEQ ID NO: 17) and influenza virus NP 366-374/Db (ASNENMETM, SEQ ID NO:18) conjugated to PE were obtained from the NIH Tetramer Core Facility (Emory University, Atlanta, Ga.).

PMA (P1585), ionomycin (10634) and Brefeldin A (B7651) were purchased from Sigma-Aldrich (St. Louis, Mo.), cyclosporin A (9973) from Cell Signaling Technologies (Danvers, Mass.), and amlexanox (4857) from Tocris Bioscience (Bristol, UK).

Viruses, Mouse and Viral Infections.

Influenza A virus PR8 (A/PR8/H1N1) was kindly provided by Dr. Jae Jung (University of Southern California) (Amini-Bavil-Olyaee et al. *Cell Host Microbe* 2003, 13, 452). γHV68 were propagated in BHK21 cells as described previously (Dong et al. *PLoS Pathog.* 2010, 6, e1001001). IKKε knockout mice were purchased from Jackson Laboratory (Harvard University) (Tenoever et al. *Science* 2007, 315, 1274). Eight to ten week old, gender matched mice were used for infection. All animal work was performed under strict accordance with the recommendations in the Guide for the Care and Use of Laboratory Animals of the National Institutes of Health. The protocol was approved by the Institutional Animal Care and Use Committee (IACUC) of the University of Southern California. For influenza virus infection, mice were anesthetized by intraperitoneal injection of 1.5 mg of ketamine/0.12 mg of xylazine and inoculated intranasally with 1000 PFU of PR8 influenza virus. For γHV68 infection, mice were intraperitoneally infected with $10^6$ PFU of virus in 150 μL of phosphate buffered saline.

RNA extraction, RT-PCR, and qRT-PCR.

Jurkat T cells were stimulated with 10 ng/mL of PMA, 0.5 mM of ionomycin, and 2 mM of $CaCl_2$ for 5 h. IKKε WT or knockout T cells were purified with a pan T cell isolation kit II (Miltenyi Biotec). Purified T cells were mock treated or treated with 5 ng/mL of PMA and 0.2 mM of ionomycin for 5 hours. Cells were harvested, washed with cold PBS, and total RNA was extracted. Extracted RNA was treated with DNase I (New England Biolabs) to remove genomic DNA. One g of total RNA was used for reverse transcription with Superscript II reverse transcriptase (Invitrogen) according to the manufacturer's instructions. Approximately 0.5% of the cDNA was taken as template in each quantitative real-time PCR (qRT-PCR) reaction with SYBR master mix.

Q-PCR Primers in IL-2 Quantification:

```
Mouse β-Actin:
                                    (SEQ ID NO: 3)
TCTACGAGGGCTATGCTCTCC
and

                                    (SEQ ID NO: 4)
TCTTTGATGTCACGCACGATTTC;

Mouse IL-2:
                                    (SEQ ID NO: 5)
CCTGAGCAGGATGGAGAATTACA
and

                                    (SEQ ID NO: 6)
TCCAGAACATGCCGCAGAG;

Human β-Actin:
                                    (SEQ ID NO: 7)
GCACAGAGCCTCGCCTT
and

                                    (SEQ ID NO: 8)
GTTGTCGACGACGAGCG;

Human IL-2:
                                    (SEQ ID NO: 9)
AACTCACCAGGATGCTCACATTTA
and

                                   (SEQ ID NO: 10)
TCCCTGGGTCTTAAGTGAAAGTTT.
```

γHV68 genome copy number was measured by qRT-PCR as described previously (Chow et al. *Mol. Cell Biol.* 2000, 20, 5227). Briefly DNA was extracted from viral infected spleen and subjected to qRT-PCR analysis.

q-PCR Primers Used in Viral Genome Copy Number Detection:

```
ORF57:
                                   (SEQ ID NO: 11)
CCGACTACACGCAACACAAC
and

                                   (SEQ ID NO: 12)
AAATAACCTGGGTGCTGTCAC

RTA:
                                   (SEQ ID NO: 13)
TTTATCAGCACGCCATCAAC
and

                                   (SEQ ID NO: 14)
TGCGGAACAGGTGTGATTATC

β-Actin:
                                   (SEQ ID NO: 15)
CAGGCATTGTGATGGACTCC
and

                                   (SEQ ID NO: 16)
CAAGAAGGAAGGCTGGAAAAG
```

Luciferase Reporter Assay.

HEK293T cells in 24-well plates were transfected with a reporter plasmid mixture that contained 50 ng of the plasmid expressing firefly luciferase under the control of NFAT transcription factor and 100 ng of the plasmid expressing β-galactosidase. At 30 h post-transfection, cells were harvested and centrifuged. Cell lysates were used for luciferase and β-galactosidase assays according to the manufacturer's instruction (Promega).

Immunofluorescence.

293T cells were transfected with plasmids containing EGFP-NFAT2 and IKKε or IKKεK38A. At 24 h post-transfection, cells were treated with 1 μM of ionomycin for 1 h, fixed with 4% paraformaldehyde, and permeabilized with 1% Triton X-100. After staining with primary antibody (FLAG M2 antibody) and secondary antibody (Alexa 568-conjugated goat anti-mouse antibody), cells were analyzed with a Nikon E800M microscope.

Stable Cell Line Generation.

Lentivirus production was carried out in 293T cells as described previously (Feng et al (2008) PLoS Pathog 4, e1000157). Jurkat T cells were infected with lentivirus containing the indicated shRNA, NFAT2 or mutant, IKKε or IKKεK38A, selected with 1 μg/mL of puromycin.

The IKKε shRNA Sequence:

```
77:
                                                  (SEQ ID NO: 1)
CCGGCTGGACGATGATGAGAAGTTTCTCGAGAAACTTCTCATCATCGT

CCAGTTTTT

78:
                                                  (SEQ ID NO: 2)
CCGGAGAAGTTCGTCTCGGTCTATGCTCGAGCATAGACCGAGACGAAC

TTCTTTTTG
```

Intracellular Staining.

For IL-2 staining, Jurkat cells were stimulated with 10 ng/mL of PMA, 0.5 mM of ionomycin and 2 mM $CaCl_2$ for 3 hours. Brefeldin A (2 mg/mL) was added and incubation was extended for additional two hours. Cells were harvested and used for IL-2 staining with Cell Fixation/Permeabilization Kits (BD Biosciences) following the manufacturer's instruction.

For mouse IFNγ staining, freshly isolated splenocytes from γHV68-infected WT and Ikbke−/− mice were stimulated with 10 mg/mL TSINFVKI (SEQ ID NO: 17) peptide for 4 h. Brefeldin A (2 mg/mL) was added and incubation was extended for another two hours. Cells were fixed and permeabilized for intracellular IFNγ staining.

Tetramer Staining.

Influenza virus infected mice were sacrificed at 8 days post infection and bronchoalveolar lavage (BAL) was collected by flushing the lung with 1 mL of PBS twice. Cells in BAL were spin down and subjected to tetramer staining. γHV68-infected mice were sacrificed at 6, 10, 13, and 2 days post-infection (dpi) and the spleen was collected. Single cell suspension was generated by passing through 40-mM strainer on ice. Red blood cells were removed by adding 5 mL of Pharm Lysis buffer (BD Biosciences, San Jose, Calif.). Cells were washed once with cold PBS plus 1% FBS and subjected to tetramer staining.

Tetramer staining was carried out as previously described (Molloy et al. *J. Immunol.* 2011, 186, 6218). Briefly, cells were incubated with anti-CD16/32 antibody for 10 min on ice followed by stained for 1 hour in the dark with tetramers. Cells were then stained with CD8 antibody for 20 min on ice. Samples were analyzed by using FACSCalibur and data were analyzed with FlowJo software.

In Vivo Killing Assay.

RBC-lysed, single-cell spleen suspensions from $Ikbke^{+/+}$ or $Ikbke^{-/-}$ mice were pulsed with or without 2 μg/mL viral peptide for one hour at 37° C. Splenocytes were labeled with high (10 μM) or low (1 μM) concentration of CFSE at 37° C. for 15 min. Cells were spin down and incubated with fresh medium at 37° C. for 30 min. Cells ($10^7$) labeled with high concentration of CFSE and pulsed with peptide were mixed with equal number of cells labeled with low concentration of CFSE and injected intravenously into $Ikbke^{+/+}$ or $Ikbke^{-/-}$ mice infected with γHV68 for 13 days. At 16 hours post-injection, single-cell suspension of splenocytes was prepared and analyzed by flow cytometry.

Limiting-Dilution Nested PCR (LD-PCR) Detection of γHV68 Genome-Positive Cells.

The frequency of splenocytes harboring γHV68 genome was measured by LD-PCR as previously described (Dong et al. *PLoS Pathog.* 2010, 6, e1001001). Briefly, mouse spleens were homogenized, re-suspended in isotonic buffer, and subjected to 3-fold serial dilutions in a background of uninfected RAW 264.7 cells, with a total of $10^4$ cells per well. Twelve replicates were plated for each cell dilution. After being plated, cells were subjected to lysis by proteinase K at 56° C. for 8 hours. Following inactivating the enzyme for 30 minutes at 85° C., samples were subjected to nested PCR using primers specific for γHV68 ORF72. Reaction products were separated using 2.5% UltraPure agarose (Invitrogen) gels and visualized by ethidium bromide staining.

Immunohistochemistry.

Mouse tissue samples were fixed in the 10% (vol/vol) formalin solution (Sigma) overnight. Tissue specimens were dehydrated, embedded in paraffin, and cut into 3-μm sections. Tissue sections were analyzed by H&E and immunohistochemistry staining with antibodies against CD3 or Iba1, and DAB substrate kit (Vector Laboratories). Images were visualized with a Nikon E800M microscope equipped with a Nikon DXM1200 digital camera and the Nikon ACT-1 imaging software system.

In Vitro Kinase Assay.

In vitro IKKε kinase assays were performed. HEK293T cells were transiently transfected with IKKε, harvested and lysed with kinase lysis buffer [20 mM Tris (pH 7.4), 150 mM NaCl, 10% (vol/vol) glycerol, 0.5% Triton X-100, and 0.5 mM DTT], and lysates were precipitated with 10 μL of anti-Flag M2-conjugated agarose (Sigma). After extensive washing with kinase lysis buffer and final washing with kinase reaction buffer (1 mM DTT, 5 mM KCl, 2 mM $MgCl_2$, 2 mM $MnCl_2$, 10 mM NaF, and 25 mM Hepes, pH 7.5), precipitated IKKε was eluted with FLAG peptide (100 μg/mL) and used to phosphorylate selected substrates in vitro. Reaction mixtures containing 0.5 μg of indicated substrate proteins and 10 μCi of [$γ^{32}$P]-ATP in 30 μL of total volume were incubated for 30 min at 25° C. Reactions were stopped with SDS/PAGE sample buffer by boiling for 5 min at 100° C., and samples were resolved by SDS/PAGE, transferred to PVDF membrane, and analyzed by autoradiography.

To test IKKε and protein kinase A (PKA) to prime for GSK3β3, 0.5 μg of GST-SP2 and SP3 bound to glutathione-sepharose beads were incubated with 1 U of recombinant PKA (New England Biolabs) or 50 ng of IKKε in the presence of 1 mM ATP for 1 h at 25° C. The beads were washed extensively and then incubated with 50 ng of GSK3β in a volume of 30 μl containing 10 μCi of [$γ^{32}$P]-ATP for 30 min at 25° C.

Determining γHV68-Specific Antibody.

γHV68 specific antibody detection was adopted from a previous protocol (Hughes et al. (2010) J Virol 84:3949). γHV68 was purified by ultracentrifuge at 32000 rpm for 2.5 h and concentrated viral particles were coated to ELISA plates at 4° C. overnight. Plates were then washed five times with PBS-Tween (0.01%) and blocked with 10% normal goat serum for 1 h at 37° C. Two fold dilutions of sera, starting with an initial dilution of 1:20 in PBST were added to the wells of the plates and incubated at 37° C. for 1 h. After washing rabbit anti-mouse immunoglobulin conjugated to horseradish peroxidase (HRP) diluted at 1:2,000 was added to the plate and incubated for 1 h at room temperature. γHV68-specific antibody was detected by adding TMB substrate (BD biosciences), and the absorbance was measured at 450 nm. Antibody levels were expressed as the reciprocal dilution at which the sample became negative. At each time point, 4 to 5 mouse sera were measured and the results were showed as the mean value and standard deviations.

Cytokine Measurement.

BAL fluid collected from influenza virus (PR8)-infected mice was used to determine the cytokine level. The spleen of γHV68-infected mice was collected and homogenized in 1 mL of DMEM and centrifuged supernatant was subjected to cytokine measurement. ELISA kits for murine CCL5 (R&D systems) and IL-6 ELISA (BD Biosciences) were used according to the manufacturer's instructions.

Example 2

IKKε Inhibits NFAT Activation in a Kinase-Dependent Manner

Figure 5:
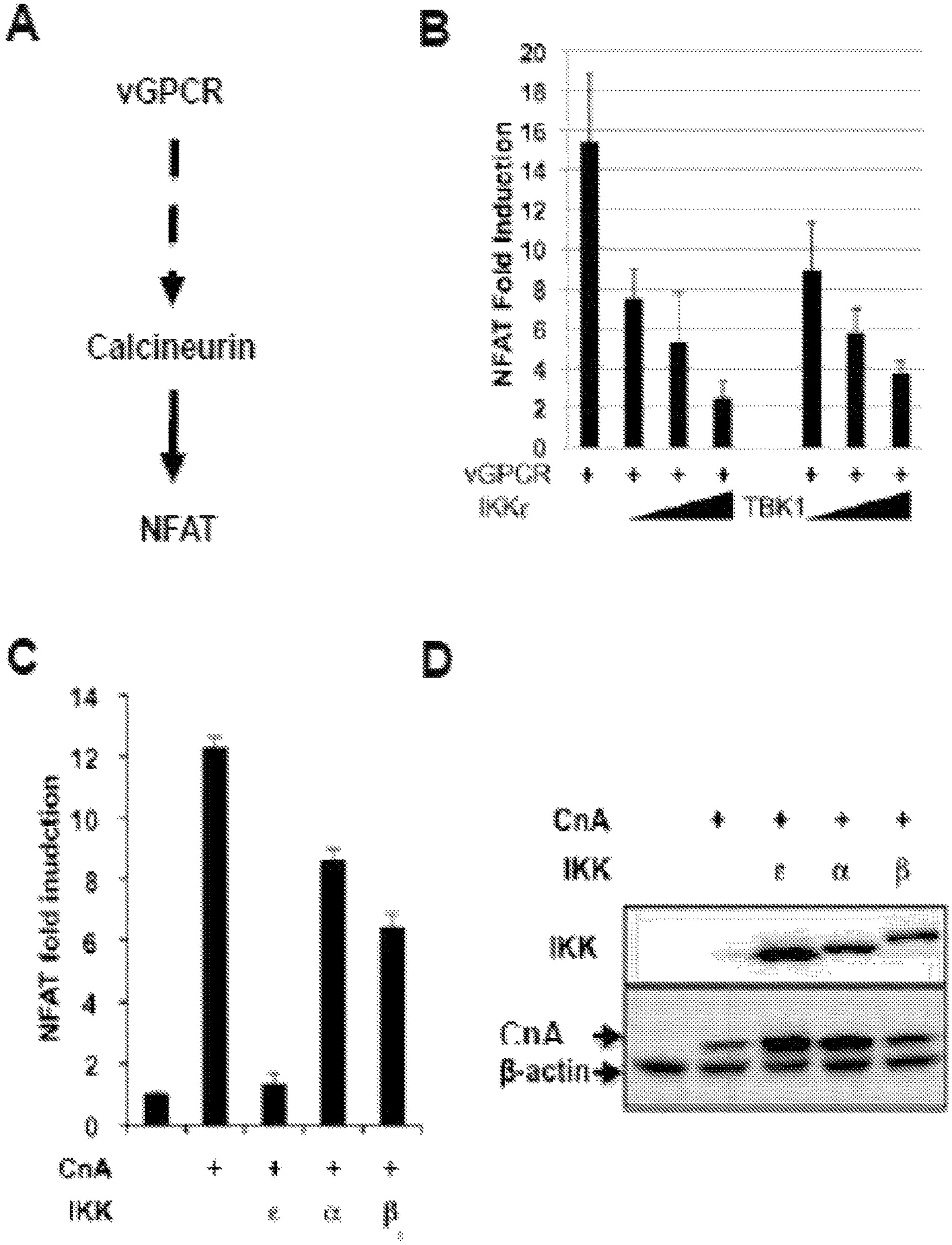
FIG. 5 shows that IKKε inhibits NFAT activation. (A) Sketched diagram of signal transduction of NFAT activation by GPCR. (B) 293T cells were transfected with an NFAT reporter plasmid cocktail, a plasmid containing vGPCR, and increasing amount of plasmids containing IKKε or TBK-1. NFAT activation was determined by luciferase reporter assay. (C and D) Transfection of 293T and NFAT activation were carried out in (B) except that plasmids containing IKKα and IKKβ were used (C). Whole cell lysates were analyzed by immunoblotting with indicated antibodies (D).

IKKε is involved in tumor formation induced by a viral G protein-coupled receptor (vGPCR) via activating NFκB. Interestingly, vGPCR can potently activate NFAT (FIG. 5A).

To explore the role of IKKε in vGPCR-induced NFAT activation, NFAT reporter assays were performed. IKKε potently inhibited vGPCR-induced NFAT activation in a dose-dependent manner (FIG. 5B). The closely-related TBK1 similarly inhibited NFAT, albeit to a lesser extent. To probe the point of inhibition of IKKε in the signaling cascade, NFAT2 and its immediately upstream calcineurin phosphatase were over-expressed and NFAT activation was determined. Strikingly, IKKε expression was sufficient to diminish NFAT activation triggered by both molecules (FIGS. 1A and 1B), suggesting that IKKε acts on NFAT transcription factors. Moreover, IKKε was as potent as DYRK2 in diminishing NFAT activation induced by NFAT2 (FIG. 1C). IKKα and IKKβ, however, weakly inhibited calcineurin-induced NFAT activation (FIGS. 5C and 5D), prompting further study of dampening NFAT activation. To test whether the kinase activity of IKKε is involved in the inhibition of NFAT activation, NFAT reporter assays were performed using the kinase-dead IKKεK38A. In stark contrast to IKKε, IKKεK38A failed to inhibit calcineurin-induced NFAT activation (FIG. 1D). Expression of IKKε, but not that of IKKεK38A, abrogated the nuclear translocation of GFP-NFAT2 reporter upon treatment with ionomycin (FIG. 1E). Semi-quantitative analysis showed that IKKε expression completely precluded NFAT nuclear localized induced by ionomycin, while IKKεK38A had no detectable effect (FIG. 1F). Collectively, these results indicated that IKKε potently inhibits NFAT activation in a kinase-dependent manner.

Example 3

IKKε Phosphorylates NFAT Via Direct and Indirect Mechanisms

Figure 2:
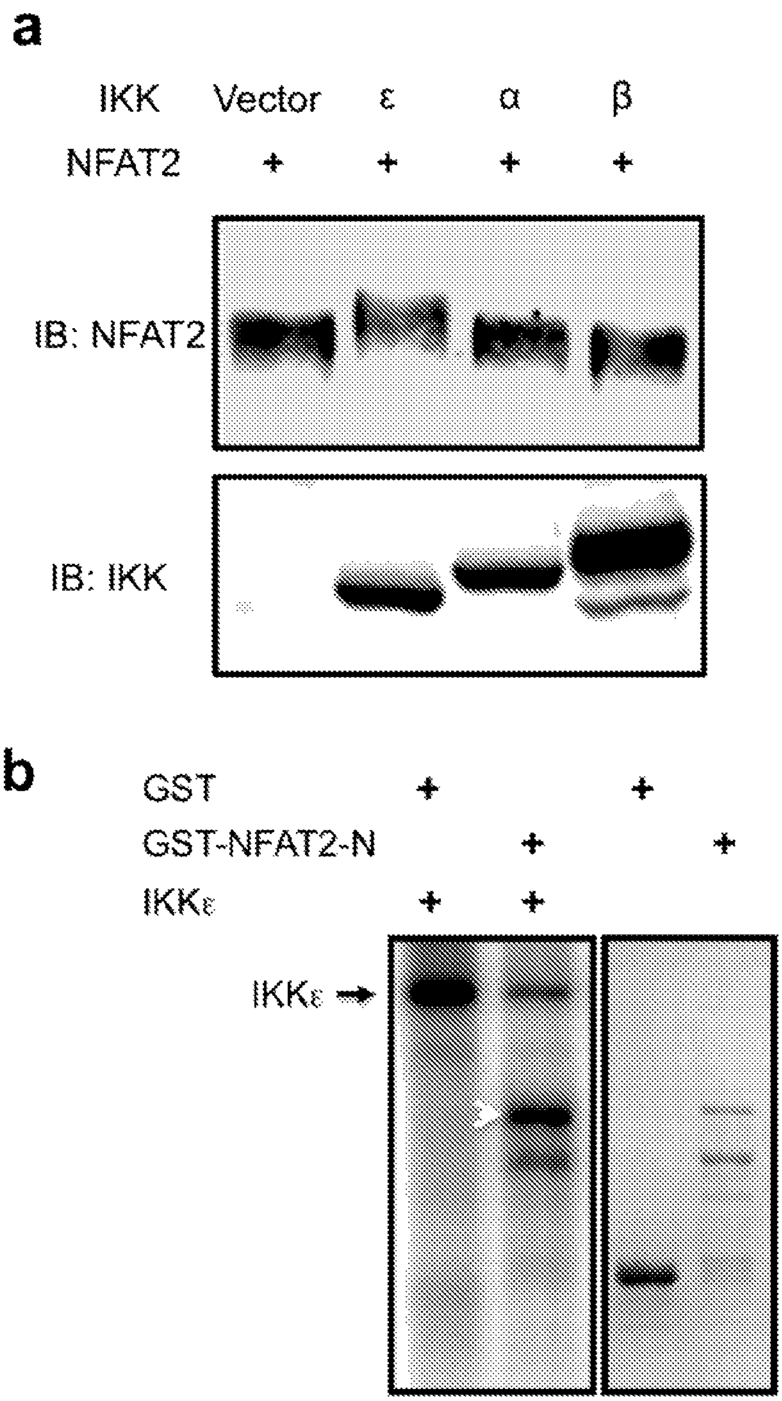
FIG. 2 shows that IKKε phosphorylates NFAT2. (A) 293T cells were transfected with plasmids containing EGFP-NFAT2 and indicated IKK. Whole cell lysates were analyzed by immunoblotting with indicated antibodies. (B) IKKε purified from 293T cells was incubated with GST fusion proteins containing the N-terminal regulatory domain (amino acids 1-319), [$^{32}$P]γATP and was analyzed by autoradiography (left panel) or coomassie staining (right panel). (C) Summary of the IKKε phosphorylation sites, within the N-terminal regulatory domain, identified by mass spectrometry, showing peptides of SEQ ID NOs: 19-20 and 30-32. (D) 293T cells were transfected with plasmids containing indicated genes. NFAT2 was precipitated with anti-Flag antibody and, along with whole cell lysates (WCL), analyzed by immunoblotting. (E) 293T cells were transfected with plasmids containing indicated genes and whole cell lysates were analyzed by immunoblotting. (F) NFAT activation in 293T cells by NFAT2-4A mutant was determined by luciferase assay. (G) Jurkat T cells were infected with control lentivirus or lentivirus containing wild-type NFAT2 or NFAT2-4A mutant. NFAT2 was precipitated and analyzed by immunoblotting (top). After stimulation with phorbol 12-myristate 13-acetate (PMA) and ionomycin, Jurkat T cells were analyzed by IL-2 intracellular staining (bottom).
Figure 2:
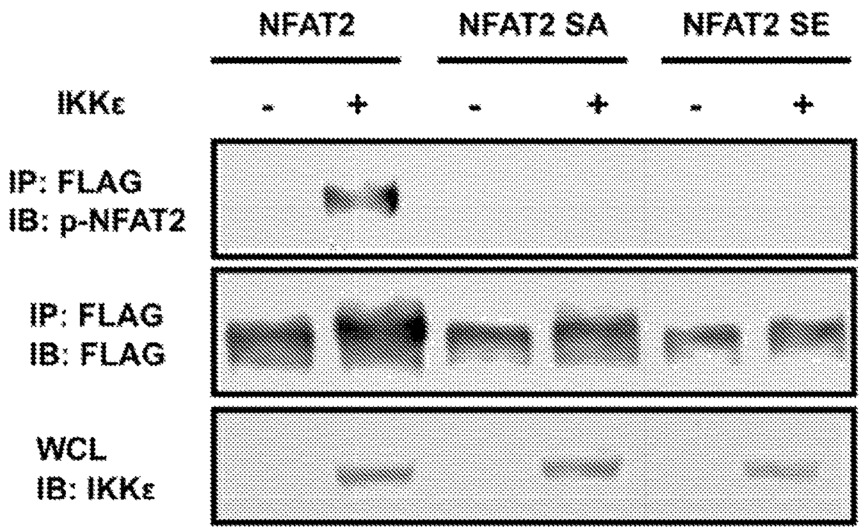
Figure 2:
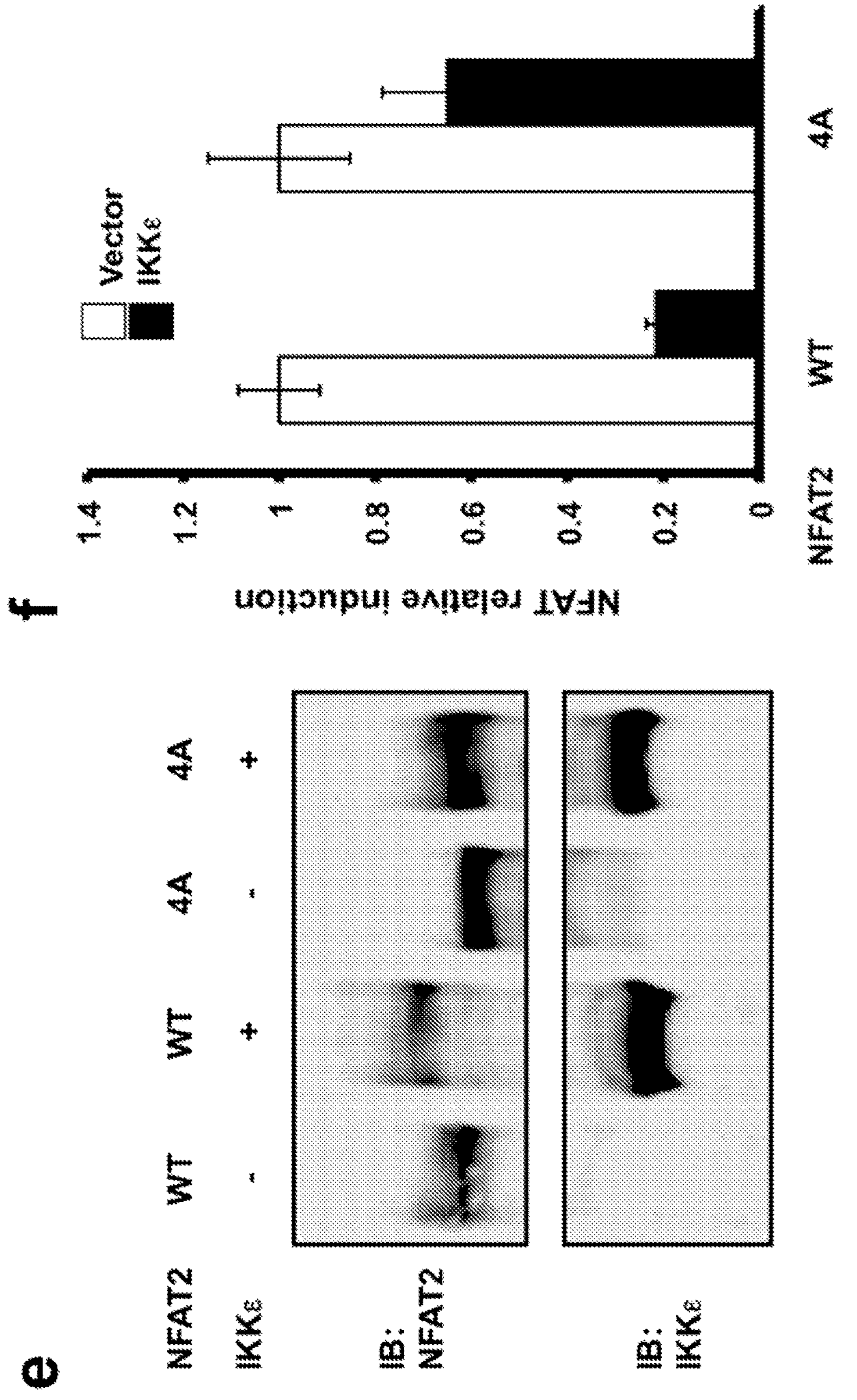
Figure 2:
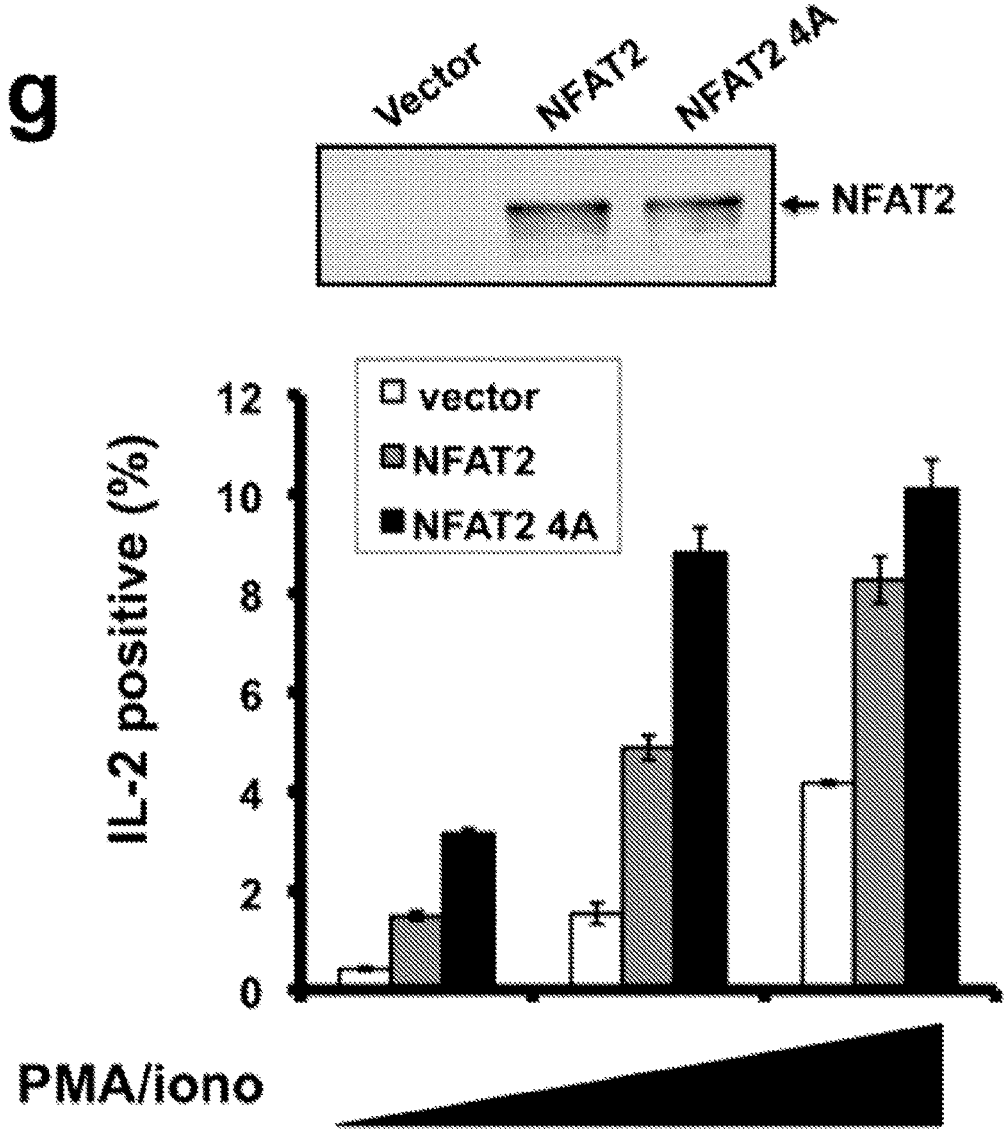
Figure 6:
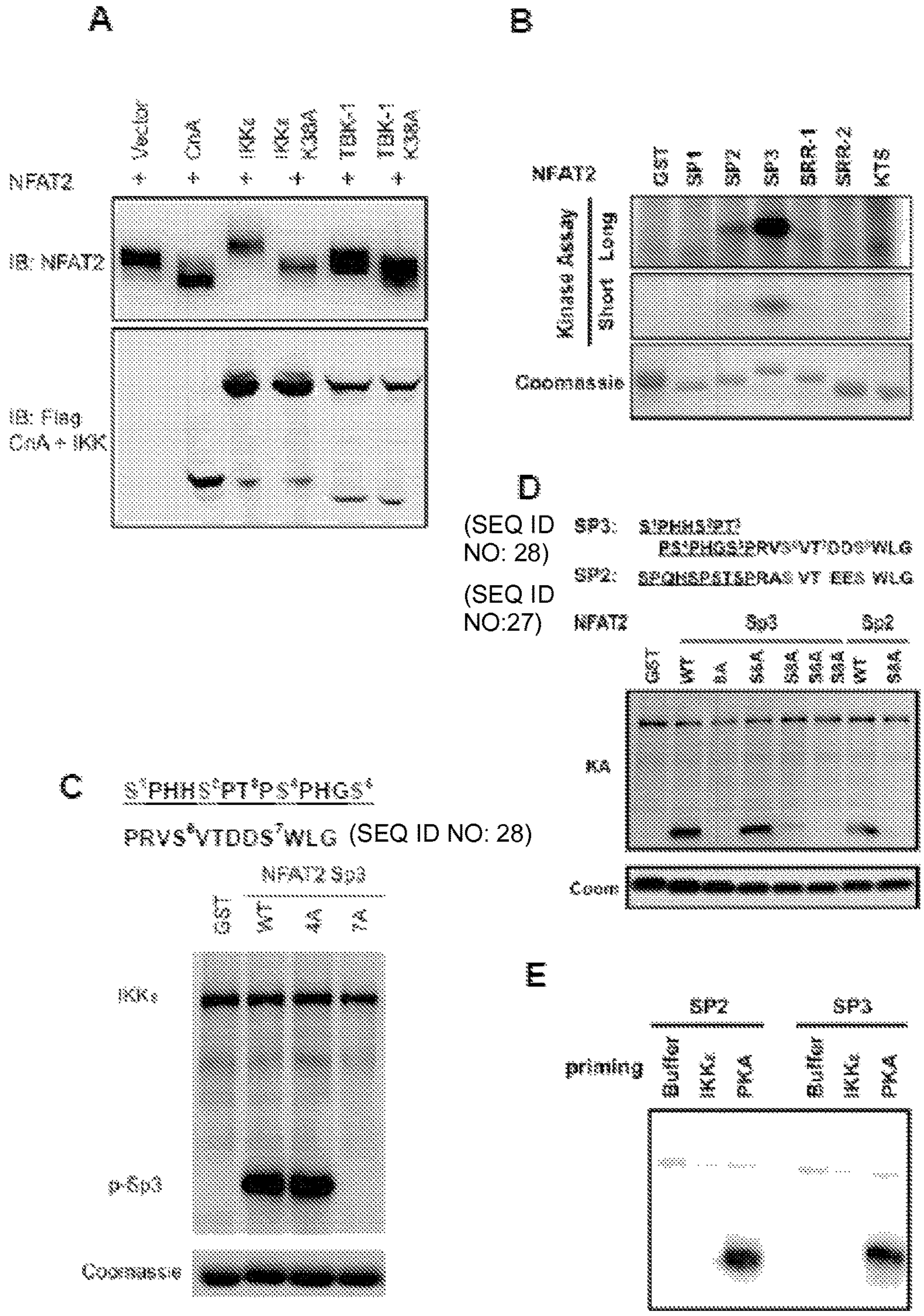
FIG. 6 shows that IKKε phosphorylates NFAT. (A) 293T cells were transfected with plasmids containing indicated genes and whole cell lysates were analyzed by immunoblotting with indicated antibodies. (B) Purified GST fusion containing the indicated domain were incubated with IKKε with [$^{32}$P]γATP. The products were analyzed by autoradiography. (C) SP3 peptides of wild-type, 4A or 7A mutants were analyzed by an in vitro kinase assay. Reactions were analyzed by autoradiography (middle) and coomassie staining (bottom). Top panel shows the wild-type SP3 sequence with the classic four SP sites (Ser in red) that were replaced with alanine (4A mutant) or with all seven serines (denoted with superscript 1-7) (7A mutant). (D) GST fusion SP3 or SP2 peptide or the mutants were analyzed by in vitro kinase assay. (E) GST fusions containing the SP2 or SP3 peptide were first primed with IKKε or PKA with cold ATP, washed, and then phosphorylated with IKKε or GSK3β in the presence of [$^{32}$P]γATP. The products were analyzed by autoradiography.

NFAT activation is primarily regulated by dephosphorylation, and the kinase activity of IKKε is involved in its inhibition on NFAT activation. IKKε may directly phosphorylate NFAT. Expression of NFAT kinases often retards NFAT migration analyzed by electrophoresis. Indeed, expression of IKKε resulted in slowly migrating species of NFAT2 (FIG. 2A). Neither the expression of IKKα and IKKβ, nor that of the kinase-dead mutants of IKKε and TBK-1, was able to retard NFAT2 migration (FIG. 2A and FIG. 6A). Furthermore, purified IKKε was sufficient to phosphorylate the N-terminal regulatory domain (amino acids 1-319) of NFAT2 by an in vitro kinase assay (FIG. 2B). The N-terminal region of NFAT consists of multiple serine/threonine-rich sequences that can be phosphorylated by distinct kinases. By screening GST fusion proteins carrying known phosphorylation motifs, it was found that IKKε efficiently phosphorylated the SP3 motif and weakly the SP2 site, but not SP1, SRR1, SRR2, or KTS sequences (FIG. 6B). Further mutational analysis within SP2 and SP3 sites identified two new serine residues, but not those of the classical SP sequences, which served as phospho-acceptors (FIG. 6C). These two serine residues are embedded in a conserved motif, $S^{294}$VTDD(/EE)$S^{299}$WLG (SEQ ID NO: 19, SEQ ID NO:29), which is shared by four of the five human NFAT molecules (FIG. 6D). In vitro kinase assays indicated that the second serine residue was the primary phosphorylation site by IKKε. Given the close proximity of this IKKε phosphorylation site to the SP sequences, it was tested whether IKKε can prime for GSK3β-mediated phosphorylation of SP sites. Pre-phosphorylation of SP2 and SP3 by PKA led to robust phosphorylation by GSK3β, while IKKε failed to do so, indicating that IKKε cannot prime for GSK3β-mediated phosphorylation of SP sites (FIG. 6E).

Figure 7:
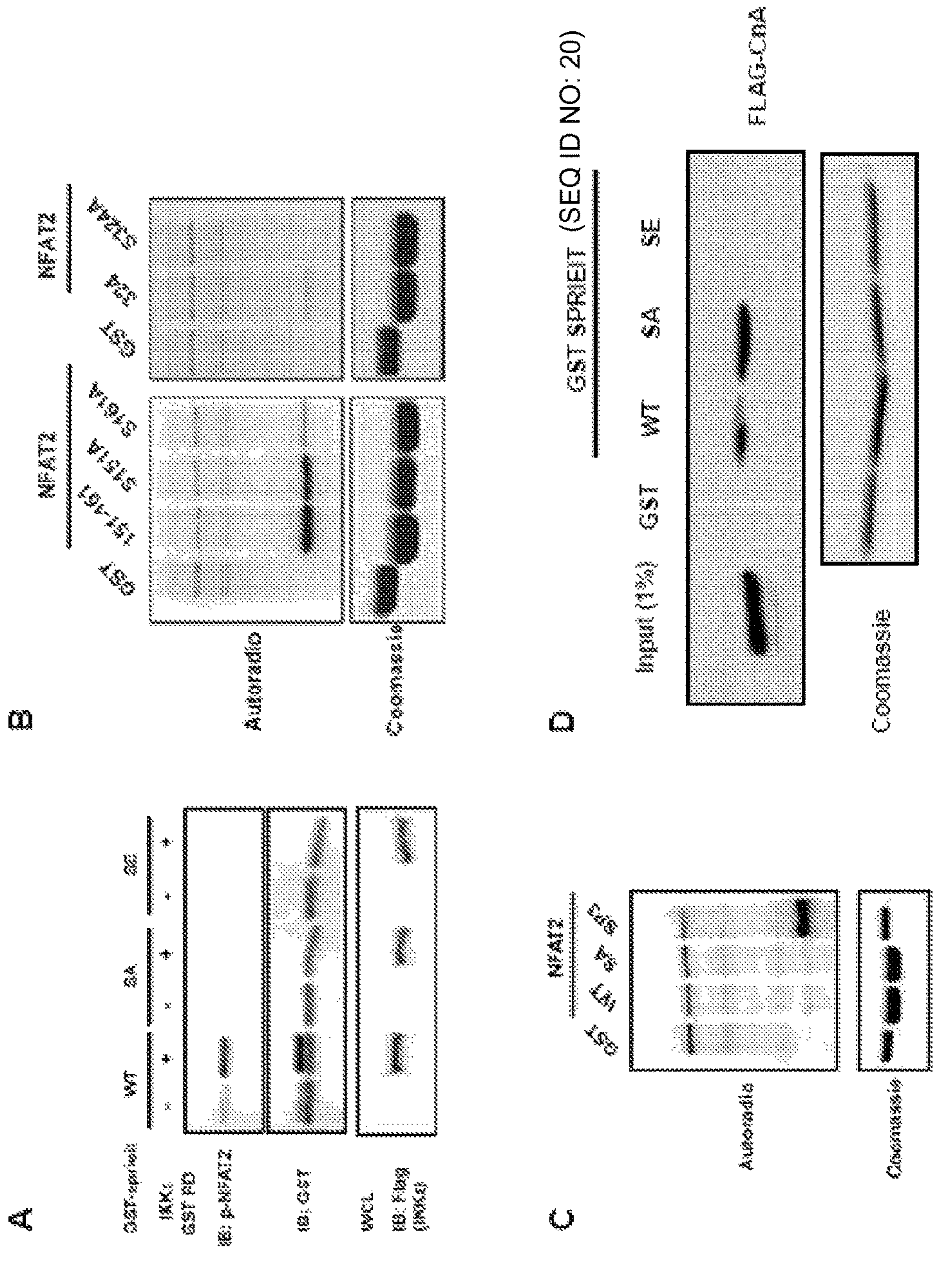
FIG. 7 shows characterization of the NFAT2 phosphorylation sites. (A) 293T cells were transfected with plasmids containing GST fusion proteins containing wild-type (WT), S>A (SA), or S>E (SE) mutants of the calcineurin-docking peptide derived from NFAT2, with or without IKKε. After pulldown with glutathione-Sepharose beads, the products were analyzed with the indicated antibodies. (B and C) In vitro kinase assay with purified IKKε and GST fusion proteins containing indicated phosphorylation sites flanked with 9-11 amino acids in (B) or those containing wild-type (WT) or S>A (SA) mutant of the calcineurin-docking peptide in (C). (D) Purified GST fusion proteins containing wild-type (WT), S>A (SA), or S>E (SE) mutants of the calcineurin-docking peptides bound to glutathione-Sepharose beads were incubated with FLAG-Calcineurin A (FLAG-CnA) expressed 293T cell lysate. After pull-down the bound protein were checked with FLAG antibody.

To delineate the IKKε phosphorylation sites within NFAT, NFAT2 was purified with or without IKKε expression in 293T cells, and serine/threonine phosphorylation was analyzed by mass spectrometry. Four predominant phosphorylation sites were identified within the N-terminal regulatory domain, in addition to 2 serine residues in the SP3 site, within the N-terminal regulatory domain (FIG. 2C). Phosphorylation frequency of the four sites was approximately doubled by IKKε expression. The phosphorylation of the two serine residues within the SP3 site was increased from a basal level of 20% and 5.7% to ~42% and 23%, respectively (FIG. 2C). Phosphorylation frequency of three sites ($S^{117}$, $S^{151}$, and $S^{324}$) was approximately doubled by IKKε expression, whereas that of $S^{161}$ was increased from the basal level of 13% to 76% with IKKε expression. Two serines ($S^{151}$ and $S^{161}$) preceded the SRR1 sequence, and one ($S^{324}$) was located immediately upstream of the KTR motif. $S^{117}$ of the calcineurin-docking site was previously shown to be phosphorylated by the Jun N-terminal kinase (JNK), thus reducing the calcineurin-binding ability of NFAT. Using an antibody specific for the phosphorylated $S^{117}$PRIEIT epitope (SEQ ID NO:20) (Bulek et al. *Nat. Immuno.* 2011, 12, 844), exogenous IKKε expression greatly elevated the phosphorylation of the calcineurin-docking site (FIG. 2D). Given the number of phosphorylation sites impacted by IKKε, it was tested whether IKKε can directly phosphorylate these motifs by an in vitro kinase assay. The results showed that peptides containing three serines, except the peptides containing $S^{117}$, were phosphorylated by IKKε in vitro (FIG. 7B). Interestingly, IKKε expression increased the phosphorylation of the calcineurin-docking site ($S^{117}$) in transfected cells (FIG. 7C). These findings suggest that other kinases, such as the aforementioned JNK, relay signal transduction from IKKε to NFAT via directly phosphorylating the calcineurin-docking site. Phosphorylation-mimetic mutation (S>E) diminished calcineurin-binding of the calcineurin-docking site by in vitro GST pull-down (FIG. 7D). These results collectively demonstrate that IKKε phosphorylates NFAT2 via direct and indirect mechanisms.

Example 4

Loss of IKKε Results in More Robust T Cell Response

Figure 8:
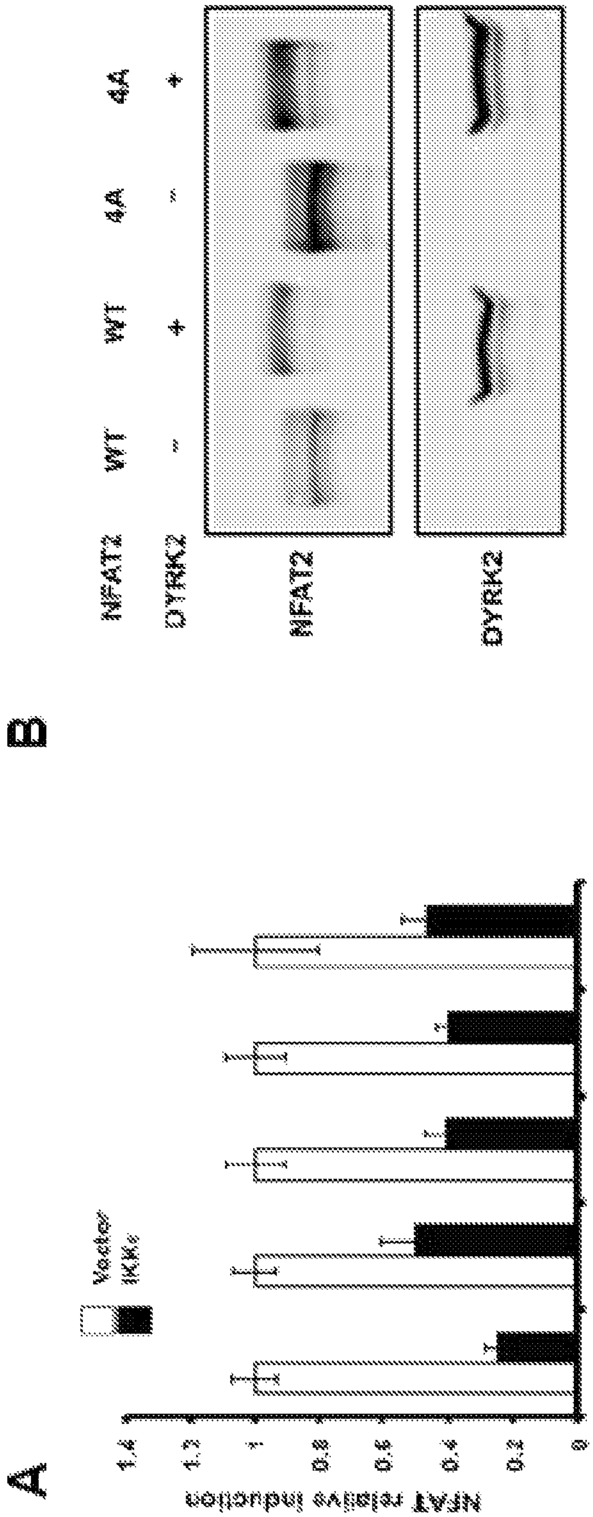
FIG. 8 shows characterization of phosphorylation-resistant mutants of NFAT2. (A) 293T cells were transfected with an NFAT reporter plasmid cocktail and plasmids containing indicated NFAT2 mutants, with or without a plasmid containing IKKε. NFAT activation was determined by luciferase assay. (B) 293T cells were transfected with plasmids containing wild-type NFAT2 or NFAT2 containing all four S>A (4A) mutations with or without DYRK2. The whole cell lysates were analyzed by immunoblotting with indicated antibodies.

To probe the functional consequence of these phosphorylation sites, NFAT2 mutants carrying S>A mutations were generated. Reporter assays showed that individual mutation of all four serines ($S^{117}$, $S^{151}$, $S^{161}$, $S^{324}$) within the N-terminal region conferred partial resistance to IKKε-mediated inhibition (FIG. 8A), whereas mutation of serines within the SP3 site had no detectable effect on NFAT activation with or without IKKε expression. The phosphorylation of the SP3 site by IKKε may assume other regulatory functions or operates redundantly with other modifications. Thus, the four prominent sites whose mutations demonstrated resistance to IKKε were further examined. When all four mutations were introduced into NFAT2, this mutant (designated NFAT2-4A) was resistant to IKKε-mediated inhibition of NFAT activation and to IKKε-mediated phosphorylation (FIGS. 2E and 2F). By contrast, DYRK2 expression retarded the migration of NFAT2-4A and wild-type NFAT2 to a similar degree (FIG. 8B). IKKε expression slightly retarded the migration of NFAT2-4A, implying that other minor IKKε phosphorylation sites exist in NFAT2. These results support the specific phosphorylation of NFAT2 within the N-terminal regulatory domain by IKKε. Next, NFAT2-4A and wild-type NFAT2 were expressed in Jurkat T cells, and IL-2 gene expression was determined. Upon stimulation with phorbol 12-myristate 13-acetate (PMA) and ionomycin, NFAT2-4A expression doubled the IL-2 positive cells that express wild-type NFAT2, while NFAT2 and NFAT2-4A were equally expressed (FIG. 2G). Taken together, these results indicated IKKε inhibits NFAT activation through increasing NFAT phosphorylation.

Example 5

IKKε Kinase Activity is Up-Regulated During T Cell Activation

Figure 14:
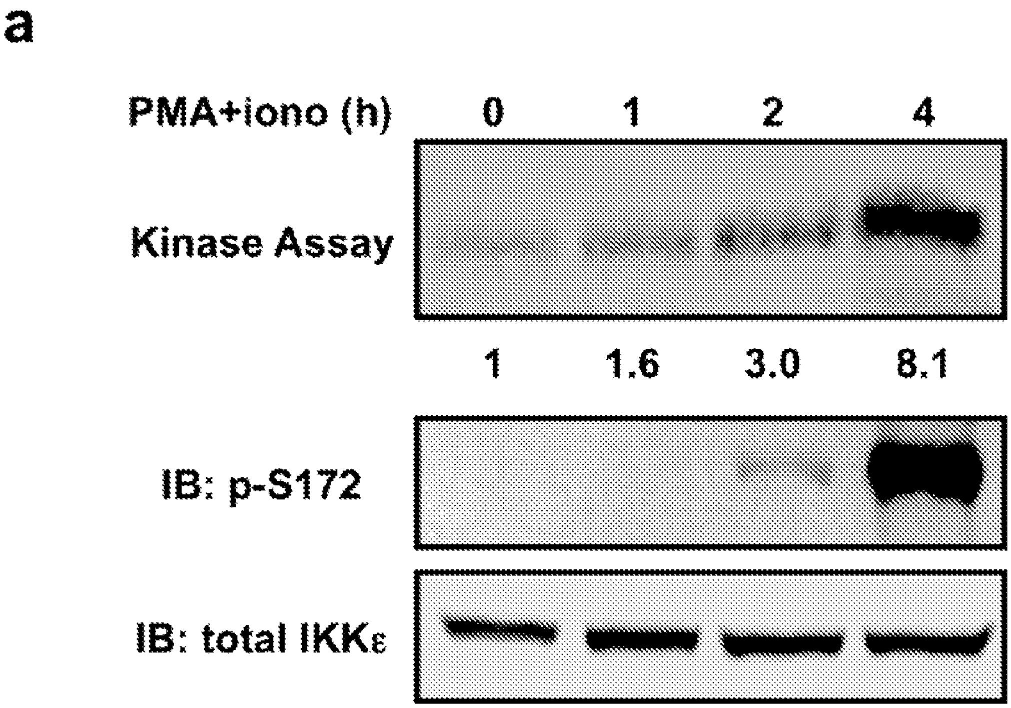
FIG. 14 shows that IKKε kinase is activated during T cell activation. (A) Human Jurkat T cells stably expressing Flag-IKKε were stimulated with PMA plus ionomycin. Precipitated IKKε was used for an in vitro kinase assay with GST fusion protein containing the N-terminal fragment of IκBα (amino acids 1-55), designated GST-IκBαN. Numbers indicate the relative intensity of phosphorylated GST-IκBαN. Precipitated IKKε was analyzed for the phosphorylation of $Ser^{172}$ (middle panel) and total IKKε (bottom panel). Data represents two independent experiments. (B) Human Jurkat T cells stably expressing Flag-NFAT2 were stimulated with vehicle (DMSO) or ionomycin, with or without an IKKε inhibitor (amlexanox, 50 μM) for two hours. Cells were harvested. NFAT2 was affinity purified and analyzed by mass spectrometry for quantitative measurement of phosphorylation of peptides containing $S^{117}$, $S^{151}$, $S^{161}$ and $S^{324}$ as indicated.
Figure 14:
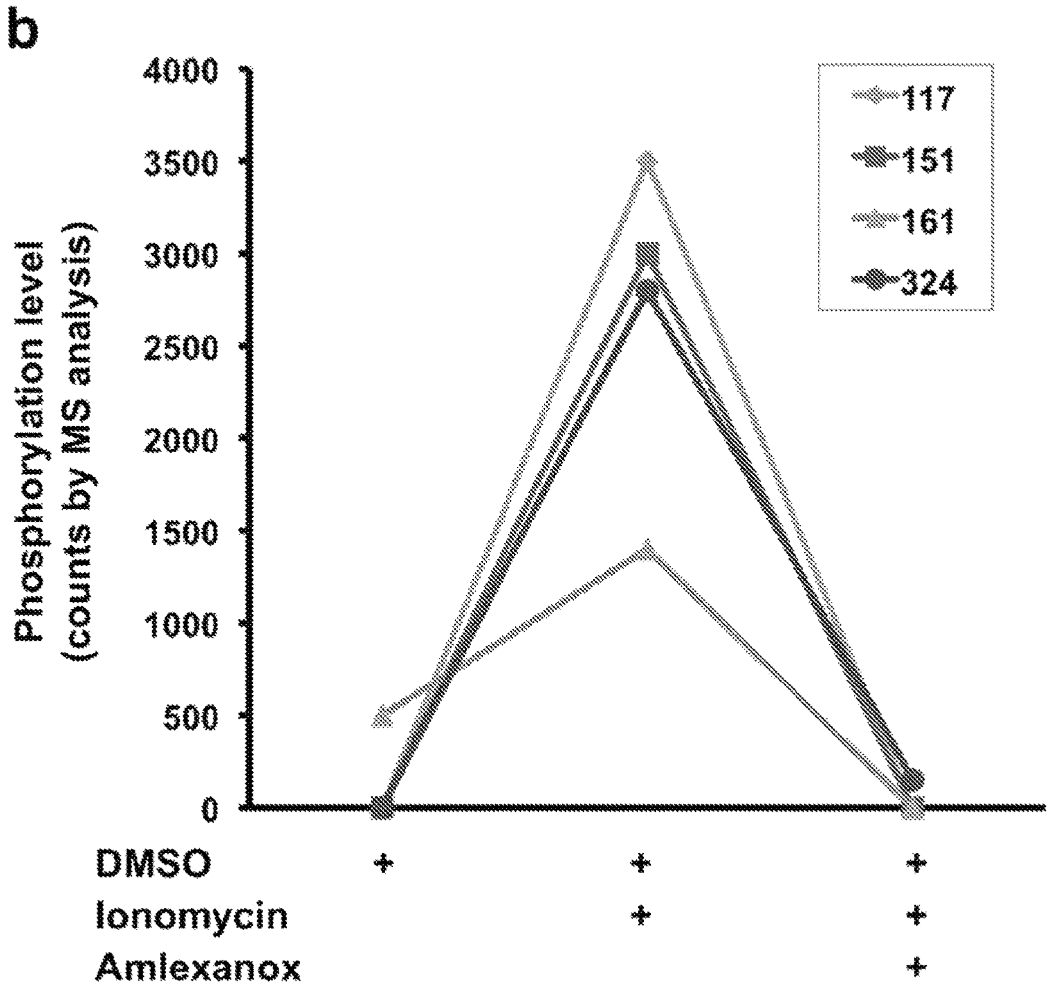

The inhibition of NFAT by IKKε may provide a negative feedback to T cell activation. IKKε kinase activity during T cell activation was assessed. First, the protein expression of IKKε in activated T cells was examined. Upon PMA and ionomycin treatment, IKKε was gradually increased and reached ~3-fold of its basal level at 2-4 hours after stimulation (FIG. 8C). To monitor IKKε kinase activity, a Jurkat T cell line was established that stably expressed Flag-tagged IKKε. A kinase assay using precipitated IKKε showed that the kinase activity of IKKε was increased to ~8-fold at 4 hour after stimulation with PMA and ionomycin (FIG. 14*a*). The kinase activity of IKKε to phosphorylate serine residues within the N-terminus of IκBα in vitro also correlated with its own phosphorylation of Serine 172 ($S^{172}$), an indicator of IKKε activation (FIG. 14*a*). These results show that T cell activation up-regulates the kinase activity of IKKε.

To simultaneously probe NFAT phosphorylation of multiple sites by IKKε during T cell activation, NFAT2 was purified by affinity chromatography and its phosphorylation was analyzed with mass spectrometry. To do that, a Jurkat T cell line was established that stably expressed NFAT2 by lentivirus. In resting T cells, the phosphorylated $S^{161}$ can be detected at low level, whereas phosphorylation of the other three sites was below detection (FIG. 14*b*). Upon stimulation, the phosphorylation of $S^{117}$, $S^{151}$, $S^{161}$, and $S^{324}$ increased significantly (FIG. 14*b*), indicating that the phosphorylation of these four sites are coupled to T cell activation. A recent study has identified amlexanox, an agent clinically prescribed to treat aphthous ulcers, as a specific inhibitor of IKKε[39]. Amlexanox was employed to treat T cells and examine NFAT phosphorylation. When Jurkat T cells were stimulated with PMA and ionomycin while IKKε was inhibited with amlexanox, the phosphorylation of all four sites decreased to the level below detection by MS analysis (FIG. 14*b*). This result demonstrated the roles of IKKε in promoting the phosphorylation of all four sites within NFAT. Taken together, these results show that T cell activation up-regulates the kinase activity of IKKε to phosphorylate NFAT, providing a possible negative feedback mechanism to tailor T cell activation.

Example 6

Knockdown of IKKε Reduces NFAT Phosphorylation and Elevates T Cell Response

Figure 3:
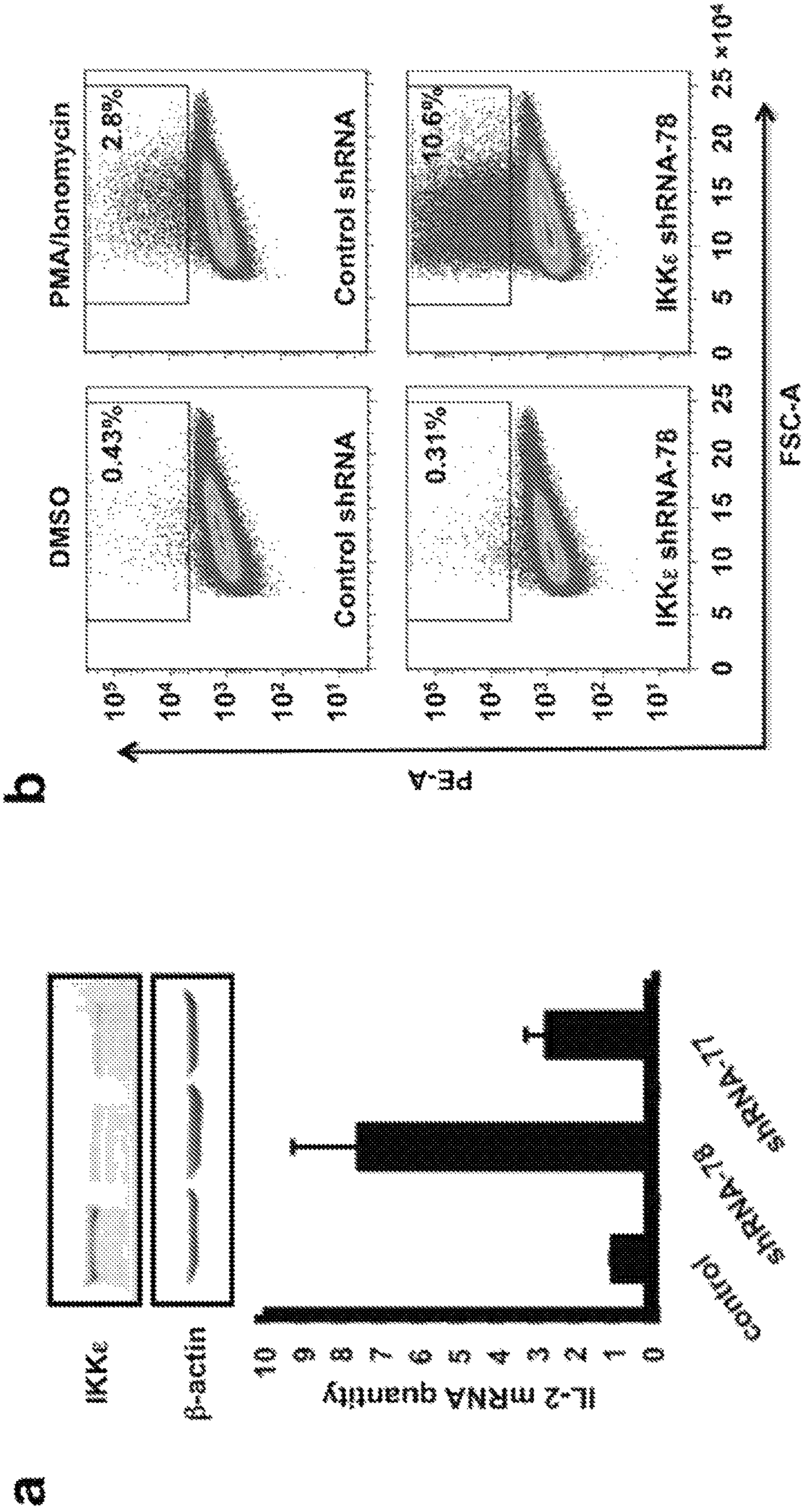
FIG. 3 shows that knockdown or pharmacological inhibition of IKKε promotes NFAT activation and T cell response. (A and B) Human Jurkat T cells were infected with control lentivirus (CTL) or lentivirus expressing shRNA specific for IKKε. Whole cell lysates were analyzed for IKKε expression by immunoblotting (top) and total RNA was analyzed by quantitative real-time PCR (qRT-PCR) with primers specific for IL-2 (bottom) (A). Jurkat T cells were stimulated with PMA and ionomycin for 5 h and examined by IL-2 intracellular staining (B). (C) CD3+ primary T cells were isolated from spleens of wild-type and Ikbke$^{-/-}$ mice, stimulated with PMA and ionomycin. Total RNA was extracted and analyzed by qRT-PCR for IL-2 expression. (D) Jurkat T cells stably expressing NFAT2 were activated with PMA plus ionomycin without (DMSO) or with amlexanox (50 μM). Precipitated NFAT2 was analyzed by two-dimensional gel electrophoresis and immunoblotting. (E) Jurkat T cells were stimulated with PMA and ionomycin, with increasing concentrations of an IKKε inhibitor (amlexanox), for 5 h and analyzed by IL-2 intracellular staining.
Figure 3:
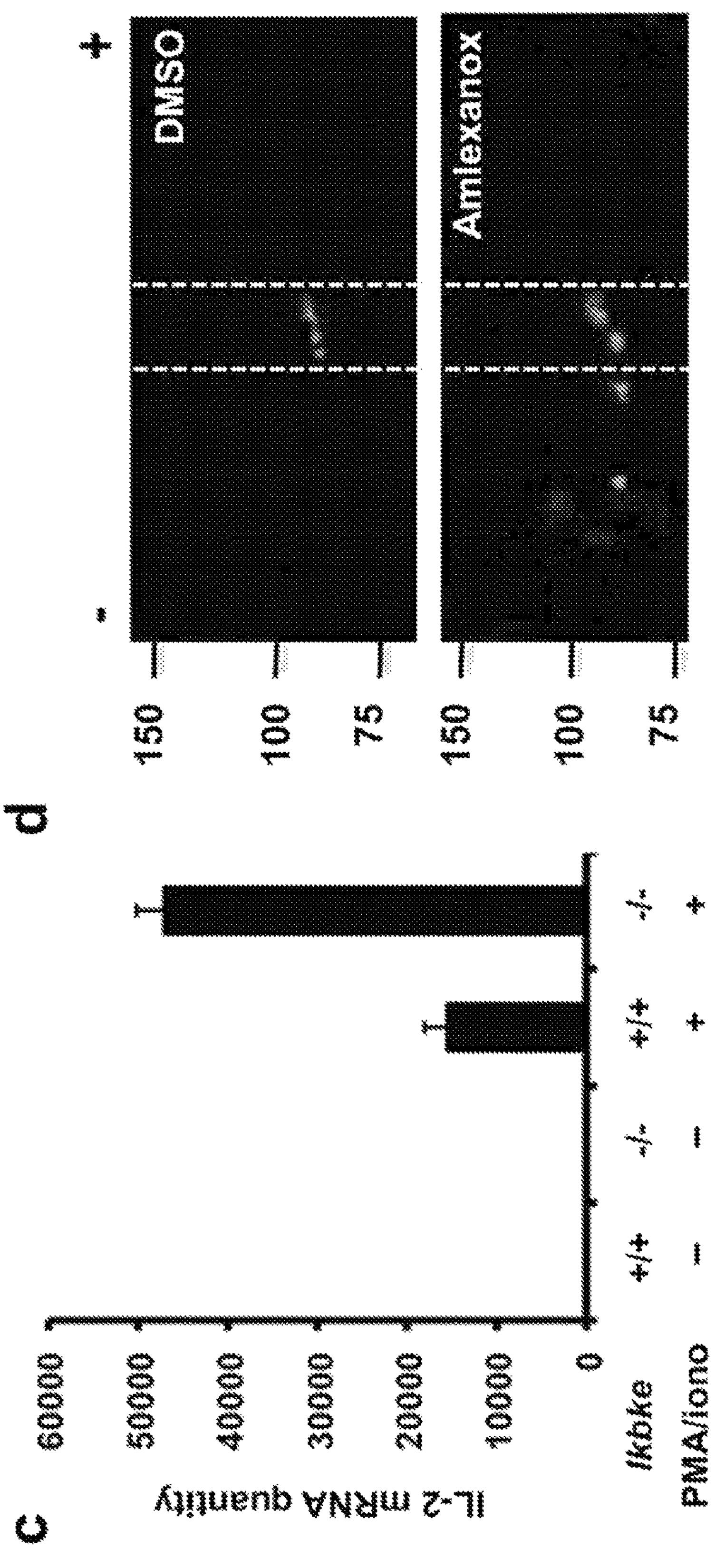
Figure 3:
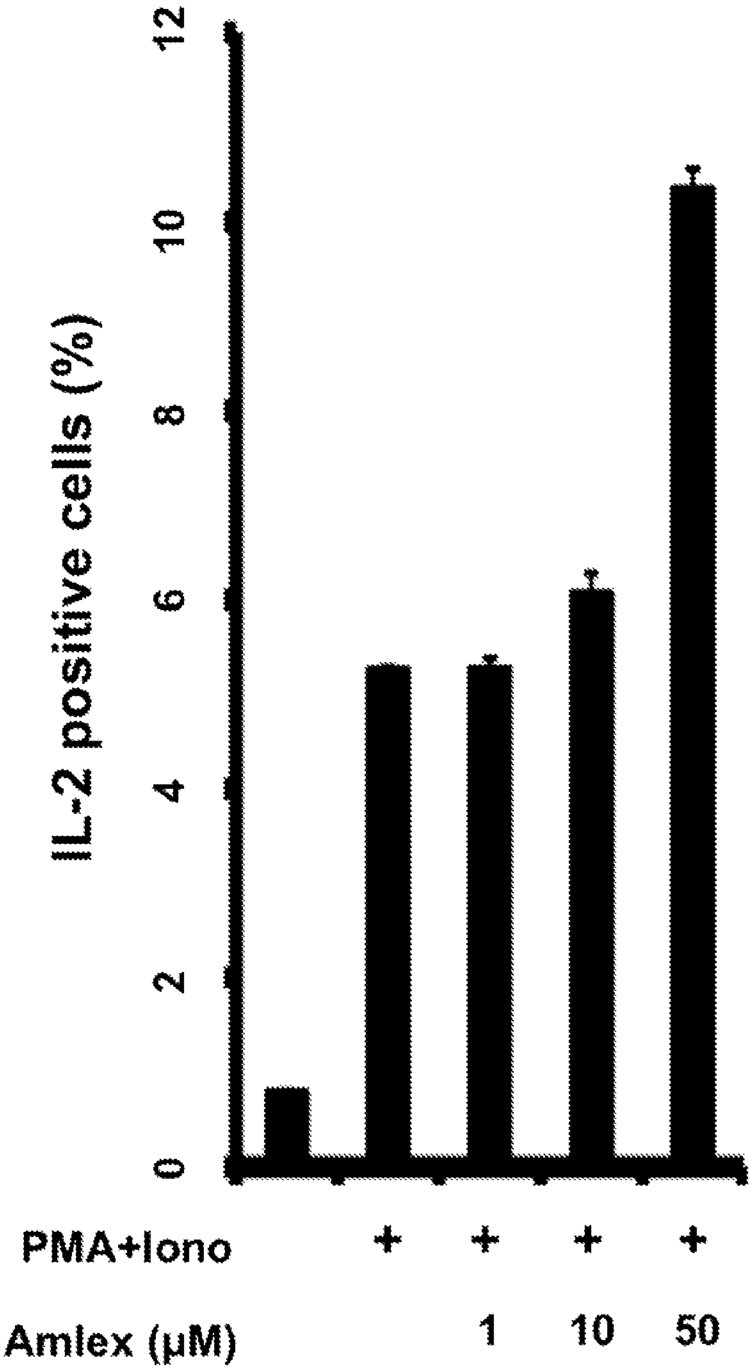
Figure 9:
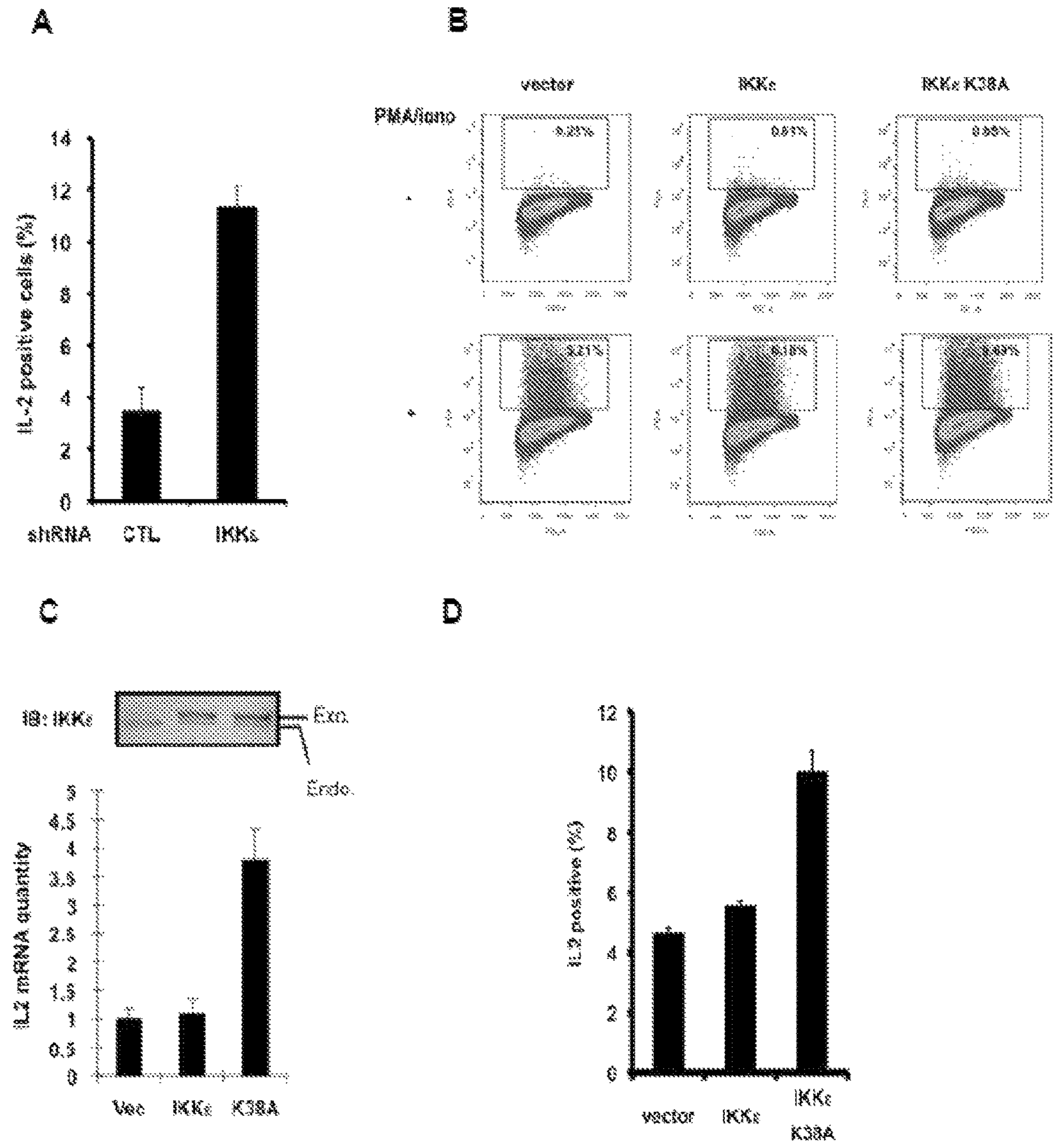
FIG. 9 shows that knockdown of IKKε or expression of its kinase-dead mutant promotes NFAT activation and T cell response. (A) Jurkat T cells were infected with control (CTL) lentivirus or lentivirus expressing IKKε shRNA 78 (SEQ ID NO:2). Cells were stimulated with PMA and ionomycin for 5 h and analyzed by IL-2 intracellular staining. Data represent the mean of three independent experiments and error bars denote standard deviation. (B) and (D) Jurkat T cells were infected with control lentivirus (Vector) or lentivirus containing IKKε or IKKεK38A. Cells were stimulated with PMA and ionomycin for 5 h and analyzed by IL-2 intracellular staining. Data represent the mean of three independent experiments and error bars denote standard deviation in (D). (C) Jurkat T cells were infected with control lentivirus or lentivirus containing wild-type IKKε or IKKεK38A. Whole cell lysates were analyzed by immunoblotting with anti-IKKε antibody (top) and total RNA was analyzed by qRT-PCR for IL-2 expression (bottom).
Figure 10:
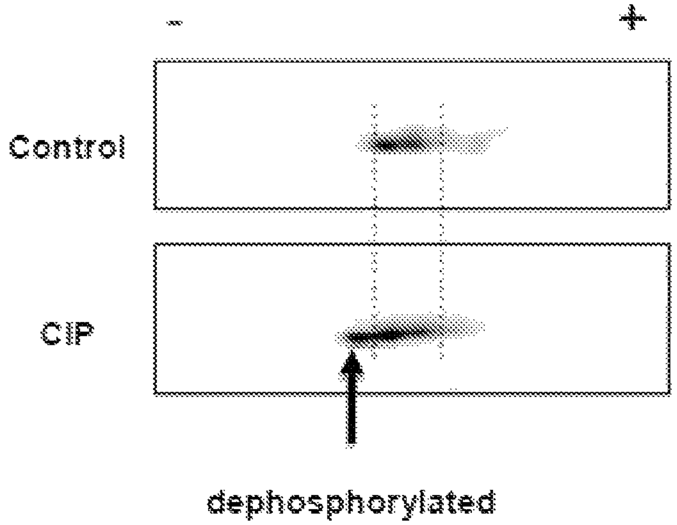
FIG. 10 shows that CIP treatment shifted NFAT2 in two-dimensional gel electrophoresis. NFAT2 was purified from Jurkat cells stably expressing NFAT2 stimulated with PMA plus ionomycin. Precipitated NFAT2 was treated with phosphatase (CIP) and analyzed by two-dimensional gel electrophoresis and immunoblotting.

To examine the roles of IKKε in T cell activation, IKKε expression in human Jurkat T cells was knocked down with short hairpin RNA (shRNA) (FIG. 3A). Two pairs of IKKε shRNA increased IL-2 mRNA by a factor of 7 and 3 (FIG. 3A), and IL-2 intracellular staining by ~2-4 fold (FIG. 3B and FIG. 9A), when induced with PMA and ionomycin. Exogenous IKKε and the kinase-dead IKKεK38A were also expressed by lentivirus infection in Jurkat cells. T cell activation was examined. While expression of wild-type IKKε had no detectable effect on IL-2 mRNA level, expression of IKKεK38A elevated IL-2 mRNA by a factor of 3.5 and the number of IL-2-positive cells by ~2-fold (FIGS. 9C and 9D). These results suggest that IKKεK38A has a dominant negative effect on endogenous IKKε in regulating NFAT activation. The lack of inhibition of IL-2 gene expression by exogenous IKKε suggests that endogenous IKKε in T cells was sufficient to suppress NFAT activation. Moreover, when treated with PMA and ionomycin, IL-2 mRNA of mouse primary $Ikbke^{-/-}$ T cells was ~3-fold of that of wild-type T cells (FIG. 3C), further demonstrating inhibition of NFAT activation by IKKε. Amlexanox, which is clinically prescribed to treat aphthous ulcers, may be a potent inhibitor of IKKε. It was tested whether this pharmacological agent can inhibit IKKε and NFAT phosphorylation, thereby boosting T cell activation. Treatment with amlexanox increased IL-2 intracellular staining in a dose-dependent manner (FIG. 3D). Furthermore, two-dimensional gel electrophoresis analysis demonstrated that NFAT2 was shifted toward the negatively charged side in the first dimension and migrated faster in the second dimension when IKKε was inhibited with amlexanox (FIG. 3E), indicating reduced phosphorylation that was recapitulated by treatment with alkaline phosphatase (FIG. 10). Thus, amlexanox treatment inhibits IKKε and reduces NFAT phosphorylation, thereby enhancing T cell activation. These results collectively indicate that inhibition of IKKε reduces NFAT2 phosphorylation and elevates NFAT activation.

Example 7

In Vivo Role of IKKε in Infection of a Model DNA Herpesvirus

Figure 4:
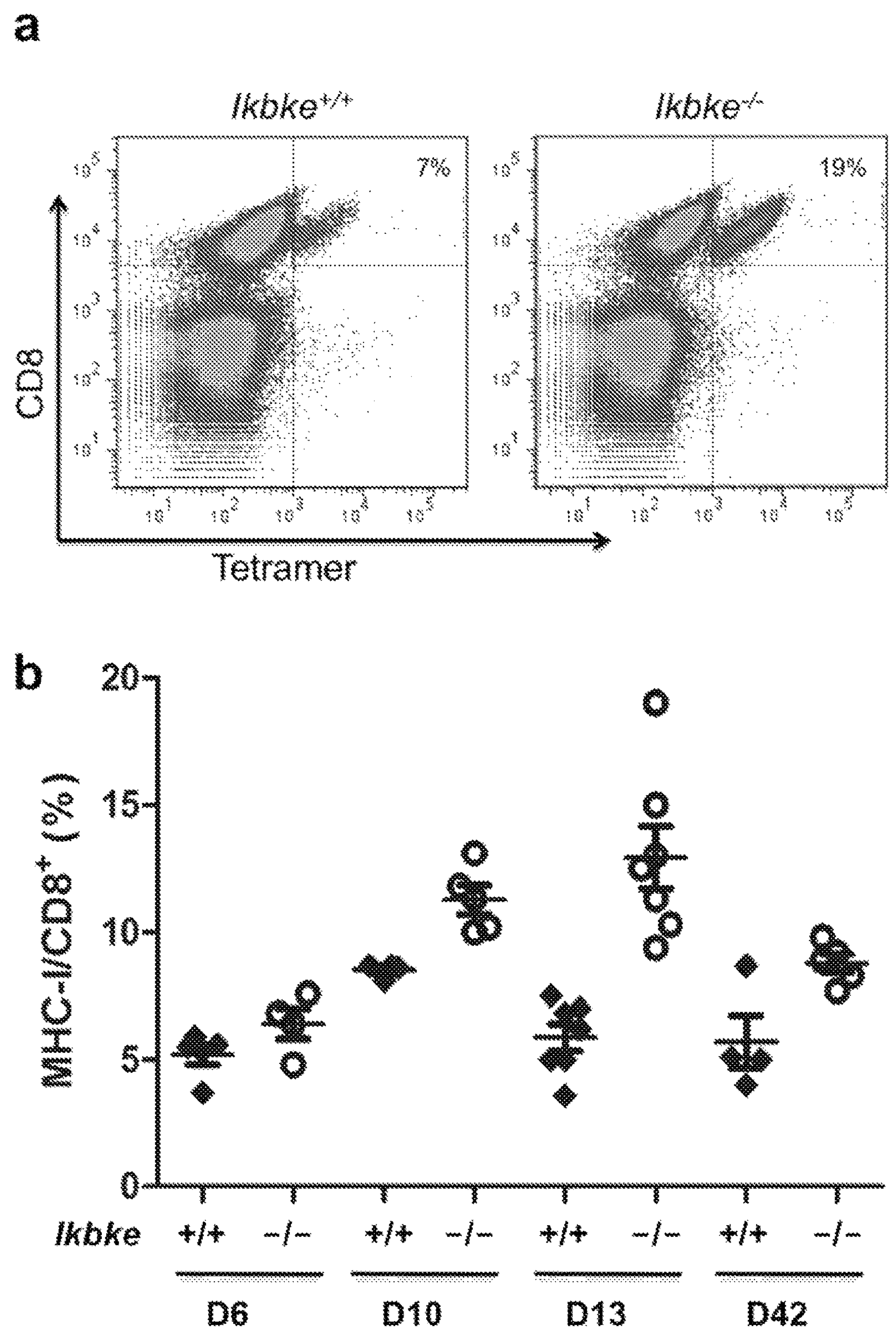
FIG. 4 shows that loss of IKKε results in more robust T cell response. (A-E) Gender- and age-matched Ikbke$^{+/+}$ and Ikbke$^{-/-}$ mice were intraperitoneally infected with $1\times10^6$ pfu of murine gamma herpesvirus 68 (γHV68). Splenocytes were harvested at 13 dpi, stained with anti-CD8 antibody and a tetramer containing viral antigenic peptide (of ORF61), and analyzed by flow cytometry. Representative data of individual or pooled mice were shown in (A) and (B), respectively. (C) CD3+ splenocytes were isolated from γHV68-infected wild-type and Ikbke$^{-/-}$ mice at 13 dpi and stimulated with viral antigenic peptide (ORF61). IFN-γ was determined by intracellular staining. *$p<0.05$. (D) Splenocytes labeled with CFSE were pulsed with or without viral peptide and transferred into γHV68 infected Ikbke$^{+/+}$ and Ikbke$^{-/-}$ mice. The specific killing was quantified by flow cytometry analysis. $p<0.01$. (E) γHV68 genome frequency in splenocytes was determined by limiting-dilution PCR (LD-PCR). (F) Gender- and age-matched wild-type and Ikbke$^{-/-}$ mice were intranasally infected with $1\times10^3$ pfu of PR8 influenza virus. CD8− and tetramer [containing a peptide of nucleoprotein (NP)]-staining were analyzed by flow cytometry. $p<0.01$. (G) Ikbke$^{-/-}$ mice were infected with $1\times10^3$ pfu of PR8 influenza virus and treated with cyclosporine A (CsA) every other day, and body weight was monitored at indicated days post-infection. (H) Lung of Ikbke$^{-/-}$ mice infected with PR8 was harvested at 8 dpi and analyzed by immunohistochemistry staining with anti-CD3 antibody. An enlarged image of low level of alveolitis/more T cell infiltrated region and that of a region of high level of alveolitis with less or no T cell infiltration were shown in top and bottom panels, respectively.
Figure 4:
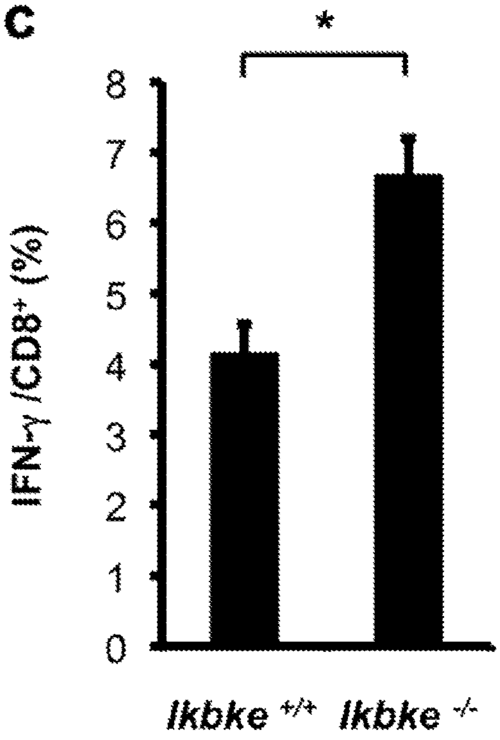
Figure 4:
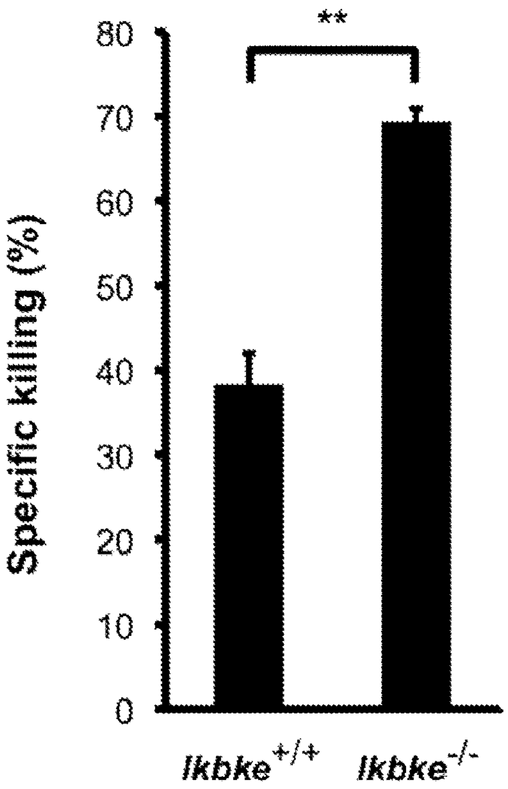
Figure 4:
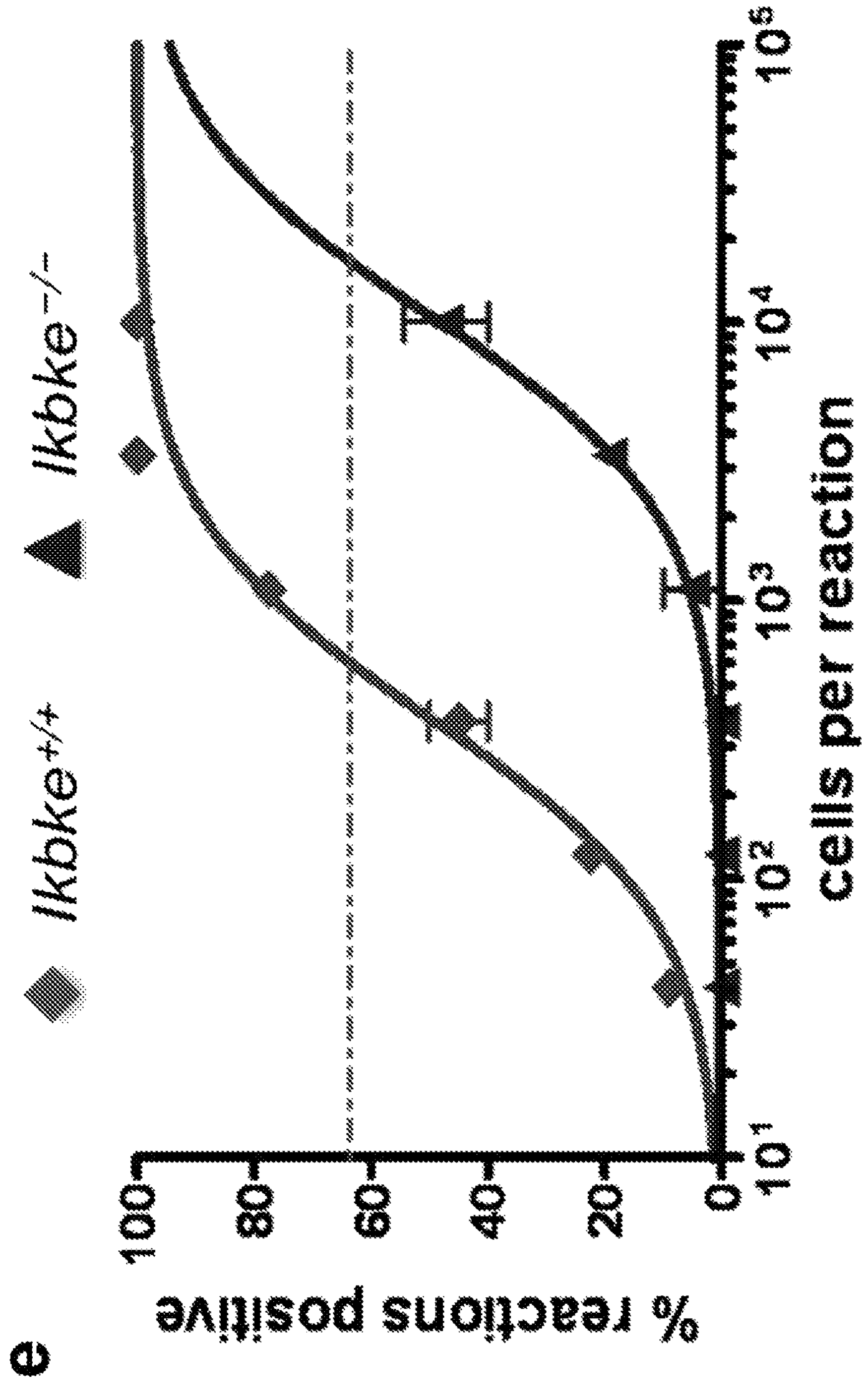
Figure 4:
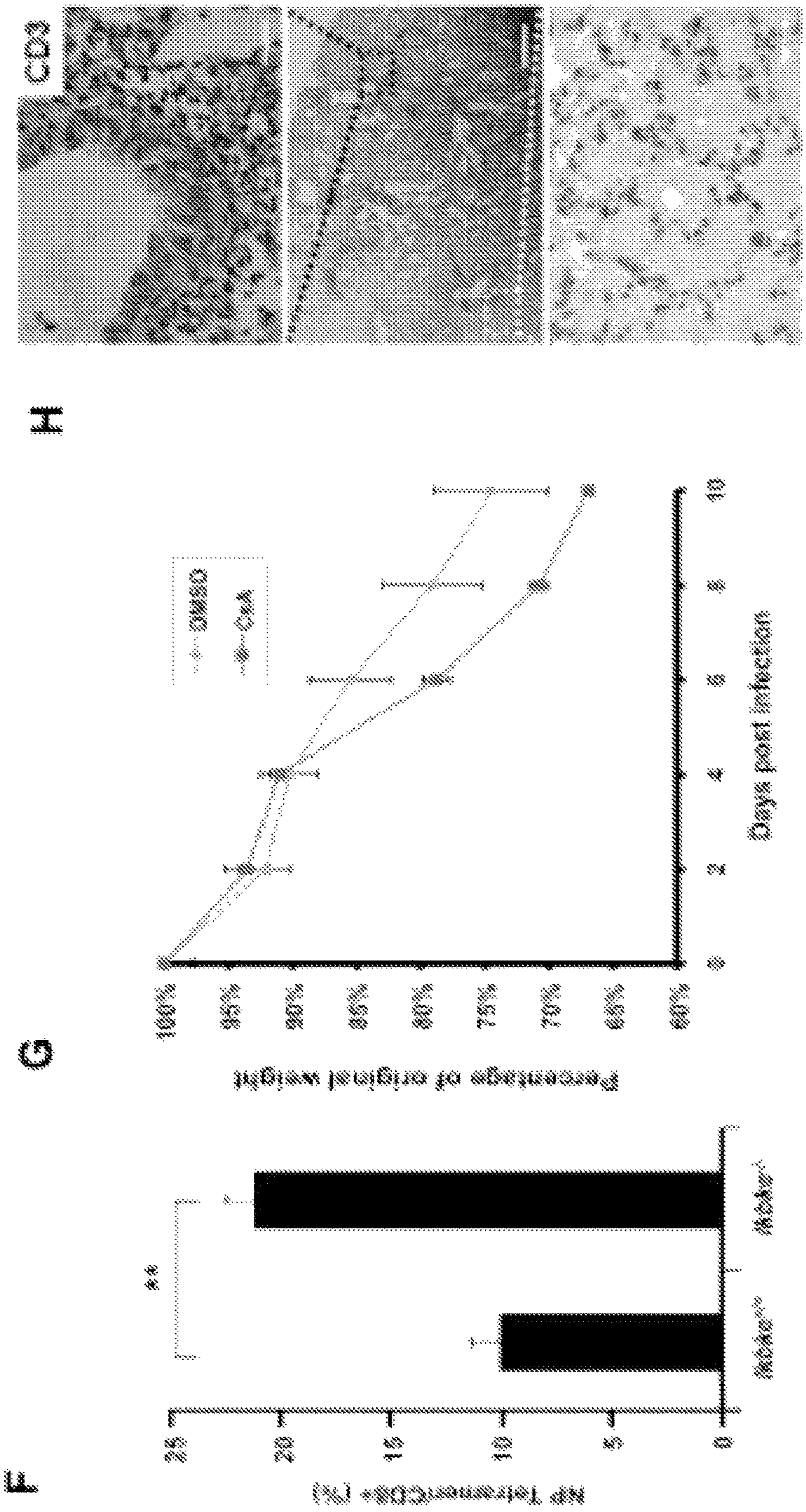
Figure 11:
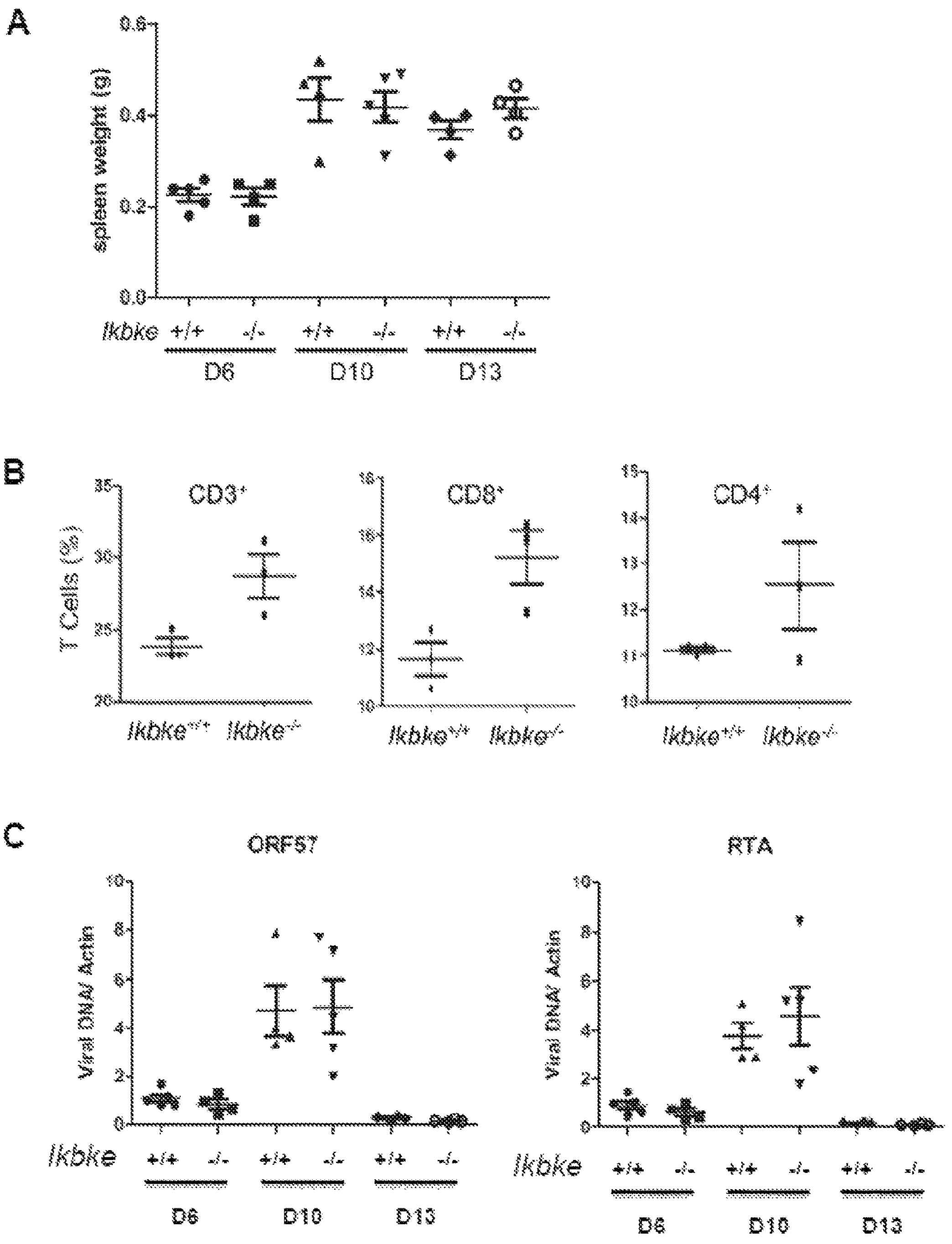
FIG. 11 shows the in vivo roles of IKKε in γHV68 infection. Gender- and age-matched wild-type and Ikbke$^{-/-}$ mice were intraperitoneally infected with $1\times10^6$ pfu of murine gamma herpesvirus 68 (γHV68). (A) Spleen weight was determined when mice were euthanized at indicated time points. (B) Splenocytes were isolated at 13 days post-infection and analyzed by flow cytometry with antibodies specific for CD3 (total T cells), CD4, and CD8 surface markers. (C) Total DNA was extracted from splenocytes and γHV68 genome copies were determined by quantitative real-time PCR.
Figure 12:
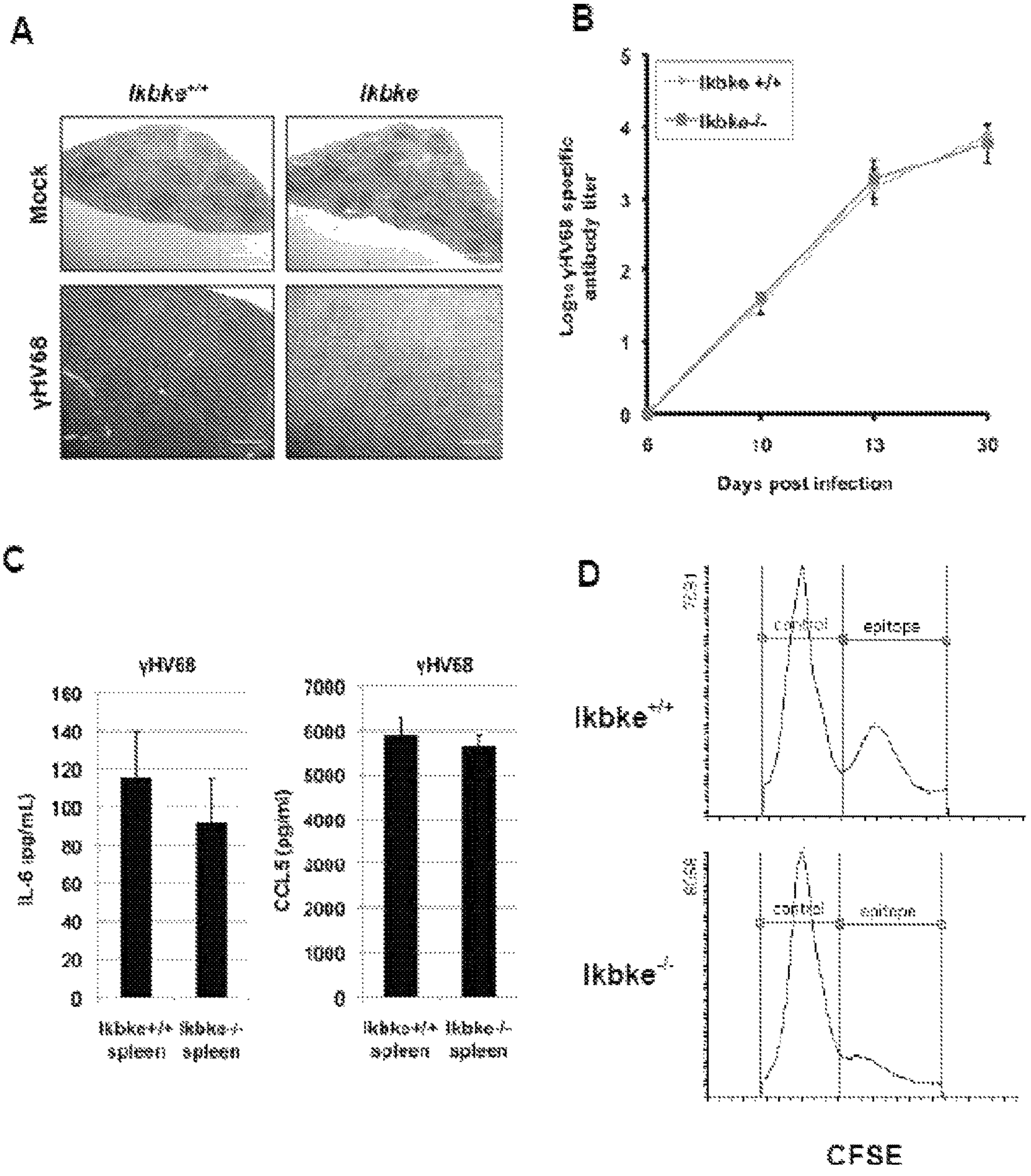
FIG. 12 shows the spleen histology, antibody production, cytokine secretion and in vivo killing in γHV68 infected wild-type and Ikbke$^{-/-}$ mice. (A) The spleen of wild-type and Ikbke$^{-/-}$ mice was collected at 13 dpi and analyzed by hematoxylin & eosin staining. Scale bars denote 100 μM (top two panels) and 25 μM (lower tow panels). (B) Sera were collected from wild-type and Ikbke$^{-/-}$ mice at indicated time and the relative virus-specific antibody was determined by ELISA using plate coated with purified virion. (C) The spleen was harvested at 13 dpi. IL-6 and CCL5 were determined by ELISA. (D) Representative data of in vivo killing assay.

NFAT activation is involved in T cell immunity and therefore host defense against viral infection. T cell response to infection by two distinct viruses, a persistence-prone DNA herpesvirus, murine gamma herpesvirus 68 (γHV68), and an acute RNA influenza virus, were examined. Murine γHV68 is a model virus for human oncogenic Kaposi's sarcoma-associated herpesvirus and Epstein-Barr virus. γHV68 infection in mice leads to a transient lytic replication phase lasting ~13 days, followed by the establishment of latent infection in lymphoid cells (e.g., B cells). Mice were infected with γHV68 via intraperitoneal injection, which permits lytic replication in the spleen and robust T cell responses. When infected with γHV68, wild-type and $Ikbke^{-/-}$ mice had similar level of splenomegaly (FIG. 11A). The total T cell count, including CD8 and CD4 T cells, in $Ikbke^{-/-}$ mice exceeded that in wild-type mice by ~25%, suggesting that T cell homeostasis is maintained in $Ikbke^{-/-}$ mice (FIG. 11B). By employing tetramer staining specific for a well-defined ORF61 epitope of γHV68, it was shown that loss of IKKε resulted in a ~2-3-fold increase in CD8 T cells at 13 days post-infection (dpi) (FIG. 4A). When CD8 T cell response was examined over time by tetramer staining, it was found that loss of IKKε resulted in a more rapid increase in virus-specific CD8 T cells from 6 to 10 dpi (FIG. 4B). The difference between CD8 T cells in wild-type mice and those of $Ikbke^{-/-}$ mice peaked at 13 dpi. Upon viral antigenic peptide stimulation, ~7.5% of CD3-enriched $Ikbke^{-/-}$ splenocytes were IFN-γ-positive, while ~4% of wild-type splenocytes were positive for IFN-γ (FIG. 4C). Quantitative real-time PCR (qRT-PCR) revealed that spleen viral loads (genome copy number) were similar in wild-type and Ikbke$^{-/-}$ mice at 6 and 10 dpi, but at 13 dpi was reduced by 50% in Ikbke$^{-/-}$ as compared to wild-type mice (FIG. 11C). Although the overall spleen architecture was similar in mock-infected mice, germinal centers were expanded in virus-infected spleens of wild-type and Ikbke$^{-/-}$ mice (FIG. 12A). γHV68 infection in wild-type and Ikbke$^{-/-}$ mice induced equivalent virus-specific antibodies in sera (FIG. 12B) and comparable levels of IL-6 and CCL5 in the spleen (FIG. 12C). These results agree with previous reports that IKKε is dispensable for cytokine production in response to viral infection.

Next, an in vivo killing assay was performed to assess the functionality of CD8 T cells in γHV68-infected mice. Splenocytes were loaded with the ORF61 antigenic peptide and injected into wild-type or Ikbke$^{-/-}$ mice that were infected with γHV68 for 13 days. At 8 hours post-injection, a ~40% reduction of antigen-loaded target cells in wild-type mice was observed. Remarkably, antigen-bearing splenocytes decreased by >70% in γHV68-infected Ikbke$^{-/-}$ mice (FIG. 4D and FIG. 12D), indicative of an increased CD8 T cell response. To determine the consequence of increased T cell response, γHV68 latent infection in splenocytes at 42 dpi was examined by limiting-dilution PCR (LD-PCR) to assess viral genome frequency. This result showed that loss of IKKε reduced the frequency of cells containing γHV68 to ~1 in 10,000 cells, compared to ~1 in 200 in wild-type cells (FIG. 4E). Thus, elevated CD8 T cell response correlates with reduced persistent herpes virus infection.

Example 8

Role of CD8 T Cells to Reduced Latent Infection of γHV68

Figure 13:
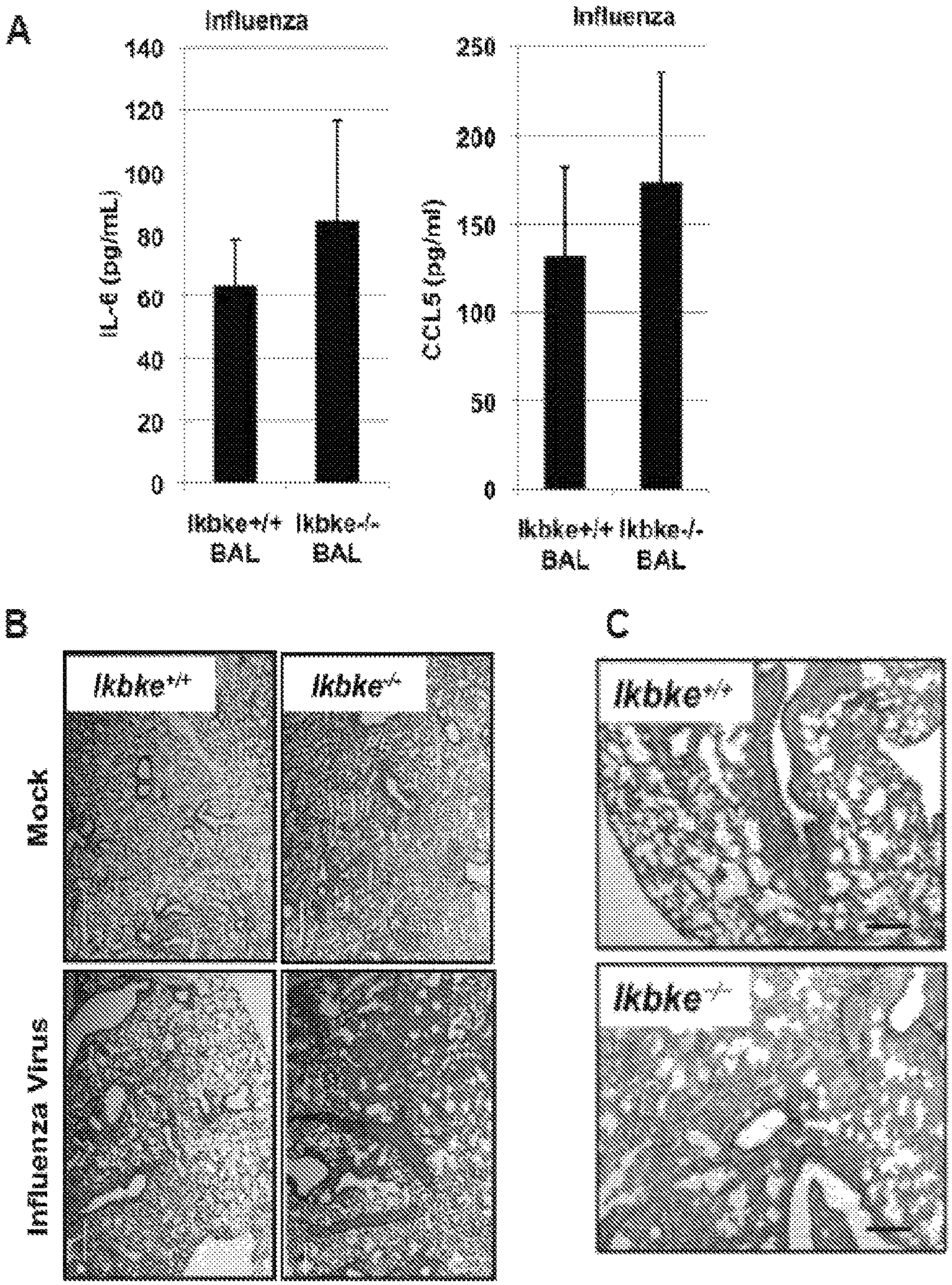
FIG. 13 shows the in vivo roles of IKKε in infection of the RNA influenza virus. (A) Gender- and age-matched wild-type and Ikbke$^{-/-}$ mice were infected with 1000 pfu of (mouse-adapted PR8) influenza virus. Lungs were harvested at 8 dpi. IL-6 and CCL5 in the lung were determined by ELISA. (B) Lungs were also analyzed by hematoxylin & eosin staining. Scale bars denote 100 μM. Enlarged representative areas of lungs of wild-type and Ikbke$^{-/-}$ mice were shown in (C). Scale bars denote 25 μM.
Figure 15:
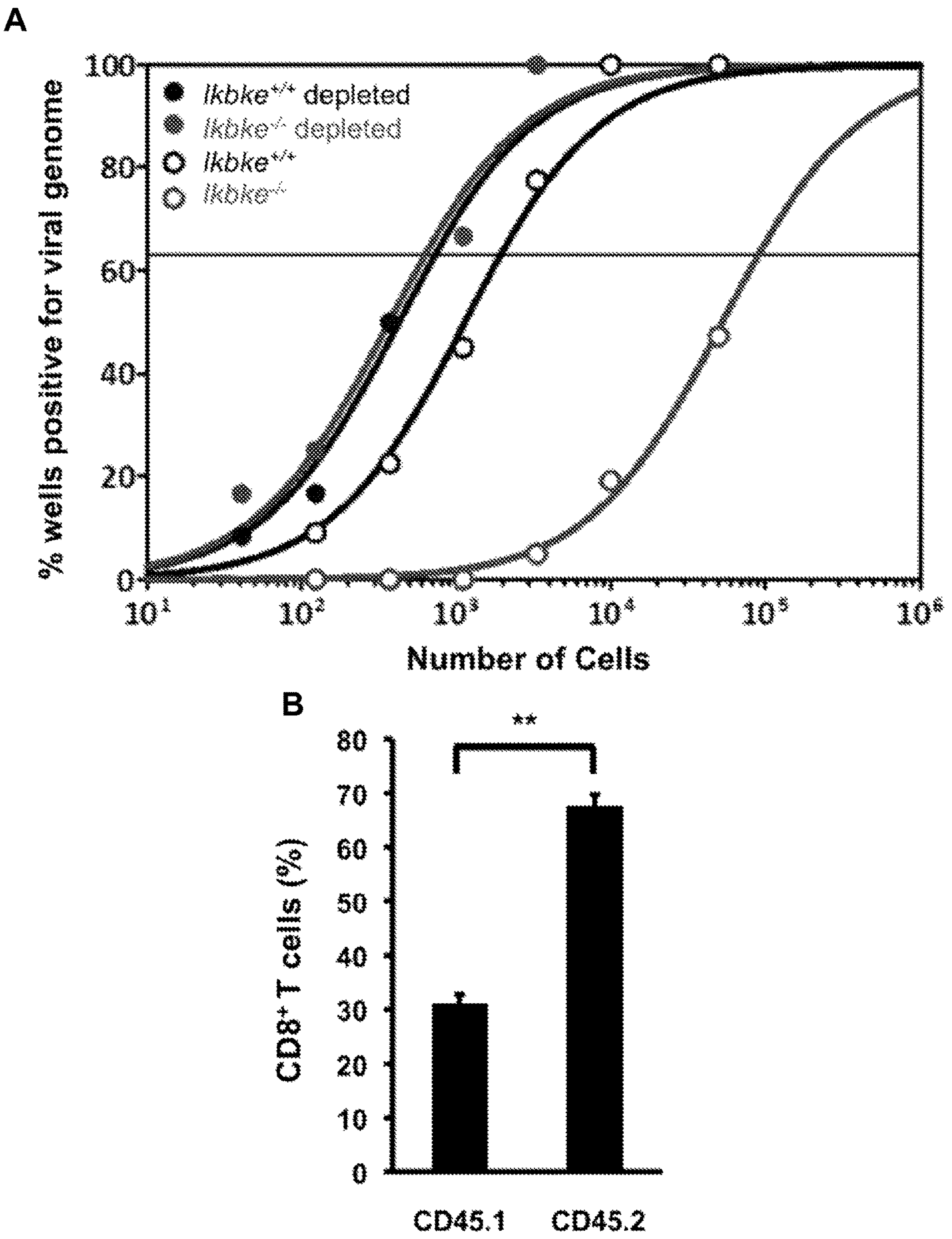
FIG. 15 shows that loss of IKKε results in more robust T cell response. (A) Gender- and age-matched wild-type and Ikbke−/− mice were intraperitoneally infected with $1\times10^6$ pfu of γHV68. Mice were Mock treated or depleted with anti-CD8 antibody at 16 dpi. Splenocytes were harvested at 42 dpi and viral genome frequency was determined as in FIG. 4A. (B) Two million of CD3+ splenocytes of wild-type and Ikbke−/− mice were mixed and transferred into Rag-2−/− mice then the mice were infected with γHV68. At 13 dpi, splenocytes were harvested and analyzed for CD45.1 (wild-type) and CD45.2 (Ikbke−/−) within the CD8 T cell subset. **p<0.01.

To determine the contribution of CD8 T cells to the reduced latent infection of γHV68, CD8 T cells were depleted with an anti-CD8 antibody from 16 dpi when latent infection was successfully established. FACS analysis indicated that, at 42 dpi, less than 1% of CD8 T cells remained after depletion, while CD4+ cells were unchanged (FIG. 13A). When genome frequency of γHV68 was determined, depletion of CD8+ T cells slightly increased viral genome frequency in wild-type splenocytes, consistent with the reported role of CD8+ T cells in controlling viral latent infection. Remarkably, depletion of CD8+ T cells completely restored viral latent infection to that of wild-type mice treated with anti-CD8 antibody (FIG. 15A). The curves of γHV68 latent infection were identical in wild-type and IKKε-deficient mice that were depleted of CD8 T cells, indicating that the increased CD8 T cell response in IKKε-deficient mice primarily restricts viral latent infection. These results collectively support the conclusion that loss of IKKε increases CD8 T cell response that, in turn, diminishes γHV68 latent infection.

To test whether IKKε has an intrinsic activity in CD8 T cells, an equal number of wild-type (CD45.1) or IKKε-deficient (CD45.2) CD3+ T cells were transferred into Rag2$^{-/-}$ mice. These mice were then infected with γHV68, and CD8 T cells were quantified at 13 dpi. The CD8+ T cell population of Ikbke−/− mice was observed to be more than two-fold of that of Ikbke$^{+/+}$ mice (FIG. 15B and FIG. 13B). This result demonstrates an intrinsic role of IKKε in T cell activation and maintenance, indicating that IKKε deficiency is beneficial to CD8 T cell maintenance.

Example 9

Role of IKKε in Infection of RNA Influenza Virus

IKKε may have a role in relaying type I IFN signaling. Loss of IKKε impairs host innate immune defense in response to influenza virus infection. To determine the role of IKKε in regulating NFAT activation during acute viral infection, T cell responses to influenza virus infection was examined. Tetramer staining specific for a dominant nucleoprotein (NP) epitope of influenza virus indicated that CD8 T cell activation was increased from ~10% in wild-type mice to ~20% in Ikbke$^{-/-}$ mice at 8 dpi (FIG. 4F). The total T cell counts in bronchoalveolar lavage (BAL) were similar in wild-type and Ikbke$^{-/-}$ mice (data not shown). Furthermore, comparable levels of IL-6 and CCL5 were detected in BALs of PR8-infected wild-type and Ikbke$^{-/-}$ mice (FIG. 13A). Due to the role of IKKε in innate immune defense against influenza virus infection, lungs of Ikbke$^{-/-}$ mice were severely damaged, demonstrating extensive alveolitis and peribronchiolitis that were associated with hemorrhage and edema (FIGS. 13B and 13C). By contrast, the structure of lungs of wild-type mice was overall intact with localized mild bronchiolitis. A close inspection of the area of high cellularity in Ikbke$^{-/-}$ lungs revealed that lung alveoli were filled with fluid, likely compromising the normal gas exchange in alveolar compartment. To query the roles of augmented T cell activation in influenza infection, virus-infected mice were treated with cyclosporin A, a specific inhibitor of the calcineurin-mediated NFAT activation, and examined mouse weight loss and lung injury. It was found that cyclosporin A treatment, after PR8 infection, resulted in an additional ~10% weight loss of Ikbke$^{-/-}$ mice (FIG. 4G), suggesting that the increased T cell response, resulting from IKKε deficiency, protects mice from more severe body weight loss. In support of this, the weight loss occurred at 6 dpi, which coincides with T cell responses. Moreover, CD3 immunohistochemistry staining indicated that T cells were high in regions with intact alveolar structure and scarce in those with alveolitis, demonstrating an inverse correlation between T cell infiltration and the severity of lung injury (FIG. 4H). These results collectively support the conclusion that an elevated CD8 T cell response, resulting from loss of IKKε, protects hosts from viral infection and pathogenesis.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

SEQUENCES
IKKε shRNA 77
SEQ ID NO: 1
CCGGCTGGACGATGATGAGAAGTTTCTCGAGAAACTTCTCATCATCGTCCAGTTTTT

IKKε shRNA 78
SEQ ID NO: 2
CCGGAGAAGTTCGTCTCGGTCTATGCTCGAGCATAGACCGAGACGAACTTCTTTTTG q-PCR primer for Mouse β-Actin
SEQ ID NO: 3
TCTACGAGGGCTATGCTCTCC q-PCR primer for Mouse β-Actin
SEQ ID NO: 4
TCTTTGATGTCACGCACGATTTC q-PCR primer for Mouse IL-2
SEQ ID NO: 5
CCTGAGCAGGATGGAGAATTACA q-PCR primer for Mouse IL-2
SEQ ID NO: 6
TCCAGAACATGCCGCAGAG q-PCR primer for Human β-Actin
SEQ ID NO: 7
GCACAGAGCCTCGCCTT q-PCR primer for Human β-Actin
SEQ ID NO: 8
GTTGTCGACGACGAGCG q-PCR primer for Human IL-2
SEQ ID NO: 9
AACTCACCAGGATGCTCACATTTA q-PCR primer for Human IL-2
SEQ ID NO: 10
TCCCTGGGTCTTAAGTGAAAGTTT q-PCR primer for ORF57
SEQ ID NO: 11
CCGACTACACGCAACACAAC q-PCR primer for ORF57
SEQ ID NO: 12
AAATAACCTGGGTGCTGTCAC q-PCR primer for RTA
SEQ ID NO: 13
TTTATCAGCACGCCATCAAC q-PCR primer for RTA
SEQ ID NO: 14
TGCGGAACAGGTGTGATTATC q-PCR primer for β-Actin
SEQ ID NO: 15
CAGGCATTGTGATGGACTCC q-PCR primer for β-Actin
SEQ ID NO: 16
CAAGAAGGAAGGCTGGAAAAG Major histocompatibility complex (MHC)/peptide tetramers for γHV68 ORF61 524-531/Kb
SEQ ID NO: 17
TSINFVKI Major histocompatibility complex (MHC)/peptide tetramers for influenza virus NP 366-374/Db
SEQ ID NO: 18
ASNENMETM NFAT conserved serine-rich motif, polypeptide
SEQ ID NO: 19
SVTDDSWLG NFAT epitope
SEQ ID NO: 20

-continued

SPRIEIT

IKKε, *Homo sapiens,* isoform 1 (CCDS30996.1), amino acid (716 AA)
SEQ ID NO: 21

MQSTANYLWHTDDLLGQGATASVYKARNKKSGELVAVKVFNTTSYLRPREVQVREFEVLRKLNHQNIVKL

FAVEETGGSRQKVLVMEYCSSGSLLSVLESPENAFGLPEDEFLVVLRCVVAGMNHLRENGIVHRDIKPGN

IMRLVGEEGQSIYKLTDFGAARELDDDEKFVSVYGTEEYLHPDMYERAVLRKPQQKAFGVTVDLWSIGVT

LYHAATGSLPFIPFGGPRRNKEIMYPITTEKPAGAIAGAQPPENGPLEWSYTLPITCQLSLGLQSQLVPI

LANILEVEQAKCWGFDQFFAETSDILQRVVVHVFSLSQAVLHHIYIHAHNTIAIFQEAVHKQTSVAPPHQ

EYLFEGHLCVLEPSVSAQHIAHTTASSPLTLFSTAIPKGLAFRDPALDVPKFVPKVDLQADYNTAKGVLG

AGYQALRLARALLDGQELMFRGLNWVMEVLQATCRRTLEVARTSLLYLSSSLGTERFSSVAGTPEIQELK

AAAELPSRLRTLAEVLSRCSQNITETQESLSSLNRELVKSRDQVHEDRSIQQIQCCLDKMNFIYKQFKKS

RMRPGLGYNEEQIHKLDKVNFSHLAKRLLQVFQEECVQKYQASLVTHGKRMRVVHETRNHLRLVGCSVAA

CNTEAQGVQESLSKLLEELSHQLLQDRAKGAQASPPPIAPYPSPTRKDLLLHMQELCEGMKLLASDLLDN

NRIIERLNRVPAPPDV

IKKε, *Homo sapiens,* isoform 1 (CCDS30996.1), nucleotide (2151 nt)
SEQ ID NO: 22

ATGCAGAGCACAGCCAATTACCTGTGGCACACAGATGACCTGCTGGGGCAGGGGGCCACTGCCAGTGTGT

ACAAGGCCCGCAACAAGAAATCCGGAGAGCTGGTTGCTGTGAAGGTCTTCAACACTACCAGCTACCTGCG

GCCCCGCGAGGTGCAGGTGAGGGAGTTTGAGGTCCTGCGGAAGCTGAACCACCAGAACATTGTCAAGCTC

TTTGCGGTGGAGGAGACGGGCGGAAGCCGGCAGAAGGTACTGGTGATGGAGTACTGCTCCAGTGGGAGCC

TGCTGAGTGTGCTGGAGAGCCCTGAGAATGCCTTTGGGCTGCCTGAGGATGAGTTCCTGGTGGTGCTGCG

CTGTGTGGTGGCCGGCATGAACCACCTGCGGGAGAACGGCATTGTGCATCGCGACATCAAGCCGGGGAAC

ATCATGCGCCTCGTAGGGGAGGAGGGGCAGAGCATCTACAAGCTGACAGACTTCGGCGCTGCCCGGGAGC

TGGATGATGATGAGAAGTTCGTCTCGGTCTATGGGACTGAGGAGTACCTGCATCCCGACATGTATGAGCG

GGCGGTGCTTCGAAAGCCCCAGCAAAAAGCGTTCGGGGTGACTGTGGATCTCTGGAGCATTGGAGTGACC

TTGTACCATGCAGCCACTGGCAGCCTGCCCTTCATCCCCTTTGGTGGGCCACGGCGGAACAAGGAGATCA

TGTACCGGATCACCACGGAGAAGCCGGCTGGGGCCATTGCAGGTGCCCAGAGGCGGGAGAACGGGCCCCT

GGAGTGGAGCTACACCCTCCCCATCACCTGCCAGCTGTCACTGGGGCTGCAGAGCCAGCTGGTGCCCATC

CTGGCCAACATCCTGGAGGTGGAGCAGGCCAAGTGCTGGGGCTTCGACCAGTTCTTTGCGGAGACCAGTG

ACATCCTGCAGCGAGTTGTCGTCCATGTCTTCTCCCTGTCCCAGGCAGTCCTGCACCACATCTATATCCA

TGCCCACAACACGATAGCCATTTTCCAGGAGGCCGTGCACAAGCAGACCAGTGTGGCCCCCCGACACCAG

GAGTACCTCTTTGAGGGTCACCTCTGTGTCCTCGAGCCCAGCGTCTCAGCACAGCACATCGCCCACACGA

CGGCAAGCAGCCCCCTGACCCTCTTCAGCACAGCCATCCCTAAGGGGCTGGCCTTCAGGGACCCTGCTCT

GGACGTCCCCAAGTTCGTCCCCAAAGTGGACCTGCAGGCGGATTACAACACTGCCAAGGGCGTGTTGGGC

GCCGGCTACCAGGCCCTGCGGCTGGCACGGGCCCTGCTGGATGGGCAGGAGCTAATGTTTCGGGGGCTGC

ACTGGGTCATGGAGGTGCTCCAGGCCACATGCAGACGGACTCTGGAAGTGGCAAGGACATCCCTCCTCTA

CCTCAGCAGCAGCCTGGGAACTGAGAGGTTCAGCAGCGTGGCTGGAACGCCTGAGATCCAGGAACTGAAG

GCGGCTGCAGAACTGAGGTCCAGGCTGCGGACTCTAGCGGAGGTCCTCTCCAGATGCTCCCAAAATATCA

CGGAGACCCAGGAGAGCCTGAGCAGCCTGAACCGGGAGCTGGTGAAGAGCCGGGATCAGGTACATGAGGA

CAGAAGCATCCAGCAGATTCAGTGCTGTTTGGACAAGATGAACTTCATCTACAAACAGTTCAAGAAGTCT

AGGATGAGGCCAGGGCTTGGCTACAACGAGGAGCAGATTCACAAGCTGGATAAGGTGAATTTCAGTCATT

TAGCCAAAAGACTCCTGCAGGTGTTCCAGGAGGAGTGCGTGCAGAAGTATCAAGCGTCCTTAGTCACACA

CGGCAAGAGGATGAGGGTGGTGCACGAGACCAGGAACCACCTGCGCCTGGTTGGCTGTTCTGTGGCTGCC

-continued

TGTAACACAGAAGCCCAGGGGGTCCAGGAGAGTCTCAGCAAGCTCCTGGAAGAGCTATCTCACCAGCTCC

TTCAGGACCGAGCAAAGGGGGCTCAGGCCTCGCCGCCTCCCATAGCTCCTTACCCCAGCCCTACACGAAA

GGACCTGCTTCTCCACATGCAAGAGCTCTGCGAGGGGATGAAGCTGCTGGCATCTGACCTCCTGGACAAC

AACCGCATCATCGAACGGCTAAATAGAGTCCCAGCACCTCCTGATGTCTGA

IKKε, *Homo sapiens,* isoform 2 (CCDS73019.1), amino acid (657 AA)
SEQ ID NO: 23

MQSTANYLWHTDDLLGQGATASVYKARNKKSGELVAVKVFNTTSYLRPREVQVPEFEVLRKLNHQNIVKL

FAVEETGGSRQKVLVMEYCSSGSLLSVLESPENAFGLPEDEFLVVLRCVVAGMNHLRENGIVHPDIKPGN

IMPLVGEEGQSIYKLTDFGAAPRLDDDEKFVSVYGTRRYLHPDMYERAVLRKPQQKAFGVTVDLWSIGVT

LYHAATGSLPFIPFGGPRRNKEIMYPITTEKPAGAIAGAQPPENGPLERSYTLPITCQLSLGLQSQLVPI

LANILEVEQAKCWGFDQFFAETSDILQRVVVHVFSLSQAVLHHIYIHAHNTIAIFQEAVHKQTSVAPPHQ

EYLFEGHLCVLEPSVSAQHIAHTTASSPLTLFSTAIPKGLAFPDPALDVPKFVPKVDLQADYNTAKGVLG

AGYQALRLARALLDGQELMPPGLHWVMEVLQATCRRTLEVARTSLLYLSSSLGTERFSSVAGTPEIQELK

AAAELPSPLRTLAEVLSRCSQNITETQESLSSLNRELVKSRDQVHEDRSIQQIQCCLDKMNFIYKQFKKS

PMRPGLGYNEEQIHKLDKVNFSHLAKRLLQVFQEECVQKYQASLVTHGKPMRVVHETRNHLRLVGCSVAA

CNTEAQGVQESLSKNARALPGDEAAGI

IKKε, *Homo sapiens,* isoform 2 (CCDS73019.1), nucleotide (1974 nt)
SEQ ID NO: 24

ATGCAGAGCACAGCCAATTACCTGTGGCACACAGATGACCTGCTGGGGCAGGGGGCCACTGCCAGTGTGT

ACAAGGCCCGCAACAAGAAATCCGGAGAGCTGGTTGCTGTGAAGGTCTTCAACACTACCAGCTACCTGCG

GCCCCGCGAGGTGCAGGTGAGGGAGTTTGAGGTCCTGCGGAAGCTGAACCACCAGAACATTGTCAAGCTC

TTTGCGGTGGAGGAGACGGGCGGAAGCCGGCAGAAGGTACTGGTGATGGAGTACTGCTCCAGTGGGAGCC

TGCTGAGTGTGCTGGAGAGCCCTGAGAATGCCTTTGGGCTGCCTGAGGATGAGTTCCTGGTGGTGCTGCG

CTGTGTGGTGGCCGGCATGAACCACCTGCGGGAGAACGGCATTGTGCATCGCGACATCAAGCCGGGGAAC

ATCATGCGCCTCGTAGGGGAGGAGGGGCAGAGCATCTACAAGCTGACAGACTTCGGCGCTGCCCGGGAGC

TGGATGATGATGAGAAGTTCGTCTCGGTCTATGGGACTGAGGAGTACCTGCATCCCGACATGTATGAGCG

GGCGGTGCTTCGAAAGCCCCAGCAAAAAGCGTTCGGGGTGACTGTGGATCTCTGGAGCATTGGAGTGACC

TTGTACCATGCAGCCACTGGCAGCCTGCCCTTCATCCCCTTTGGTGGGCCACGGCGGAACAAGGAGATCA

TGTACCGGATCACCACGGAGAAGCCGGCTGGGGCCATTGCAGGTGCCCAGAGGCGGGAGAACGGGCCCCT

GGAGTGGAGCTACACCCTCCCCATCACCTGCCAGCTGTCACTGGGGCTGCAGAGCCAGCTGGTGCCCATC

CTGGCCAACATCCTGGAGGTGGAGCAGGCCAAGTGCTGGGGCTTCGACCAGTTCTTTGCGGAGACCAGTG

ACATCCTGCAGCGAGTTGTCGTCCATGTCTTCTCCCTGTCCCAGGCAGTCCTGCACCACATCTATATCCA

TGCCCACAACACGATAGCCATTTTCCAGGAGGCCGTGCACAAGCAGACCAGTGTGGCCCCCCGACACCAG

GAGTACCTCTTTGAGGGTCACCTCTGTGTCCTCGAGCCCAGCGTCTCAGCACAGCACATCGCCCACACGA

CGGCAAGCAGCCCCCTGACCCTCTTCAGCACAGCCATCCCTAAGGGGCTGGCCTTCAGGGACCCTGCTCT

GGACGTCCCCAAGTTCGTCCCCAAAGTGGACCTGCAGGCGGATTACAACACTGCCAAGGGCGTGTTGGGC

GCCGGCTACCAGGCCCTGCGGCTGGCACGGGCCCTGCTGGATGGGCAGGAGCTAATGTTTCGGGGGCTGC

ACTGGGTCATGGAGGTGCTCCAGGCCACATGCAGACGGACTCTGGAAGTGGCAAGGACATCCCTCCTCTA

CCTCAGCAGCAGCCTGGGAACTGAGAGGTTCAGCAGCGTGGCTGGAACGCCTGAGATCCAGGAACTGAAG

GCGGCTGCAGAACTGAGGTCCAGGCTGCGGACTCTAGCGGAGGTCCTCTCCAGATGCTCCCAAAATATCA

CGGAGACCCAGGAGAGCCTGAGCAGCCTGAACCGGGAGCTGGTGAAGAGCCGGGATCAGGTACATGAGGA

CAGAAGCATCCAGCAGATTCAGTGCTGTTTGGACAAGATGAACTTCATCTACAAACAGTTCAAGAAGTCT

```
AGGATGAGGCCAGGGCTTGGCTACAACGAGGAGCAGATTCACAAGCTGGATAAGGTGAATTTCAGTCATT

TAGCCAAAAGACTCCTGCAGGTGTTCCAGGAGGAGTGCGTGCAGAAGTATCAAGCGTCCTTAGTCACACA

CGGCAAGAGGATGAGGGTGGTGCACGAGACCAGGAACCACCTGCGCCTGGTTGGCTGTTCTGTGGCTGCC

TGTAACACAGAAGCCCAGGGGGTCCAGGAGAGTCTCAGCAAGCATGCAAGAGCTCTGCGAGGGGATGAAG

CTGCTGGCATCTGA
```

IKKε, *Homo sapiens,* isoform 3 (CCDS53464.1), amino acid (631 AA)
SEQ ID NO: 25

```
MEYCSSGSLLSVLESPENAFGLPEDEFLVVLRCVVAGMNHLRENGIVHRDIKPGNIMRLVGRRGQSIYKL

TDFGAARELDDDEKFVSVYGTEEYLHPDMYERAVLRKPQQKAFGVTVDLWSIGVTLYHAATGSLPFIPFG

GPRRNKEIMYPITTEKPAGAIAGAQPPENGPLEWSYTLPITCQLSLGLQSQLVPILANILEVEQAKCWGF

DQFFAETSDILQRVVVHVFSLSQAVLHHIYIHAHNTIAIFQEAVHKQTSVAPRRQEYLFEGHLCVLEPSV

SAQHIAHTTASSPLTLFSTAIPKGLAFRDPALDVPKFVPKVDLQADYNTAKGVLGAGYQALRLARALLDG

QELMFRGLHWVMEVLQATCRRTLEVARTSLLYLSSSLGTERFSSVAGTPEIQELKAAAELRSPLPTLAEV

LSRCSQNITETQESLSSLNRELVKSRDQVHEDRSIQQIQCCLDKMNFIYKQFKKSPMPPGLGYNEEQIHK

LDKVNFSNLAKPLLQVFQEECVQKYQASLVTRGKRMRVVHETRNHLRLVGCSVAACNTEAQGVQESLSKL

LEELSRQLLQDRAKGAQASPPPIAPYPSPTRKDLLLHMQELCEGMKLLASDLLDNNRIIERLNRVPAPPD

V
```

IKKε, *Homo sapiens,* isoform 3 (CCDS53464.1), nucleotide (1896 nt)
SEQ ID NO: 26

```
ATGGAGTACTGCTCCAGTGGGAGCCTGCTGAGTGTGCTGGAGAGCCCTGAGAATGCCTTTGGGCTGCCTG

AGGATGAGTTCCTGGTGGTGCTGCGCTGTGTGGTGGCCGGCATGAACCACCTGCGGGAGAACGGCATTGT

GCATCGCGACATCAAGCCGGGGAACATCATGCGCCTCGTAGGGGAGGAGGGGCAGAGCATCTACAAGCTG

ACAGACTTCGGCGCTGCCCGGGAGCTGGATGATGATGAGAAGTTCGTCTCGGTCTATGGGACTGAGGAGT

ACCTGCATCCCGACATGTATGAGCGGGCGGTGCTTCGAAAGCCCCAGCAAAAAGCGTTCGGGGTGACTGT

GGATCTCTGGAGCATTGGAGTGACCTTGTACCATGCAGCCACTGGCAGCCTGCCCTTCATCCCCTTTGGT

GGGCCACGGCGGAACAAGGAGATCATGTACCGGATCACCACGGAGAAGCCGGCTGGGGCCATTGCAGGTG

CCCAGAGGCGGGAGAACGGGCCCCTGGAGTGGAGCTACACCCTCCCCATCACCTGCCAGCTGTCACTGGG

GCTGCAGAGCCAGCTGGTGCCCATCCTGGCCAACATCCTGGAGGTGGAGCAGGCCAAGTGCTGGGGCTTC

GACCAGTTCTTTGCGGAGACCAGTGACATCCTGCAGCGAGTTGTCGTCCATGTCTTCTCCCTGTCCCAGG

CAGTCCTGCACCACATCTATATCCATGCCCACAACACGATAGCCATTTTCCAGGAGGCCGTGCACAAGCA

GACCAGTGTGGCCCCCCGACACCAGGAGTACCTCTTTGAGGGTCACCTCTGTGTCCTCGAGCCCAGCGTC

TCAGCACAGCACATCGCCCACACGACGGCAAGCAGCCCCCTGACCCTCTTCAGCACAGCCATCCCTAAGG

GGCTGGCCTTCAGGGACCCTGCTCTGGACGTCCCCAAGTTCGTCCCCAAAGTGGACCTGCAGGCGGATTA

CAACACTGCCAAGGGCGTGTTGGGCGCCGGCTACCAGGCCCTGCGGCTGGCACGGGCCCTGCTGGATGGG

CAGGAGCTAATGTTTCGGGGGCTGCACTGGGTCATGGAGGTGCTCCAGGCCACATGCAGACGGACTCTGG

AAGTGGCAAGGACATCCCTCCTCTACCTCAGCAGCAGCCTGGGAACTGAGAGGTTCAGCAGCGTGGCTGG

AACGCCTGAGATCCAGGAACTGAAGGCGGCTGCAGAACTGAGGTCCAGGCTGCGGACTCTAGCGGAGGTC

CTCTCCAGATGCTCCCAAAATATCACGGAGACCCAGGAGAGCCTGAGCAGCCTGAACCGGGAGCTGGTGA

AGAGCCGGGATCAGGTACATGAGGACAGAAGCATCCAGCAGATTCAGTGCTGTTTGGACAAGATGAACTT

CATCTACAAACAGTTCAAGAAGTCTAGGATGAGGCCAGGGCTTGGCTACAACGAGGAGCAGATTCACAAG

CTGGATAAGGTGAATTTCAGTCATTTAGCCAAAAGACTCCTGCAGGTGTTCCAGGAGGAGTGCGTGCAGA

AGTATCAAGCGTCCTTAGTCACACACGGCAAGAGGATGAGGGTGGTGCACGAGACCAGGAACCACCTGCG

CCTGGTTGGCTGTTCTGTGGCTGCCTGTAACACAGAAGCCCAGGGGGTCCAGGAGAGTCTCAGCAAGCTC
```

-continued

CTGGAAGAGCTATCTCACCAGCTCCTTCAGGACCGAGCAAAGGGGGCTCAGGCCTCGCCGCCTCCCATAG

CTCCTTACCCCAGCCCTACACGAAAGGACCTGCTTCTCCACATGCAAGAGCTCTGCGAGGGGATGAAGCT

GCTGGCATCTGACCTCCTGGACAACAACCGCATCATCGAACGGCTAAATAGAGTCCCAGCACCTCCTGAT

GTCTGA

SP2 serine-rich motif of NFAT, polypeptide
SEQ ID NO: 27
SPQHSPSTSPRASVTEESWLG

SP3 serine-rich motif of NFAT, polypeptide
SEQ ID NO: 28
SPHHSPTPSPHGSPRVSVTDDSWLG NFAT conserved serine-rich motif, polypeptide
SEQ ID NO: 29
SVTEESWLG Polypeptide from mass spectrometry analysis
SEQ ID NO: 30
KRSPSTATLSL Polypeptide from mass spectrometry analysis
SEQ ID NO: 31
TATLSLPSLEA Polypeptide from mass spectrometry analysis
SEQ ID NO: 32
DSSLDLGDG

What is claimed is:

1. A method for suppressing, repressing, or ameliorating cancer in a subject, the method comprising administering to the subject an IKKε inhibitor, wherein the IKKε inhibitor comprises a polynucleotide sequence selected from SEQ ID NO:1 or SEQ ID NO: 2.

2. The method of claim 1, wherein the IKKε inhibitor increases NFAT activation relative to a control.

3. The method of claim 1, wherein the IKKε inhibitor increases T cell response relative to a control.

4. The method of claim 3, wherein CD8 T cell response is increased relative to a control.

5. The method of claim 3, wherein the IKKε inhibitor increases anti-cancer T-cell mediated immunity.

6. The method of claim 3, wherein the T cell response is increased by at least about 2-fold to at least about 10-fold.

7. The method of claim 1, wherein a therapeutically effective amount of the IKKε inhibitor is administered.

8. A method of increasing NFAT activation in a subject, the method comprising administering to the subject an IKKε inhibitor comprising a polynucleotide sequence selected from SEQ ID NO:1 or SEQ ID NO: 2.

9. A method of increasing NFAT activation in a subject, the method comprising administering to the subject an IKKε inhibitor comprising an inhibitory RNA that targets IKKε, wherein CD8 T cell response is increased relative to a control.

10. The method of claim 9, wherein the inhibitory RNA comprises a shRNA.

11. A method of increasing T cell response in a subject, the method comprising administering to the subject an IKKε inhibitor comprising an inhibitory RNA that targets IKKε, wherein CD8 T cell response is increased relative to a control.

12. A method of increasing NFAT activation and T cell response in a subject, the method comprising administering to the subject an IKKε inhibitor comprising an inhibitory RNA that targets IKKε, wherein CD8 T cell response is increased relative to a control.

13. A method of increasing T cell response in a subject, the method comprising administering to the subject an IKKε inhibitor comprising a polynucleotide sequence selected from SEQ ID NO:1 or SEQ ID NO: 2.

14. A method of increasing NFAT activation and T cell response in a subject, the method comprising administering to the subject an IKKε inhibitor comprising a polynucleotide sequence selected from SEQ ID NO:1 or SEQ ID NO: 2.

* * * * *

SEQUENCE LISTING

<160> NUMBER OF SEQ ID NOS: 32

<210> SEQ ID NO 1
<211> LENGTH: 57
<212> TYPE: DNA
<213> ORGANISM: Artificial Sequence
<220> FEATURE:
<223> OTHER INFORMATION: Synthetic Oligonucleotide (IKK shRNA 77)

<400> SEQUENCE: 1
ccggctggac gatgatgaga agtttctcga gaaacttctc atcatcgtcc agttttt 57

<210> SEQ ID NO 2
<211> LENGTH: 58
<212> TYPE: DNA
<213> ORGANISM: Artificial Sequence
<220> FEATURE:
<223> OTHER INFORMATION: Synthetic Oligonucleotide (IKK shRNA 78)

<400> SEQUENCE: 2
ccggagaagt tcgtctcggt ctatgctcga gcatagaccg agacgaactt ctttttg 58

<210> SEQ ID NO 3
<211> LENGTH: 21
<212> TYPE: DNA
<213> ORGANISM: Artificial Sequence
<220> FEATURE:
<223> OTHER INFORMATION: Synthetic Oligonucleotide (q-PCR primer for
Mouse B-Actin)

<400> SEQUENCE: 3
tctacgaggg ctatgctctc c 21

<210> SEQ ID NO 4
<211> LENGTH: 23
<212> TYPE: DNA

-continued

<213> ORGANISM: Artificial Sequence
<220> FEATURE:
<223> OTHER INFORMATION: Synthetic Oligonucleotide (q-PCR primer for Mouse B-Actin)

<400> SEQUENCE: 4
tctttgatgt cacgcacgat ttc 23

<210> SEQ ID NO 5
<211> LENGTH: 23
<212> TYPE: DNA
<213> ORGANISM: Artificial Sequence
<220> FEATURE:
<223> OTHER INFORMATION: Synthetic Oligonucleotide (q-PCR primer for Mouse IL-2)

<400> SEQUENCE: 5
cctgagcagg atggagaatt aca 23

<210> SEQ ID NO 6
<211> LENGTH: 19
<212> TYPE: DNA
<213> ORGANISM: Artificial Sequence
<220> FEATURE:
<223> OTHER INFORMATION: Synthetic Oligonucleotide (q-PCR primer for Mouse IL-2)

<400> SEQUENCE: 6
tccagaacat gccgcagag 19

<210> SEQ ID NO 7
<211> LENGTH: 17
<212> TYPE: DNA
<213> ORGANISM: Artificial Sequence
<220> FEATURE:
<223> OTHER INFORMATION: Synthetic Oligonucleotide (q-PCR primer for Human B-Actin)

<400> SEQUENCE: 7
gcacagagcc tcgcctt 17

<210> SEQ ID NO 8
<211> LENGTH: 17
<212> TYPE: DNA
<213> ORGANISM: Artificial Sequence
<220> FEATURE:
<223> OTHER INFORMATION: Synthetic Oligonucleotide (q-PCR primer for Human B-Actin)

<400> SEQUENCE: 8
gttgtcgacg acgagcg 17

<210> SEQ ID NO 9
<211> LENGTH: 24
<212> TYPE: DNA
<213> ORGANISM: Artificial Sequence
<220> FEATURE:
<223> OTHER INFORMATION: Synthetic Oligonucleotide (q-PCR primer for Human IL-2)

<400> SEQUENCE: 9
aactcaccag gatgctcaca ttta 24

<210> SEQ ID NO 10
<211> LENGTH: 24
<212> TYPE: DNA
<213> ORGANISM: Artificial Sequence -continued
<220> FEATURE:
<223> OTHER INFORMATION: Synthetic Oligonucleotide (q-PCR primer for
      Human IL-2)

<400> SEQUENCE: 10
tccctgggtc ttaagtgaaa gttt 24

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligonucleotide (q-PCR primer for
      ORF57)

<400> SEQUENCE: 11
ccgactacac gcaacacaac 20

<210> SEQ ID NO 12
<211> LENGTH: 21
<212> TYPE: DNA
<213> ORGANISM: Artificial Sequence
<220> FEATURE:
<223> OTHER INFORMATION: Synthetic Oligonucleotide (q-PCR primer for
      ORF57)

<400> SEQUENCE: 12
aaataacctg ggtgctgtca c 21

<210> SEQ ID NO 13
<211> LENGTH: 20
<212> TYPE: DNA
<213> ORGANISM: Artificial Sequence
<220> FEATURE:
<223> OTHER INFORMATION: Synthetic Oligonucleotide (q-PCR primer for
      RTA)

<400> SEQUENCE: 13
tttatcagca cgccatcaac 20

<210> SEQ ID NO 14
<211> LENGTH: 21
<212> TYPE: DNA
<213> ORGANISM: Artificial Sequence
<220> FEATURE:
<223> OTHER INFORMATION: Synthetic Oligonucleotide (q-PCR primer for
      RTA)

<400> SEQUENCE: 14
tgcggaacag gtgtgattat c 21

<210> SEQ ID NO 15
<211> LENGTH: 20
<212> TYPE: DNA
<213> ORGANISM: Artificial Sequence
<220> FEATURE:
<223> OTHER INFORMATION: Synthetic Oligonucleotide (q-PCR primer for
      B-Actin)

<400> SEQUENCE: 15
caggcattgt gatggactcc 20

<210> SEQ ID NO 16
<211> LENGTH: 21
<212> TYPE: DNA
<213> ORGANISM: Artificial Sequence
<220> FEATURE:

<223> OTHER INFORMATION: Synthetic Oligonucleotide (q-PCR primer for B-Actin)

<400> SEQUENCE: 16
caagaaggaa ggctggaaaa g 21

<210> SEQ ID NO 17
<211> LENGTH: 8
<212> TYPE: PRT
<213> ORGANISM: Artificial Sequence
<220> FEATURE:
<223> OTHER INFORMATION: Synthetic Peptide (Major histocompatibility complex (MHC)/peptide tetramers for yHV68 ORF61 524-531/Kb)

<400> SEQUENCE: 17

Thr Ser Ile Asn Phe Val Lys Ile
1 5

<210> SEQ ID NO 18
<211> LENGTH: 9
<212> TYPE: PRT
<213> ORGANISM: Artificial Sequence
<220> FEATURE:
<223> OTHER INFORMATION: Synthetic Peptide (Major histocompatibility complex (MHC)/peptide tetramers for influenza virus NP 366-374/Db)

<400> SEQUENCE: 18

Ala Ser Asn Glu Asn Met Glu Thr Met
1 5

<210> SEQ ID NO 19
<211> LENGTH: 9
<212> TYPE: PRT
<213> ORGANISM: Artificial Sequence
<220> FEATURE:
<223> OTHER INFORMATION: Synthetic Peptide (NFAT conserved serine-rich motif, polypeptide)

<400> SEQUENCE: 19

Ser Val Thr Asp Asp Ser Trp Leu Gly
1 5

<210> SEQ ID NO 20
<211> LENGTH: 7
<212> TYPE: PRT
<213> ORGANISM: Artificial Sequence
<220> FEATURE:
<223> OTHER INFORMATION: Synthetic Peptide (NFAT epitope)

<400> SEQUENCE: 20

Ser Pro Arg Ile Glu Ile Thr
1 5

<210> SEQ ID NO 21
<211> LENGTH: 716
<212> TYPE: PRT
<213> ORGANISM: Homo sapiens

<400> SEQUENCE: 21

Met Gln Ser Thr Ala Asn Tyr Leu Trp His Thr Asp Asp Leu Leu Gly
1 5 10 15

Gln Gly Ala Thr Ala Ser Val Tyr Lys Ala Arg Asn Lys Lys Ser Gly
20 25 30

Glu Leu Val Ala Val Lys Val Phe Asn Thr Thr Ser Tyr Leu Arg Pro
35 40 45

```
Arg Glu Val Gln Val Arg Glu Phe Glu Val Leu Arg Lys Leu Asn His
    50                  55                  60

Gln Asn Ile Val Lys Leu Phe Ala Val Glu Glu Thr Gly Gly Ser Arg
65                  70                  75                  80

Gln Lys Val Leu Val Met Glu Tyr Cys Ser Ser Gly Ser Leu Leu Ser
                85                  90                  95

Val Leu Glu Ser Pro Glu Asn Ala Phe Gly Leu Pro Glu Asp Glu Phe
            100                 105                 110

Leu Val Val Leu Arg Cys Val Val Ala Gly Met Asn His Leu Arg Glu
        115                 120                 125

Asn Gly Ile Val His Arg Asp Ile Lys Pro Gly Asn Ile Met Arg Leu
    130                 135                 140

Val Gly Glu Glu Gly Gln Ser Ile Tyr Lys Leu Thr Asp Phe Gly Ala
145                 150                 155                 160

Ala Arg Glu Leu Asp Asp Asp Glu Lys Phe Val Ser Val Tyr Gly Thr
                165                 170                 175

Glu Glu Tyr Leu His Pro Asp Met Tyr Glu Arg Ala Val Leu Arg Lys
            180                 185                 190

Pro Gln Gln Lys Ala Phe Gly Val Thr Val Asp Leu Trp Ser Ile Gly
        195                 200                 205

Val Thr Leu Tyr His Ala Ala Thr Gly Ser Leu Pro Phe Ile Pro Phe
    210                 215                 220

Gly Gly Pro Arg Arg Asn Lys Glu Ile Met Tyr Arg Ile Thr Thr Glu
225                 230                 235                 240

Lys Pro Ala Gly Ala Ile Ala Gly Ala Gln Arg Arg Glu Asn Gly Pro
                245                 250                 255

Leu Glu Trp Ser Tyr Thr Leu Pro Ile Thr Cys Gln Leu Ser Leu Gly
            260                 265                 270

Leu Gln Ser Gln Leu Val Pro Ile Leu Ala Asn Ile Leu Glu Val Glu
        275                 280                 285

Gln Ala Lys Cys Trp Gly Phe Asp Gln Phe Phe Ala Glu Thr Ser Asp
    290                 295                 300

Ile Leu Gln Arg Val Val Val His Val Phe Ser Leu Ser Gln Ala Val
305                 310                 315                 320

Leu His His Ile Tyr Ile His Ala His Asn Thr Ile Ala Ile Phe Gln
                325                 330                 335

Glu Ala Val His Lys Gln Thr Ser Val Ala Pro Arg His Gln Glu Tyr
            340                 345                 350

Leu Phe Glu Gly His Leu Cys Val Leu Glu Pro Ser Val Ser Ala Gln
        355                 360                 365

His Ile Ala His Thr Thr Ala Ser Ser Pro Leu Thr Leu Phe Ser Thr
    370                 375                 380

Ala Ile Pro Lys Gly Leu Ala Phe Arg Asp Pro Ala Leu Asp Val Pro
385                 390                 395                 400

Lys Phe Val Pro Lys Val Asp Leu Gln Ala Asp Tyr Asn Thr Ala Lys
                405                 410                 415

Gly Val Leu Gly Ala Gly Tyr Gln Ala Leu Arg Leu Ala Arg Ala Leu
            420                 425                 430

Leu Asp Gly Gln Glu Leu Met Phe Arg Gly Leu His Trp Val Met Glu
        435                 440                 445

Val Leu Gln Ala Thr Cys Arg Arg Thr Leu Glu Val Ala Arg Thr Ser
    450                 455                 460

Leu Leu Tyr Leu Ser Ser Ser Leu Gly Thr Glu Arg Phe Ser Ser Val
```

-continued

```
465                 470                 475                 480

Ala Gly Thr Pro Glu Ile Gln Glu Leu Lys Ala Ala Ala Glu Leu Arg
                485                 490                 495

Ser Arg Leu Arg Thr Leu Ala Glu Val Leu Ser Arg Cys Ser Gln Asn
            500                 505                 510

Ile Thr Glu Thr Gln Glu Ser Leu Ser Ser Leu Asn Arg Glu Leu Val
        515                 520                 525

Lys Ser Arg Asp Gln Val His Glu Asp Arg Ser Ile Gln Gln Ile Gln
    530                 535                 540

Cys Cys Leu Asp Lys Met Asn Phe Ile Tyr Lys Gln Phe Lys Lys Ser
545                 550                 555                 560

Arg Met Arg Pro Gly Leu Gly Tyr Asn Glu Glu Gln Ile His Lys Leu
                565                 570                 575

Asp Lys Val Asn Phe Ser His Leu Ala Lys Arg Leu Leu Gln Val Phe
            580                 585                 590

Gln Glu Glu Cys Val Gln Lys Tyr Gln Ala Ser Leu Val Thr His Gly
        595                 600                 605

Lys Arg Met Arg Val Val His Glu Thr Arg Asn His Leu Arg Leu Val
    610                 615                 620

Gly Cys Ser Val Ala Ala Cys Asn Thr Glu Ala Gln Gly Val Gln Glu
625                 630                 635                 640

Ser Leu Ser Lys Leu Leu Glu Glu Leu Ser His Gln Leu Leu Gln Asp
                645                 650                 655

Arg Ala Lys Gly Ala Gln Ala Ser Pro Pro Pro Ile Ala Pro Tyr Pro
            660                 665                 670

Ser Pro Thr Arg Lys Asp Leu Leu Leu His Met Gln Glu Leu Cys Glu
        675                 680                 685

Gly Met Lys Leu Leu Ala Ser Asp Leu Leu Asp Asn Asn Arg Ile Ile
    690                 695                 700

Glu Arg Leu Asn Arg Val Pro Ala Pro Pro Asp Val
705                 710                 715


<210> SEQ ID NO 22
<211> LENGTH: 2151
<212> TYPE: DNA
<213> ORGANISM: Homo sapiens

<400> SEQUENCE: 22

atgcagagca cagccaatta cctgtggcac acagatgacc tgctggggca gggggccact      60

gccagtgtgt acaaggcccg caacaagaaa tccggagagc tggttgctgt gaaggtcttc     120

aacactacca gctacctgcg gccccgcgag gtgcaggtga gggagtttga ggtcctgcgg     180

aagctgaacc accagaacat tgtcaagctc tttgcggtgg aggagacggg cggaagccgg     240

cagaaggtac tggtgatgga gtactgctcc agtgggagcc tgctgagtgt gctggagagc     300

cctgagaatg cctttgggct gcctgaggat gagttcctgg tggtgctgcg ctgtgtggtg     360

gccggcatga accacctgcg ggagaacggc attgtgcatc gcgacatcaa gccggggaac     420

atcatgcgcc tcgtagggga ggaggggcag agcatctaca agctgacaga cttcggcgct     480

gcccgggagc tggatgatga tgagaagttc gtctcggtct atgggactga ggagtacctg     540

catcccgaca tgtatgagcg ggcggtgctt cgaaagcccc agcaaaaagc gttcggggtg     600

actgtggatc tctggagcat tggagtgacc ttgtaccatg cagccactgg cagcctgccc     660

ttcatcccct ttggtgggcc acggcggaac aaggagatca tgtaccggat caccacggag     720
```

```
aagccggctg gggccattgc aggtgcccag aggcgggaga acgggcccct ggagtggagc    780

tacaccctcc ccatcacctg ccagctgtca ctggggctgc agagccagct ggtgcccatc    840

ctggccaaca tcctggaggt ggagcaggcc aagtgctggg gcttcgacca gttctttgcg    900

gagaccagtg acatcctgca gcgagttgtc gtccatgtct tctccctgtc ccaggcagtc    960

ctgcaccaca tctatatcca tgcccacaac acgatagcca ttttccagga ggccgtgcac   1020

aagcagacca gtgtggcccc ccgacaccag gagtacctct ttgagggtca cctctgtgtc   1080

ctcgagccca gcgtctcagc acagcacatc gcccacacga cggcaagcag ccccctgacc   1140

ctcttcagca cagccatccc taaggggctg gccttcaggg accctgctct ggacgtcccc   1200

aagttcgtcc ccaaagtgga cctgcaggcg gattacaaca ctgccaaggg cgtgttgggc   1260

gccggctacc aggccctgcg gctggcacgg gccctgctgg atgggcagga gctaatgttt   1320

cgggggctgc actgggtcat ggaggtgctc caggccacat gcagacggac tctggaagtg   1380

gcaaggacat ccctcctcta cctcagcagc agcctgggaa ctgagaggtt cagcagcgtg   1440

gctggaacgc ctgagatcca ggaactgaag gcggctgcag aactgaggtc caggctgcgg   1500

actctagcgg aggtcctctc cagatgctcc caaaatatca cggagaccca ggagagcctg   1560

agcagcctga accgggagct ggtgaagagc cgggatcagg tacatgagga cagaagcatc   1620

cagcagattc agtgctgttt ggacaagatg aacttcatct acaaacagtt caagaagtct   1680

aggatgaggc cagggcttgg ctacaacgag gagcagattc acaagctgga taaggtgaat   1740

ttcagtcatt tagccaaaag actcctgcag gtgttccagg aggagtgcgt gcagaagtat   1800

caagcgtcct tagtcacaca cggcaagagg atgagggtgg tgcacgagac caggaaccac   1860

ctgcgcctgg ttggctgttc tgtggctgcc tgtaacacag aagcccaggg ggtccaggag   1920

agtctcagca agctcctgga agagctatct caccagctcc ttcaggaccg agcaaagggg   1980

gctcaggcct cgccgcctcc catagctcct taccccagcc ctacacgaaa ggacctgctt   2040

ctccacatgc aagagctctg cgaggggatg aagctgctgg catctgacct cctggacaac   2100

aaccgcatca tcgaacggct aaatagagtc ccagcacctc ctgatgtctg a            2151
```

<210> SEQ ID NO 23
<211> LENGTH: 657
<212> TYPE: PRT
<213> ORGANISM: Homo sapiens

<400> SEQUENCE: 23

```
Met Gln Ser Thr Ala Asn Tyr Leu Trp His Thr Asp Asp Leu Leu Gly
1               5                   10                  15

Gln Gly Ala Thr Ala Ser Val Tyr Lys Ala Arg Asn Lys Lys Ser Gly
            20                  25                  30

Glu Leu Val Ala Val Lys Val Phe Asn Thr Thr Ser Tyr Leu Arg Pro
        35                  40                  45

Arg Glu Val Gln Val Arg Glu Phe Glu Val Leu Arg Lys Leu Asn His
    50                  55                  60

Gln Asn Ile Val Lys Leu Phe Ala Val Glu Glu Thr Gly Gly Ser Arg
65                  70                  75                  80

Gln Lys Val Leu Val Met Glu Tyr Cys Ser Ser Gly Ser Leu Leu Ser
                85                  90                  95

Val Leu Glu Ser Pro Glu Asn Ala Phe Gly Leu Pro Glu Asp Glu Phe
            100                 105                 110

Leu Val Val Leu Arg Cys Val Val Ala Gly Met Asn His Leu Arg Glu
        115                 120                 125
```

-continued

```
Asn Gly Ile Val His Arg Asp Ile Lys Pro Gly Asn Ile Met Arg Leu
    130                 135                 140

Val Gly Glu Glu Gly Gln Ser Ile Tyr Lys Leu Thr Asp Phe Gly Ala
145                 150                 155                 160

Ala Arg Glu Leu Asp Asp Asp Glu Lys Phe Val Ser Val Tyr Gly Thr
                165                 170                 175

Glu Glu Tyr Leu His Pro Asp Met Tyr Glu Arg Ala Val Leu Arg Lys
            180                 185                 190

Pro Gln Gln Lys Ala Phe Gly Val Thr Val Asp Leu Trp Ser Ile Gly
        195                 200                 205

Val Thr Leu Tyr His Ala Ala Thr Gly Ser Leu Pro Phe Ile Pro Phe
    210                 215                 220

Gly Gly Pro Arg Arg Asn Lys Glu Ile Met Tyr Arg Ile Thr Thr Glu
225                 230                 235                 240

Lys Pro Ala Gly Ala Ile Ala Gly Ala Gln Arg Arg Glu Asn Gly Pro
                245                 250                 255

Leu Glu Trp Ser Tyr Thr Leu Pro Ile Thr Cys Gln Leu Ser Leu Gly
            260                 265                 270

Leu Gln Ser Gln Leu Val Pro Ile Leu Ala Asn Ile Leu Glu Val Glu
        275                 280                 285

Gln Ala Lys Cys Trp Gly Phe Asp Gln Phe Phe Ala Glu Thr Ser Asp
    290                 295                 300

Ile Leu Gln Arg Val Val Val His Val Phe Ser Leu Ser Gln Ala Val
305                 310                 315                 320

Leu His His Ile Tyr Ile His Ala His Asn Thr Ile Ala Ile Phe Gln
                325                 330                 335

Glu Ala Val His Lys Gln Thr Ser Val Ala Pro Arg His Gln Glu Tyr
            340                 345                 350

Leu Phe Glu Gly His Leu Cys Val Leu Glu Pro Ser Val Ser Ala Gln
        355                 360                 365

His Ile Ala His Thr Thr Ala Ser Ser Pro Leu Thr Leu Phe Ser Thr
    370                 375                 380

Ala Ile Pro Lys Gly Leu Ala Phe Arg Asp Pro Ala Leu Asp Val Pro
385                 390                 395                 400

Lys Phe Val Pro Lys Val Asp Leu Gln Ala Asp Tyr Asn Thr Ala Lys
                405                 410                 415

Gly Val Leu Gly Ala Gly Tyr Gln Ala Leu Arg Leu Ala Arg Ala Leu
            420                 425                 430

Leu Asp Gly Gln Glu Leu Met Phe Arg Gly Leu His Trp Val Met Glu
        435                 440                 445

Val Leu Gln Ala Thr Cys Arg Arg Thr Leu Glu Val Ala Arg Thr Ser
    450                 455                 460

Leu Leu Tyr Leu Ser Ser Ser Leu Gly Thr Glu Arg Phe Ser Ser Val
465                 470                 475                 480

Ala Gly Thr Pro Glu Ile Gln Glu Leu Lys Ala Ala Ala Glu Leu Arg
                485                 490                 495

Ser Arg Leu Arg Thr Leu Ala Glu Val Leu Ser Arg Cys Ser Gln Asn
            500                 505                 510

Ile Thr Glu Thr Gln Glu Ser Leu Ser Ser Leu Asn Arg Glu Leu Val
        515                 520                 525

Lys Ser Arg Asp Gln Val His Glu Asp Arg Ser Ile Gln Gln Ile Gln
    530                 535                 540
```

-continued

```
Cys Cys Leu Asp Lys Met Asn Phe Ile Tyr Lys Gln Phe Lys Lys Ser
545                 550                 555                 560

Arg Met Arg Pro Gly Leu Gly Tyr Asn Glu Glu Gln Ile His Lys Leu
                565                 570                 575

Asp Lys Val Asn Phe Ser His Leu Ala Lys Arg Leu Leu Gln Val Phe
            580                 585                 590

Gln Glu Glu Cys Val Gln Lys Tyr Gln Ala Ser Leu Val Thr His Gly
        595                 600                 605

Lys Arg Met Arg Val Val His Glu Thr Arg Asn His Leu Arg Leu Val
    610                 615                 620

Gly Cys Ser Val Ala Ala Cys Asn Thr Glu Ala Gln Gly Val Gln Glu
625                 630                 635                 640

Ser Leu Ser Lys His Ala Arg Ala Leu Arg Gly Asp Glu Ala Ala Gly
                645                 650                 655

Ile


<210> SEQ ID NO 24
<211> LENGTH: 1974
<212> TYPE: DNA
<213> ORGANISM: Homo sapiens

<400> SEQUENCE: 24

atgcagagca cagccaatta cctgtggcac acagatgacc tgctggggca gggggccact      60

gccagtgtgt acaaggcccg caacaagaaa tccggagagc tggttgctgt gaaggtcttc     120

aacactacca gctacctgcg gccccgcgag gtgcaggtga gggagtttga ggtcctgcgg     180

aagctgaacc accagaacat tgtcaagctc tttgcggtgg aggagacggg cggaagccgg     240

cagaaggtac tggtgatgga gtactgctcc agtgggagcc tgctgagtgt gctggagagc     300

cctgagaatg cctttgggct gcctgaggat gagttcctgg tggtgctgcg ctgtgtggtg     360

gccggcatga accacctgcg ggagaacggc attgtgcatc gcgacatcaa gccggggaac     420

atcatgcgcc tcgtagggga ggaggggcag agcatctaca agctgacaga cttcggcgct     480

gcccgggagc tggatgatga tgagaagttc gtctcggtct atgggactga ggagtacctg     540

catcccgaca tgtatgagcg ggcggtgctt cgaaagcccc agcaaaaagc gttcggggtg     600

actgtggatc tctggagcat tggagtgacc ttgtaccatg cagccactgg cagcctgccc     660

ttcatcccct ttggtgggcc acggcggaac aaggagatca tgtaccggat caccacggag     720

aagccggctg gggccattgc aggtgcccag aggcgggaga acgggcccct ggagtggagc     780

tacaccctcc ccatcacctg ccagctgtca ctggggctgc agagccagct ggtgcccatc     840

ctggccaaca tcctggaggt ggagcaggcc aagtgctggg gcttcgacca gttctttgcg     900

gagaccagtg acatcctgca gcgagttgtc gtccatgtct tctccctgtc ccaggcagtc     960

ctgcaccaca tctatatcca tgcccacaac acgatagcca ttttccagga ggccgtgcac    1020

aagcagacca gtgtggcccc ccgacaccag gagtacctct ttgagggtca cctctgtgtc    1080

ctcgagccca gcgtctcagc acagcacatc gcccacacga cggcaagcag ccccctgacc    1140

ctcttcagca cagccatccc taaggggctg gccttcaggg accctgctct ggacgtcccc    1200

aagttcgtcc ccaaagtgga cctgcaggcg gattacaaca ctgccaaggg cgtgttgggc    1260

gccggctacc aggccctgcg gctggcacgg gccctgctgg atgggcagga gctaatgttt    1320

cgggggctgc actgggtcat ggaggtgctc caggccacat gcagacggac tctggaagtg    1380

gcaaggacat ccctcctcta cctcagcagc agcctgggaa ctgagaggtt cagcagcgtg    1440
```

-continued

```
gctggaacgc ctgagatcca ggaactgaag gcggctgcag aactgaggtc caggctgcgg   1500

actctagcgg aggtcctctc cagatgctcc caaaatatca cggagaccca ggagagcctg   1560

agcagcctga accgggagct ggtgaagagc cgggatcagg tacatgagga cagaagcatc   1620

cagcagattc agtgctgttt ggacaagatg aacttcatct acaaacagtt caagaagtct   1680

aggatgaggc cagggcttgg ctacaacgag gagcagattc acaagctgga taaggtgaat   1740

ttcagtcatt tagccaaaag actcctgcag gtgttccagg aggagtgcgt gcagaagtat   1800

caagcgtcct tagtcacaca cggcaagagg atgagggtgg tgcacgagac caggaaccac   1860

ctgcgcctgg ttggctgttc tgtggctgcc tgtaacacag aagcccaggg ggtccaggag   1920

agtctcagca agcatgcaag agctctgcga ggggatgaag ctgctggcat ctga         1974
```

<210> SEQ ID NO 25
<211> LENGTH: 631
<212> TYPE: PRT
<213> ORGANISM: Homo sapiens

<400> SEQUENCE: 25

```
Met Glu Tyr Cys Ser Ser Gly Ser Leu Leu Ser Val Leu Glu Ser Pro
1               5                   10                  15

Glu Asn Ala Phe Gly Leu Pro Glu Asp Glu Phe Leu Val Val Leu Arg
            20                  25                  30

Cys Val Val Ala Gly Met Asn His Leu Arg Glu Asn Gly Ile Val His
        35                  40                  45

Arg Asp Ile Lys Pro Gly Asn Ile Met Arg Leu Val Gly Glu Glu Gly
    50                  55                  60

Gln Ser Ile Tyr Lys Leu Thr Asp Phe Gly Ala Ala Arg Glu Leu Asp
65                  70                  75                  80

Asp Asp Glu Lys Phe Val Ser Val Tyr Gly Thr Glu Glu Tyr Leu His
                85                  90                  95

Pro Asp Met Tyr Glu Arg Ala Val Leu Arg Lys Pro Gln Gln Lys Ala
            100                 105                 110

Phe Gly Val Thr Val Asp Leu Trp Ser Ile Gly Val Thr Leu Tyr His
        115                 120                 125

Ala Ala Thr Gly Ser Leu Pro Phe Ile Pro Phe Gly Gly Pro Arg Arg
    130                 135                 140

Asn Lys Glu Ile Met Tyr Arg Ile Thr Thr Glu Lys Pro Ala Gly Ala
145                 150                 155                 160

Ile Ala Gly Ala Gln Arg Arg Glu Asn Gly Pro Leu Glu Trp Ser Tyr
                165                 170                 175

Thr Leu Pro Ile Thr Cys Gln Leu Ser Leu Gly Leu Gln Ser Gln Leu
            180                 185                 190

Val Pro Ile Leu Ala Asn Ile Leu Glu Val Glu Gln Ala Lys Cys Trp
        195                 200                 205

Gly Phe Asp Gln Phe Phe Ala Glu Thr Ser Asp Ile Leu Gln Arg Val
    210                 215                 220

Val Val His Val Phe Ser Leu Ser Gln Ala Val Leu His His Ile Tyr
225                 230                 235                 240

Ile His Ala His Asn Thr Ile Ala Ile Phe Gln Glu Ala Val His Lys
                245                 250                 255

Gln Thr Ser Val Ala Pro Arg His Gln Glu Tyr Leu Phe Glu Gly His
            260                 265                 270

Leu Cys Val Leu Glu Pro Ser Val Ser Ala Gln His Ile Ala His Thr
        275                 280                 285
```

```
Thr Ala Ser Ser Pro Leu Thr Leu Phe Ser Thr Ala Ile Pro Lys Gly
    290                 295                 300

Leu Ala Phe Arg Asp Pro Ala Leu Asp Val Pro Lys Phe Val Pro Lys
305                 310                 315                 320

Val Asp Leu Gln Ala Asp Tyr Asn Thr Ala Lys Gly Val Leu Gly Ala
                325                 330                 335

Gly Tyr Gln Ala Leu Arg Leu Ala Arg Ala Leu Leu Asp Gly Gln Glu
            340                 345                 350

Leu Met Phe Arg Gly Leu His Trp Val Met Glu Val Leu Gln Ala Thr
        355                 360                 365

Cys Arg Arg Thr Leu Glu Val Ala Arg Thr Ser Leu Leu Tyr Leu Ser
    370                 375                 380

Ser Ser Leu Gly Thr Glu Arg Phe Ser Ser Val Ala Gly Thr Pro Glu
385                 390                 395                 400

Ile Gln Glu Leu Lys Ala Ala Ala Glu Leu Arg Ser Arg Leu Arg Thr
                405                 410                 415

Leu Ala Glu Val Leu Ser Arg Cys Ser Gln Asn Ile Thr Glu Thr Gln
            420                 425                 430

Glu Ser Leu Ser Ser Leu Asn Arg Glu Leu Val Lys Ser Arg Asp Gln
        435                 440                 445

Val His Glu Asp Arg Ser Ile Gln Gln Ile Gln Cys Cys Leu Asp Lys
    450                 455                 460

Met Asn Phe Ile Tyr Lys Gln Phe Lys Lys Ser Arg Met Arg Pro Gly
465                 470                 475                 480

Leu Gly Tyr Asn Glu Glu Gln Ile His Lys Leu Asp Lys Val Asn Phe
                485                 490                 495

Ser His Leu Ala Lys Arg Leu Leu Gln Val Phe Gln Glu Glu Cys Val
            500                 505                 510

Gln Lys Tyr Gln Ala Ser Leu Val Thr His Gly Lys Arg Met Arg Val
        515                 520                 525

Val His Glu Thr Arg Asn His Leu Arg Leu Val Gly Cys Ser Val Ala
    530                 535                 540

Ala Cys Asn Thr Glu Ala Gln Gly Val Gln Glu Ser Leu Ser Lys Leu
545                 550                 555                 560

Leu Glu Glu Leu Ser His Gln Leu Leu Gln Asp Arg Ala Lys Gly Ala
                565                 570                 575

Gln Ala Ser Pro Pro Pro Ile Ala Pro Tyr Pro Ser Pro Thr Arg Lys
            580                 585                 590

Asp Leu Leu Leu His Met Gln Glu Leu Cys Glu Gly Met Lys Leu Leu
        595                 600                 605

Ala Ser Asp Leu Leu Asp Asn Asn Arg Ile Ile Glu Arg Leu Asn Arg
    610                 615                 620

Val Pro Ala Pro Pro Asp Val
625                 630
```

```
<210> SEQ ID NO 26
<211> LENGTH: 1896
<212> TYPE: DNA
<213> ORGANISM: Homo sapiens

<400> SEQUENCE: 26

atggagtact gctccagtgg gagcctgctg agtgtgctgg agagccctga gaatgccttt      60

gggctgcctg aggatgagtt cctggtggtg ctgcgctgtg tggtggccgg catgaaccac     120
```

```
ctgcgggaga acggcattgt gcatcgcgac atcaagccgg ggaacatcat gcgcctcgta    180

ggggaggagg ggcagagcat ctacaagctg acagacttcg gcgctgcccg ggagctggat    240

gatgatgaga agttcgtctc ggtctatggg actgaggagt acctgcatcc cgacatgtat    300

gagcgggcgg tgcttcgaaa gccccagcaa aaagcgttcg gggtgactgt ggatctctgg    360

agcattggag tgaccttgta ccatgcagcc actggcagcc tgcccttcat cccctttggt    420

gggccacggc ggaacaagga gatcatgtac cggatcacca cggagaagcc ggctggggcc    480

attgcaggtg cccagaggcg ggagaacggg cccctggagt ggagctacac cctccccatc    540

acctgccagc tgtcactggg gctgcagagc cagctggtgc ccatcctggc caacatcctg    600

gaggtggagc aggccaagtg ctggggcttc gaccagttct ttgcggagac cagtgacatc    660

ctgcagcgag ttgtcgtcca tgtcttctcc ctgtcccagg cagtcctgca ccacatctat    720

atccatgccc acaacacgat agccattttc caggaggccg tgcacaagca gaccagtgtg    780

gccccccgac accaggagta cctctttgag ggtcacctct gtgtcctcga gcccagcgtc    840

tcagcacagc acatcgccca cacgacggca agcagccccc tgaccctctt cagcacagcc    900

atccctaagg ggctggcctt cagggaccct gctctggacg tccccaagtt cgtccccaaa    960

gtggacctgc aggcggatta caacactgcc aagggcgtgt tgggcgccgg ctaccaggcc   1020

ctgcggctgg cacgggccct gctggatggg caggagctaa tgtttcgggg gctgcactgg   1080

gtcatggagg tgctccaggc cacatgcaga cggactctgg aagtggcaag gacatccctc   1140

ctctacctca gcagcagcct gggaactgag aggttcagca gcgtggctgg aacgcctgag   1200

atccaggaac tgaaggcggc tgcagaactg aggtccaggc tgcggactct agcggaggtc   1260

ctctccagat gctcccaaaa tatcacggag acccaggaga gcctgagcag cctgaaccgg   1320

gagctggtga agagccggga tcaggtacat gaggacagaa gcatccagca gattcagtgc   1380

tgtttggaca agatgaactt catctacaaa cagttcaaga agtctaggat gaggccaggg   1440

cttggctaca acgaggagca gattcacaag ctggataagg tgaatttcag tcatttagcc   1500

aaaagactcc tgcaggtgtt ccaggaggag tgcgtgcaga agtatcaagc gtccttagtc   1560

acacacggca agaggatgag ggtggtgcac gagaccagga accacctgcg cctggttggc   1620

tgttctgtgg ctgcctgtaa cacagaagcc caggggggtcc aggagagtct cagcaagctc   1680

ctggaagagc tatctcacca gctccttcag gaccgagcaa agggggctca ggcctcgccg   1740

cctcccatag ctccttaccc cagccctaca cgaaaggacc tgcttctcca catgcaagag   1800

ctctgcgagg ggatgaagct gctggcatct gacctcctgg acaacaaccg catcatcgaa   1860

cggctaaata gagtcccagc acctcctgat gtctga                             1896
```

<210> SEQ ID NO 27
<211> LENGTH: 21
<212> TYPE: PRT
<213> ORGANISM: Artificial Sequence
<220> FEATURE:
<223> OTHER INFORMATION: Synthetic Peptide (SP2 serine-rich motif of NFAT, polypeptide)

<400> SEQUENCE: 27

```
Ser Pro Gln His Ser Pro Ser Thr Ser Pro Arg Ala Ser Val Thr Glu
1               5                   10                  15

Glu Ser Trp Leu Gly
            20
```

<210> SEQ ID NO 28

-continued

```
<211> LENGTH: 25
<212> TYPE: PRT
<213> ORGANISM: Artificial Sequence
<220> FEATURE:
<223> OTHER INFORMATION: Synthetic Peptide (SP3 serine-rich motif of
      NFAT, polypeptide)

<400> SEQUENCE: 28

Ser Pro His His Ser Pro Thr Pro Ser Pro His Gly Ser Pro Arg Val
1               5                   10                  15

Ser Val Thr Asp Asp Ser Trp Leu Gly
            20                  25


<210> SEQ ID NO 29
<211> LENGTH: 9
<212> TYPE: PRT
<213> ORGANISM: Artificial Sequence
<220> FEATURE:
<223> OTHER INFORMATION: Synthetic Peptide (NFAT conserved serine-rich
      motif, polypeptide)

<400> SEQUENCE: 29

Ser Val Thr Glu Glu Ser Trp Leu Gly
1               5


<210> SEQ ID NO 30
<211> LENGTH: 11
<212> TYPE: PRT
<213> ORGANISM: Artificial Sequence
<220> FEATURE:
<223> OTHER INFORMATION: Synthetic Peptide (Polypeptide from mass
      spectrometry analysis)

<400> SEQUENCE: 30

Lys Arg Ser Pro Ser Thr Ala Thr Leu Ser Leu
1               5                   10


<210> SEQ ID NO 31
<211> LENGTH: 11
<212> TYPE: PRT
<213> ORGANISM: Artificial Sequence
<220> FEATURE:
<223> OTHER INFORMATION: Synthetic Peptide (Polypeptide from mass
      spectrometry analysis)

<400> SEQUENCE: 31

Thr Ala Thr Leu Ser Leu Pro Ser Leu Glu Ala
1               5                   10


<210> SEQ ID NO 32
<211> LENGTH: 9
<212> TYPE: PRT
<213> ORGANISM: Artificial Sequence
<220> FEATURE:
<223> OTHER INFORMATION: Synthetic Peptide (Polypeptide from mass
      spectrometry analysis)

<400> SEQUENCE: 32

Asp Ser Ser Leu Asp Leu Gly Asp Gly
1               5
```